(12) United States Patent
Hitosugi et al.

(10) Patent No.: US 12,302,749 B2
(45) Date of Patent: May 13, 2025

(54) IMIDE DERIVATIVE, LUMINESCENT COMPOSITION CONTAINING SAME, LUMINOUS THIN FILM, AND LUMINOUS PARTICLES

(71) Applicant: Konica Minolta, Inc., Tokyo (JP)

(72) Inventors: Shumpei Hitosugi, Hachioji (JP); Yasuo Miyata, Yokohama (JP); Shuho Tanimoto, Saitama (JP)

(73) Assignee: KONICA MINOLTA, INC., Tokyo (JP)

( * ) Notice: Subject to any disclaimer, the term of this patent is extended or adjusted under 35 U.S.C. 154(b) by 781 days.

(21) Appl. No.: 17/280,180

(22) PCT Filed: Oct. 9, 2019

(86) PCT No.: PCT/JP2019/039839
§ 371 (c)(1),
(2) Date: Mar. 25, 2021

(87) PCT Pub. No.: WO2020/075761
PCT Pub. Date: Apr. 16, 2020

(65) Prior Publication Data
US 2021/0351356 A1   Nov. 11, 2021

(30) Foreign Application Priority Data

Oct. 10, 2018   (JP) ................. 2018-191645

(51) Int. Cl.
| | | |
|---|---|---|
| *H10K 85/60* | (2023.01) | |
| *C07D 221/18* | (2006.01) | |
| *C07D 471/06* | (2006.01) | |
| *C07F 7/08* | (2006.01) | |
| *C09K 11/06* | (2006.01) | |
| *H10K 85/40* | (2023.01) | |

(52) U.S. Cl.
CPC ......... *H10K 85/621* (2023.02); *C07D 221/18* (2013.01); *C07D 471/06* (2013.01); *C07F 7/0812* (2013.01); *C09K 11/06* (2013.01); *H10K 85/40* (2023.02); *H10K 85/622* (2023.02); *H10K 85/626* (2023.02); *C09K 2211/1007* (2013.01); *C09K 2211/1014* (2013.01); *C09K 2211/1018* (2013.01); *C09K 2211/1022* (2013.01)

(58) Field of Classification Search
CPC .................................................. H10K 85/621
See application file for complete search history.

(56) References Cited

U.S. PATENT DOCUMENTS

| | | | | |
|---|---|---|---|---|
| 4,845,223 A | * | 7/1989 | Seybold ..................... | C09B 5/62 546/37 |
| 2004/0116493 A1 | | 6/2004 | Sugimori et al. | |
| 2011/0284811 A1 | | 11/2011 | Bindra et al. | |

FOREIGN PATENT DOCUMENTS

| | | | |
|---|---|---|---|
| DE | 102007004016 A1 | | 7/2008 |
| EP | 55363 A1 | * | 7/1982 |
| JP | H03-54263 A | | 3/1991 |
| JP | H11-67450 A | | 3/1999 |
| JP | 3476855 B1 | | 12/2003 |
| JP | 2009-500438 A | | 1/2009 |
| JP | 2016-513338 A | | 5/2016 |
| JP | 2018-100246 A | | 6/2018 |
| KR | 10-1992084 B1 | | 6/2019 |
| WO | 2018/065502 A1 | | 4/2018 |
| WO | 2018/068299 A1 | | 4/2018 |
| WO | 2018/134261 A1 | | 7/2018 |

OTHER PUBLICATIONS

Kaiser, Harald "Synthese von nichtsymmetrisch substituierten Perylen-Fluoreszenzfarbstoffen" Chemische Berichte, 124(3), 529-35 1991.*
Ahrens "Cyanated perylene-3,4-dicarboximides and perylene-3,4:9, 10-bis(dicarboximide): facile chromophoric oxidants for organic photonics and electronics." Chemistry of Materials, 2003, 15(14), 2684-2686.*
Chemical Abstract Services Database CAPLUS Abstract 2011:1502586 Document No. 156:25404 entry for Bindra US 20110284811 A1 (abstract only).*
Rademacher, "Soluble perylene fluorescent dyes with high photostability." Chemische Berichte, 1982, 115(8), 2927-34.*
PCT, International Search Report for the corresponding application No. PCT/JP2019/039839, dated Dec. 17, 2019, with English translation.

(Continued)

*Primary Examiner* — David K O'Dell
(74) *Attorney, Agent, or Firm* — LUCAS & MERCANTI, LLP

(57) ABSTRACT

An imide derivative has a structure represented by general formula (1) below.

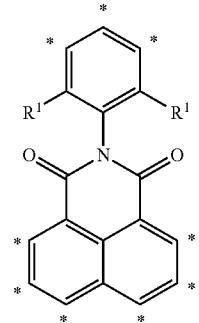

General formula (1)

In the general formula (1), a plurality of $R^1$ each independently represent a hydrogen atom or a substituent. At least one $R^1$ represents a group having 4 to 30 carbon atoms. A benzene ring or naphthalene ring optionally further has a substituent, and * represents a position of a substituent that the benzene ring or naphthalene ring optionally has.

8 Claims, No Drawings

(56) References Cited

OTHER PUBLICATIONS

PCT, Written Opinion for the corresponding application No. PCT/JP2019/039839, dated Dec. 17, 2019, with English translation.
Yu, Y. et al., "Dyes and Pigments," Jul. 6, 2018, pp. 483-490, vol. 159.
Office Action dated Sep. 26, 2023 for the corresponding Japanese Application No. 2020-551202, with English translation.
Tanja Weil, et al; Water-Soluble Rylen Dyes as High-Performance Colorants for the Staining of Cells; Biomacromolecules, 2005, vol. 6, pp. 68-79.
Tanja Weil, et al; Polyphenylene Dendrimers with Different Fluorescent Chromophores Asymmetrically Distributed at the Periphery; J. Am. Chem. Soc., 2001, vol. 123, pp. 8101-8108.
Frank O. Holtrup, et al; Terrylenimides: New NIR Fluorescent Dyes; Chem. Eur. J., 1997, vol. 3, No. 2, pp. 219-225.

* cited by examiner

IMIDE DERIVATIVE, LUMINESCENT COMPOSITION CONTAINING SAME, LUMINOUS THIN FILM, AND LUMINOUS PARTICLES

CROSS REFERENCE TO RELATED APPLICATION

This Application is a 371 of PCT/JP2019/039839 filed on Oct. 9, 2019, which claims priority of Japanese patent application no. 2018-191645 filed Oct. 10, 2018, the above applications are incorporated herein by reference.

TECHNICAL FIELD

The present invention relates to an imide derivative, a luminescent composition containing the imide derivative, a luminous thin film, and a luminous particle(s). More specifically, the present invention relates to an imide derivative having a high luminous quantum yield because of suppressed concentration quenching.

BACKGROUND ART

A perylene bisimide derivative is a substance whose skeleton is known as of 1995 at least. The perylene bisimide derivative is used as a light luminescent material because of potentially high luminous quantum yield, high robustness, ease of emission wavelength adjustment, and ease of synthesis (see, for example, Patent Literature 1).

The perylene bisimide derivative, which is a polycyclic aromatic compound having a large π-conjugated plane, shows luminescence derived from the π-π* transition, and shows a high luminescence quantum yield in a dilute solution. However, in a high-concentration solution or in a solid, it has a drawback that the luminous quantum yield is remarkably lowered. Due to this concentration quenching, the perylene bisimide derivative was not suitably used as a fluorescent dye in high-concentration particles or thin films.

CITATION LIST

Patent Literature

[Patent Literature 1] WO2018/065502A1

SUMMARY OF INVENTION

Technical Problem

The present invention has been made in view of the above problems and situations, and an object to be obtained by the present invention is to provide an imide derivative having a high luminous quantum yield because of suppressed concentration quenching, and to provide a luminous composition, a luminous thin film, and luminous particles containing the same.

Solution to Problem

The present inventors have found that, in the course of studies about the causes of the above problems in order to solve the above problems, concentration quenching can be suppressed by introducing a bulky substituent at a specific position in the perylene bisimide derivative such that the bulky substituent sterically prevents π-π stacking of the perylene bisimide derivative. Furthermore, they have found that the effect of suppressing concentration quenching by introducing the bulky substituent at a specific position can be applied to a naphthaleneimide derivative constituting a partial skeleton of the perylenebisimide derivative, and have conceived the present invention.

That is, the object of the present invention can be achieved by the following means.

1. An imide derivative having a structure represented by general formula (1) below.

[Chem 1]

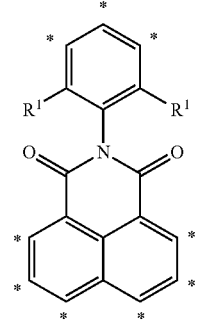

General formula (1)

(In the general formula (1), a plurality of $R^1$ each independently represent a hydrogen atom or a substituent, at least one $R^1$ represents a group having 4 to 30 carbon atoms; and a benzene ring or naphthalene ring optionally further has a substituent, and * represents a position of a substituent that the benzene ring or naphthalene ring optionally has.)

2. The imide derivative according to item 1, wherein the imide derivative having a structure represented by the general formula (1) has a structure represented by general formula (2-1) to general formula (2-6) below.

[Chem 2]

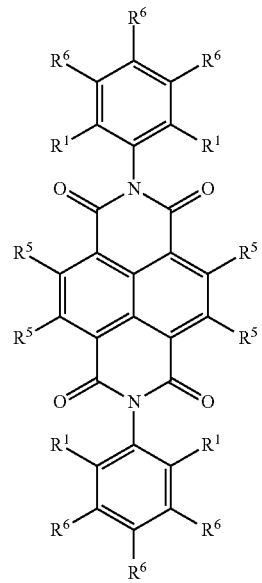

General formula (2-1)

General formula (2-2)
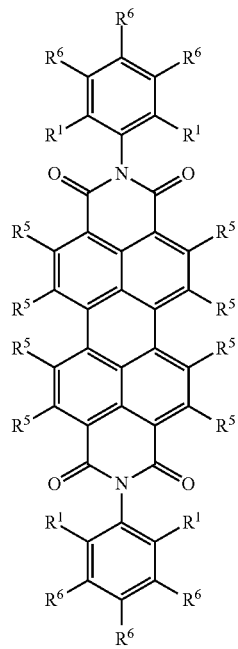
General formula (2-4)
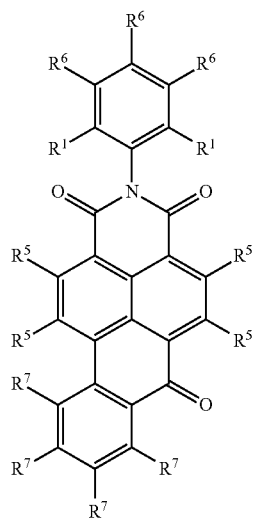
General formula (2-3)
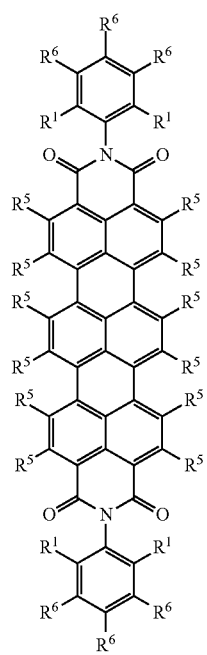
General formula (2-5)
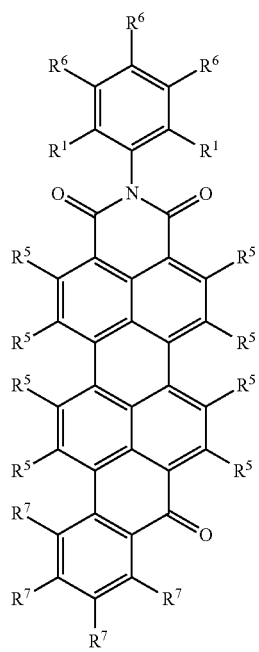

General formula (2-6)

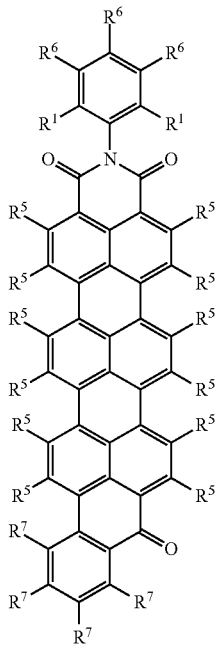

[Chem 4]

General formula (3)

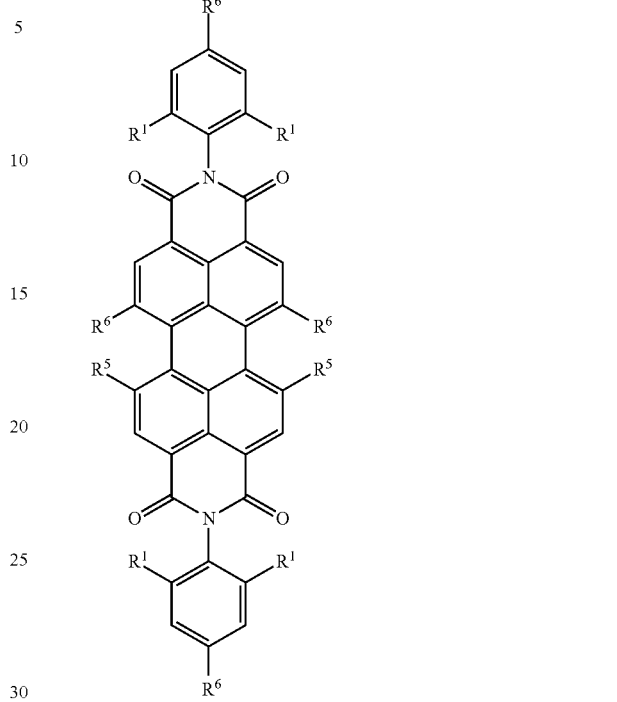

(In the general formula (2-1) to general formula (2-6), a plurality of $R^1$ each independently represent a hydrogen atom or a substituent, at least one $R^1$ represents a group having 4 to 30 carbon atoms; and $R^5$, $R^6$, and $R^7$ each independently represent a hydrogen atom, an alkyl group, an aryl group, a heteroaryl group, an alkenyl group, an alkynyl group, an alkoxy group, or an aryloxy group, and in the general formula (2-2), $R^5$ that represents an aryloxy group represents an aryloxy group other than a group represented by general formula (2-2-1) below.)

[Chem 3]

General formula (2-2-1)

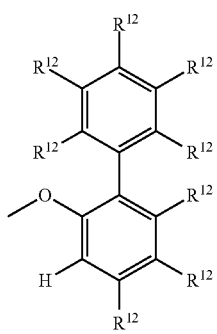

(In the general formula (2-2-1), $R^{12}$ represents a substituent.)

3. The imide derivative according to item 2, wherein the imide derivative having a structure represented by the general formula (2-2) has a structure represented by general formula (3) below.

(In the general formula (3), a plurality of $R^1$ each independently represent a hydrogen atom or a substituent, at least one $R^1$ represents a group having 4 to 30 carbon atoms; a plurality of $R^5$ each independently represent a hydrogen atom, an alkyl group, an aryl group, a heteroaryl group, an alkenyl group, an alkynyl group, an alkoxy group, or an aryloxy group; $R^5$ that represents an aryloxy group represents an aryloxy group other than a group represented by the general formula (2-2-1); and $R^6$ each independently represent a hydrogen atom, an alkyl group, an aryl group, a heteroaryl group, an alkenyl group, an alkynyl group, an alkoxy group, or an aryloxy group.)

4. The imide derivative according to item 3, wherein $R^5$ in the general formula (3) represents an aryloxy group other than a group represented by the general formula (2-2-1).

5. The imide derivative according to item 3, wherein the imide derivative having a structure represented by the general formula (3) has a structure represented by general formula (4) below.

[Chem 5]

General formula (4)

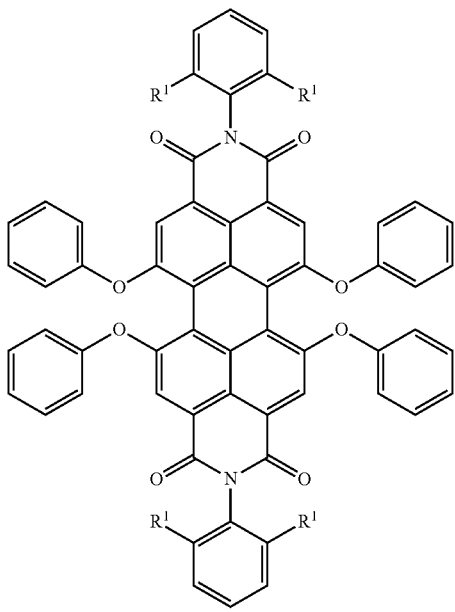

(In the general formula (4), a plurality of $R^1$ each independently represent a hydrogen atom or a substituent, and at least one $R^1$ represents a group having 4 to 30 carbon atoms.)

6. An imide derivative having a structure represented by general formula (5) below.

[Chem 6]

General formula (5)

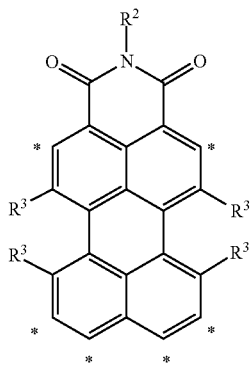

(In the general formula (5), $R^2$ represents a substituted or unsubstituted alkyl group, aryl group, or heteroaryl group; a plurality of $R^3$ each independently represent a hydrogen atom or a group having a structure represented by general formula (6) below, and at least one $R^3$ represents a group having a structure represented by general formula (6) below; and a naphthalene ring optionally further has a substituent, and * represents a position of a substituent that the naphthalene ring optionally has.)

[Chem 7]

General formula (6)

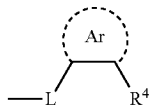

(In the general formula (6), Ar represents an aryl ring or a heteroaryl ring; $R^4$ represents a substituent other than a phenyl group; when two or more groups represented by general formula (6) are present, two $R^4$ are optionally coupled to each other; L represents a single bond, an oxygen atom, a sulfur atom, or —NR'—; and R' represents a hydrogen atom, an alkyl group, an aryl group, or a heteroaryl group.)

7. The imide derivative according to item 6, wherein the imide derivative having a structure represented by the general formula (5) has a structure represented by general formula (7-1) to general formula (7-4) below.

[Chem 8]

General formula (7-1)

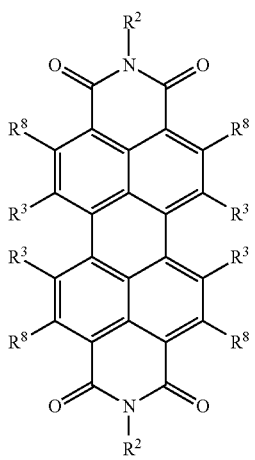

General formula (7-2)

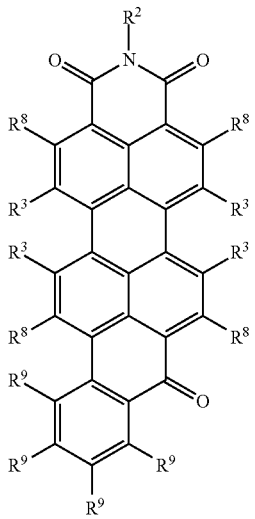

-continued

General formula (7-3)

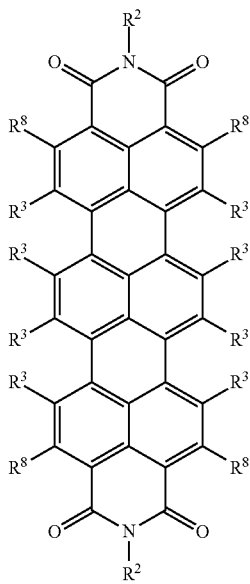

General formula (7-4)

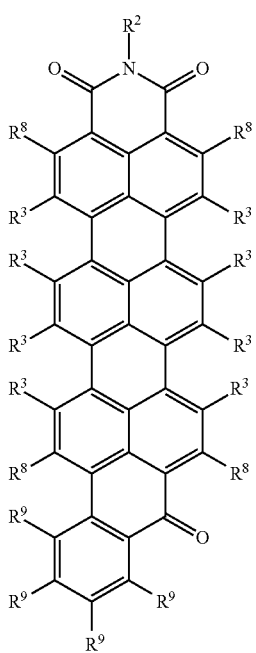

(In the general formula (7-1) to general formula (7-4), $R^2$ each independently represents a substituted or unsubstituted alkyl group, aryl group, or heteroaryl group; a plurality of $R^3$ each independently represent a hydrogen atom or a group having a structure represented by the general formula (6), and at least one $R^3$ represents a group having a structure represented by the general formula (6); and $R^8$ and $R^9$ each independently represent a hydrogen atom, an alkyl group, an alkenyl group, an alkynyl group, an aryl group, a heteroaryl group, an alkoxy group, or an aryloxy group.)

8. The imide derivative according to item 7, wherein the imide derivative having a structure represented by the general formula (7-1) has a structure represented by general formula (8) below.

[Chem 9]

General formula (8)

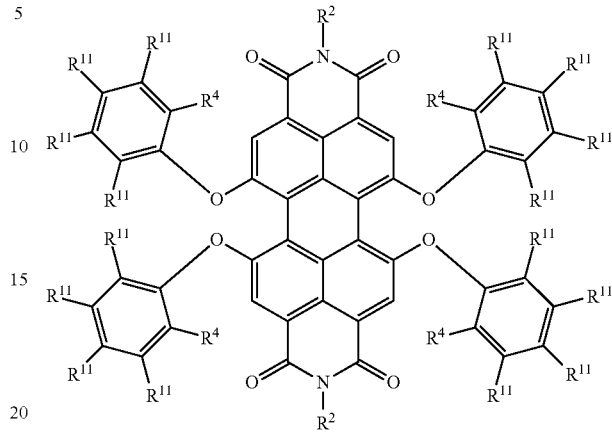

(In the general formula (8), a plurality of $R^2$ each independently represent a substituted or unsubstituted alkyl group, aryl group, or heteroaryl group; $R^4$ each represent a substituent other than a phenyl group; $R^4$ are optionally coupled to each other; and $R^{11}$ each independently represents a hydrogen atom, an alkyl group, an aryl group, a heteroaryl group, an alkenyl group, an alkynyl group, an alkoxy group, an aryloxy group, an amino group, an acyl group, an acyloxy group, an amide group, a carboxy group, or a sulfo group.)

9. The imide derivative according to item 8, wherein, in the general formula (8), any two $R^4$ are coupled to each other across a perylene.

10. A luminescent composition including:
   the imide derivative according to any one of item 1 to item 9.

11. A luminous thin film including:
   the imide derivative according to any one of item 1 to item 9.

12. A luminous particle including:
   the imide derivative according to any one of item 1 to item 9.

Advantageous Effects of Invention

By the above-described means of the present invention, it is possible to provide an imide derivative having a high luminous quantum yield in which concentration quenching is suppressed. Furthermore, a luminescent composition, a luminous thin film, and luminous particles containing the same can be provided.

Although the mechanism of expression or mechanism of action of the effect of the present invention has not been clarified, it is presumed as follows.

It is speculated that the bulky substituent suppresses the π-π stacking of the perylene ring or naphthalene ring between the molecules of the imide derivative, thereby suppressing the non-radiation relaxation process and improving the luminous quantum yield.

DESCRIPTION OF EMBODIMENTS

The imide derivative of the present invention is characterized by having a structure represented by the above general formula (1) or the general formula (5). This feature is a technical feature common to or corresponding to each of the following embodiments (modes).

In an embodiment of the present invention, from the viewpoint of exhibiting the effect of the present invention, the imide derivative having a structure represented by the general formula (1) preferably has a structure represented by the above general formula (2-1) to general formula (2-6).

Furthermore, the imide derivative having the structure represented by the above general formula (2-2) preferably includes the structure represented by the above general formula (3), such that the perylene bisimide derivative has a high luminous quantum yield and high light resistance.

Furthermore, in the present invention, in the above general formula (3), it is preferable that $R^5$ represents an aryloxy group other than the group represented by the above general formula (2-2-1).

Furthermore, the imide derivative having the structure represented by the above general formula (3) as a fluorescent dye preferably has the structure represented by the above general formula (4), such that its bay area has a phenoxy group, the solubility is improved, and the emission wavelength becomes longer.

Furthermore, the imide derivative preferably has the structure represented by the above general formula (5), such that the ortho-substituted group of the aryl ring is oriented toward the perylene ring, effectively shields the π plane, and results in a high quantum yield.

Furthermore, in the present invention, the imide derivative having the structure represented by the above general formula (5) preferably has the structure represented by the general above formula (7-1) to formula (7-4).

Furthermore, the imide derivative having the structure represented by the above general formula (7-1) preferably has the structure represented by the above general formula (8). This is desirable because all four bay areas are phenoxy groups, the substituents $R^4$ are oriented above and below the perylene ring, and the shielding effect of the π plane is enhanced.

Furthermore, in the present invention, in the above general formula (8), any two $R^4$ are preferably coupled to each other across perylene, such that the interaction between perylene rings can be effectively inhibited, and a higher fluorescence quantum yield can be exhibited.

Furthermore, the imide derivative of the present invention can be preferably used for a luminescent composition, a luminous thin film, and luminous particles.

Hereinafter, the present invention, constituents thereof, and modes and aspects for carrying out the present invention will be described in detail. In the present invention, "to" is used to mean that it encompasses the preceding and following numerical values as a lower limit value and an upper limit value.

<<Outline of Imide Derivative>>

The imide derivative of the present invention has a structure represented by the above general formula (1) or the above general formula (5).

The present inventors have found that, in order to effectively suppress π-π stacking between molecules, introduction of a bulky substituent that causes steric hindrance as shown in (A) and (B) below improves the luminous quantum yield. Hereinafter, explanation will be given using a peryleneimide derivative as an example.

(A) a Relatively Large Substituent R is Introduced into the Ortho Position of the Phenyl Group of N-Phenylimide Structure.

As shown below, as the phenyl group is oriented vertical to the perylene ring due to steric hindrance between a carbonyl group of the imide and the substituent R, the substituent R on the ortho position can effectively shield the π plane. In the schematic diagram below, the plate-shaped hatched portion schematically represents the perylene ring plane.

[Chem 10]

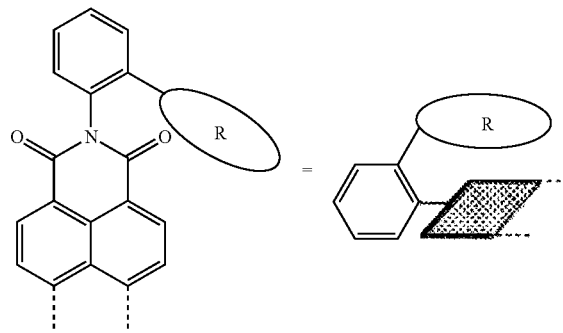

(B) An Aryl Group Having an Ortho-Substituent R is Introduced into a Bay Area of the Perylene Ring.

As shown below, since the aryl group (in this case, phenyl group) is oriented vertical to the perylene ring due to steric crowding in the bay area of the perylene ring, the substituent R on the ortho position effectively shields the π plane.

[Chem 11]

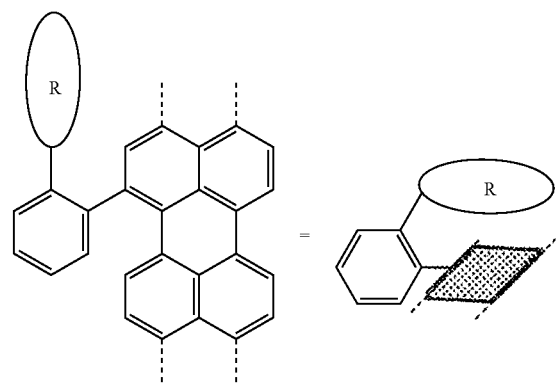

As a structure of a shielding group that is desirable for effectively shielding a π plane in particular, compounds C-53, C-49, and C-58 will be described as representative examples among the exemplified compounds described later.

C-53: In the above (A), an example of the shielding group that effectively interacts with the π plane is a cycloalkyl group via an alkyl chain C-49: In the above (A), an example of the shielding group that is coupled by a flexible structure is a branched alkyl group via an oxygen coupling group.

C-58: In the above (B), a shielding group (crosslinked structure) coupling across the π plane is introduced as an example.

[Chem 12]

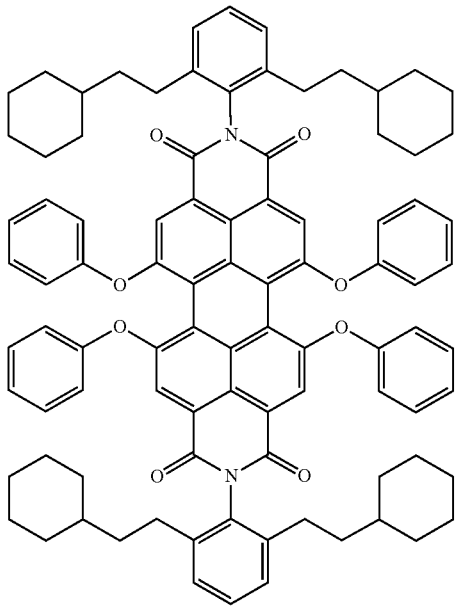

C-53

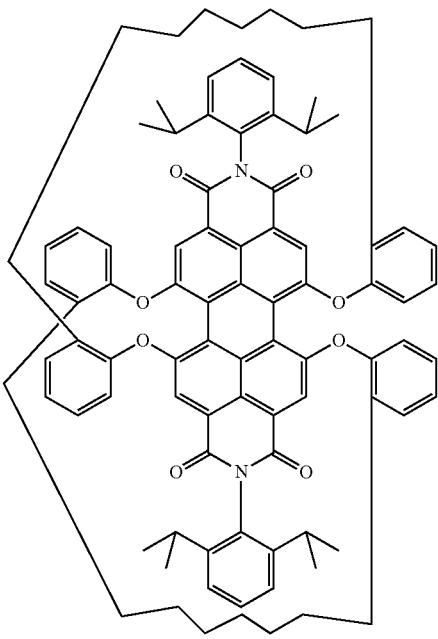

C-58

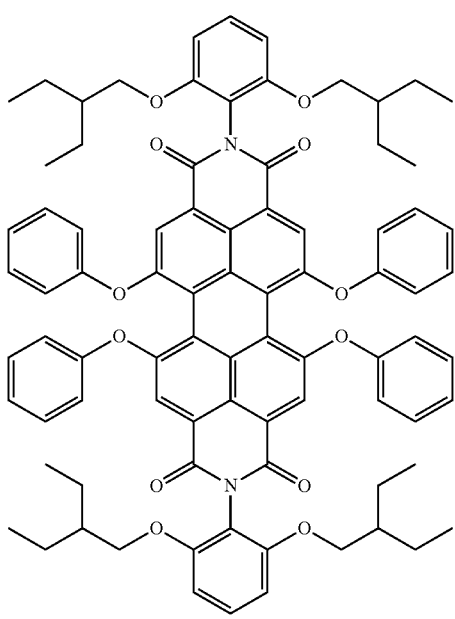

C-49

<<Imide Derivative>>

The imide derivative of the present invention will be described in detail below.

The imide derivative of the present invention has a structure represented by the following general formula (1).

[Imide Derivative Having a Structure Represented by General Formula (1)]

[Chem 13]

General formula (1)

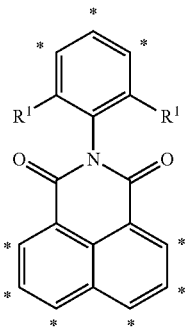

(In the formula, a plurality of $R^1$ each independently represent a hydrogen atom or a substituent, and at least one $R^1$ represents a group having 4 to 30 carbon atoms. The benzene ring or naphthalene ring optionally further has a substituent, and * represents a position of a substituent that the benzene ring or naphthalene ring optionally has.)

By virtue of the bulky (the number of carbons of four or more) substituent present on the ortho position of the phenyl group substituting on the nitrogen atom of the imide, the π plane (naphthalene ring in this case) is shielded, and a high luminous quantum yield can be exhibited.

The substituent that the compound optionally has on the position represented by * is not particularly limited.

Specifically, an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, a pentadecyl group, and the like), a cycloalkyl group (for example, a cyclopentyl group, a cyclohexyl group, and the like), an alkenyl group (for example, a vinyl group, an allyl group, and the like), an alkynyl group (for example, an ethynyl group, a propargyl group, and the like), an aryl group (for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrrenyl group, a biphenylyl group, and the like), a heteroaryl group (for example, a pyridyl group, a pyrimidinyl group, a furyl group, a pyrrolyl group, an imidazolyl group, a benzimidazolyl group, a pyrazolyl group, a pyrazinyl group, a triazolyl group (for example, a 1,2,4-triazol-1-yl group, a 1,2,3-triazol-1-yl group, and the like), a pyrazolo triazolyl group, an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a group in which one of carbon atoms constituting the carboline ring of the above-mentioned carbolinyl group is substituted with a nitrogen atom), a quinoxalinyl group, a pyridazinyl group, a triazinyl group, a quinazolinyl group, a phthalazinyl group, and the like), a heterocyclic group (for example, a pyrrolidyl group, an imidazolydyl group, a morpholyl group, an oxazolydyl group, and the like), an alkoxy group (for example, a methoxy group, an ethoxy group, a propyloxy group, a pentyloxy group, a hexyloxy group, an octyloxy group, a dodecyloxy group, and the like), a cycloalkoxy group (for example, a cyclopentyloxy group, a cyclohexyloxy group, and the like), an aryloxy group (for example, a phenoxy group, a naphthyloxy group, and the like), an alkylthio group (for example, a methylthio group, an ethylthio group, a propylthio group, a pentylthio group, a hexylthio group, an octylthio group, a dodecylthio group, and the like), a cycloalkylthio group (for example, a cyclopentylthio group, a cyclohexylthio group, and the like), an arylthio group (for example, a phenylthio group, a naphthylthio group, and the like), an alkoxycarbonyl group (for example, a methyloxycarbonyl group, an ethyloxycarbonyl group, a butyloxycarbonyl group, an octyloxycarbonyl group, a dodecyloxycarbonyl group, and the like), an aryloxycarbonyl group (for example, a phenyloxycarbonyl group, a naphthyloxycarbonyl group, and the like), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, a 2-pyridylaminosulfonyl group, and the like), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group, and the like), an acyloxy group (for example, an acetyloxy group, an ethylcarbonyloxy group, a butylcarbonyloxy group, an octylcarbonyloxy group, a dodecylcarbonyloxy group, a phenylcarbonyloxy group, and the like), an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, a naphthylcarbonylamino group, and the like), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, a 2-pyridylaminocarbonyl group, and the like), an ureido group (for example, a methylureido group, an ethylureido group, a pentylureido group, a cyclohexylureido group, an octylureido group, a dodecylureido group, a phenylureido group, a naphthylureido group, a 2-pyridylaminoureido group, and the like), a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, a 2-pyridylsulfinyl group, and the like), an alkylsulfonyl group (for example, a methylsulfonyl group, an ethylsulfonyl group, a butylsulfonyl group, a cyclohexylsulfonyl group, a 2-ethylhexylsulfonyl group, a dodecylsulfonyl group, and the like), an arylsulfonyl group or heteroarylsulfonyl group (for example, a phenylsulfonyl group, a naphthylsulfonyl group, a 2-pyridylsulfonyl group, and the like), an amino group (for example, an amino group, an ethylamino group, a dimethylamino group, a diphenylamino group, a diisopropylamino group, a di-tert-butyl group, a cyclohexylamino group, a butylamino group, a cyclopentylamino group, a 2-ethylhexylamino group, a dodecylamino group, an anilino group, a naphthylamino group, a 2-pyridylamino group, and the like), a halogen atom (for example, a fluorine atom, a chlorine atom, a bromine atom, and the like), a fluorinated hydrocarbon group (for example, a fluoromethyl group, a trifluoromethyl group, a pentafluoroethyl group, a pentafluorophenyl group, and the like), a cyano group, a nitro group, a hydroxy group, a mercapto group, a silyl group (for example, a trimethylsilyl group, a triisopropylsilyl group, a triphenylsilyl group, a phenyldiethylsilyl group, and the like), a phosphono group, a carboxy group, and a sulfo group are exemplified.

In addition, these substituents may be further substituted with any of the above-described substituents. Furthermore, these substituents may bind to each other to form a ring. The ring structure formed by substituents adjacent to each other may be an aromatic ring, an aliphatic ring, or a ring containing a heteroatom. Further, the ring structure may be a condensed ring of two or more rings.

It is preferable that no substituent is present on the * position, or the substituent is an alkyl group, a halogen atom, a cyano group, a carboxylic acid anhydride in which two carboxylic acids are condensed, or a condensed ring in which substituents bind to each other.

$R^1$ each independently represents a hydrogen atom or a substituent, and at least one $R^1$ represents a group having 4 to 30 carbon atoms.

Specifically, the substituent represented by $R^1$ can be selected from the above-described substituents that * optionally has. However, at least one $R^1$ represents a group having 4 to 30 carbon atoms. With a group having 4 to 30 carbon atoms, the phenyl group substituting on the nitrogen atom is oriented vertical to the naphthalene ring due to steric hindrance between the carbonyl groups of the imide and $R^1$. Therefore, the substituent $R^1$ on the ortho position effectively shields the π plane. In addition, $R^1$ preferably has an oxygen atom or sulfur atom in its carbon chain. More preferably, $R^1$ has an oxygen atom in its carbon chain. When $R^1$ has an oxygen atom or sulfur atom in its carbon chain, the structure becomes more flexible, and a π plane shielding effect of $R^1$ can be enhanced.

$R^1$ is preferably an alkyl group (for example, a tert-butyl group, a pentyl group, a hexyl group, an octyl group, a dodecyl group, a tridecyl group, a tetradecyl group, a pentadecyl group, a 3-ethylpentyl group, and the like), a cycloalkyl group (for example, a cyclopentyl group, a cyclohexyl group, a cyclohexylethyl group, and the like), an alkenyl group (for example, a propenyl group, a hexenyl group, and the like), an alkynyl group (for example, a propynyl group, a hexynyl group, a phenylethynyl group, and the like), an aryl group (for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenylyl group, and the like), a heteroaryl group (for example, a pyridyl group, a pyrimidyl group, a furyl group, a pyrrolyl group, a benzimidazolyl group, a pyrazolyl group, a pyrazinyl group, a benzoxazolyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a group in which one of carbon atoms constituting the carboline ring of the above-mentioned carbolinyl group is substituted with a nitrogen atom), a quinoxalinyl group, a pyridazinyl group, a triazinyl group, a quinazolinyl group, a phthalazinyl group, and the like), a heterocyclic group (for example, a pyrrolidyl group, an imidazolydyl group, a morpholyl group, an oxazolydyl group, and the like), an alkoxy group (for example, a pentyloxy group, a hexyloxy group, an octyloxy group, a dodecyloxy group, a 2-ethylbutyloxy group, and the like), a cycloalkoxy group (for example, a cyclopentyloxy group, a cyclohexyloxy group, and the like), an aryloxy group (for example, a phenoxy group, a naphthyloxy group, and the like), an alkylthio group (for example, a pentylthio group, a hexylthio group, an octylthio group, a dodecylthio group, and the like), a cycloalkylthio group (for example, a cyclopentylthio group, a cyclohexylthio group, and the like), an arylthio group (for example, a phenylthio group, a naphthylthio group, and the like), an alkoxycarbonyl group (for example, a butyloxycarbonyl group, an octyloxycarbonyl group, a dodecyloxycarbonyl group, and the like), an aryloxycarbonyl group (for example, a phenyloxycarbonyl group, a naphthyloxycarbonyl group, and the like), a sulfamoyl group (for example, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, a 2-pyridylaminosulfonyl group, and the like), an acyl group (for example, a butylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group, and the like), an acyloxy group (for example, a butylcarbonyloxy group, an octylcarbonyloxy group, a dodecylcarbonyloxy group, a phenylcarbonyloxy group, and the like), an amido group (for example, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, a naphthylcarbonylamino group, and the like), a carbamoyl group (for example, a diethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, a 2-pyridylaminocarbonyl group, and the like), an ureido group (for example, a pentylureido group, a cyclohexylureido group, an octylureido group, a dodecylureido group, a phenylureido group, a naphthylureido group, a 2-pyridylaminoureido group, and the like), a sulfinyl group (for example, a butylsulfinyl group, a cyclohexylsulfinyl group, a 2-ethylhexylsulfinyl group, a dodecylsulfinyl group, a phenylsulfinyl group, a naphthylsulfinyl group, a 2-pyridylsulfinyl group, and the like), an alkylsulfonyl group (for example, a butylsulfonyl group, a cyclohexylsulfonyl group, a 2-ethylhexylsulfonyl group, a dodecylsulfonyl group, and the like), an arylsulfonyl group or heteroarylsulfonyl group (for example, a phenylsulfonyl group, a naphthylsulfonyl group, a 2-pyridylsulfonyl group, and the like), an amino group (for example, a diphenylamino group, a diisopropylamino group, a cyclohexylamino group, a butylamino group, a cyclopentylamino group, a 2-ethylhexylamino group, a dodecylamino group, an anilino group, a naphthylamino group, a 2-pyridylamino group, and the like), a fluorinated hydrocarbon group (for example, a decafluorobutyl group, a pentafluorophenyl group, and the like), or a silyl group (for example, a triethylsilyl group, a triisopropylsilyl group, a triphenylsilyl group, a phenyldiethylsilyl group, and the like).

$R^1$ is more preferably a bulky group and includes an aryl group, a heteroaryl group, an alkyl group containing a secondary or higher carbon (for example, a secondary carbon: isobutyl group, cyclohexyl group, cyclopentyl group, and cholesteryl group, a tertiary carbon: tert-butyl group, adamantyl group, and [2,2,2]bicyclooctyl group, and the like), a tertiary amino group (for example, a diethylamino group, a diphenylamino group, and the like), a tertiary silyl group (for example, a triisopropylsilyl group, a triphenylsilyl group, a phenyldiethylsilyl group, and the like), and the like. The terminal of an alkyl group, alkenyl group, alkynyl group, alkoxy group, acyl group, acyloxy group, or amide group can also have such a bulky group.

[Imide Derivative Having a Structure Represented by General Formula (2-1) to General Formula (2-6)]

The imide derivative having a structure represented by general formula (1) preferably has a structure represented by general formula (2-1) to general formula (2-6) below.

[Chem 14]

General formula (2-1)

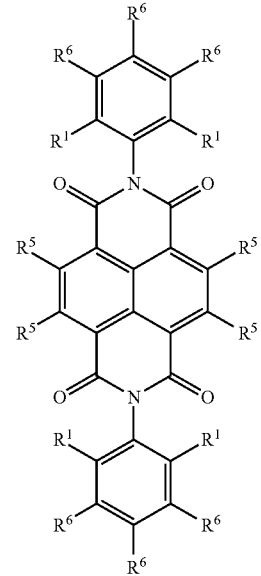

General formula (2-2)
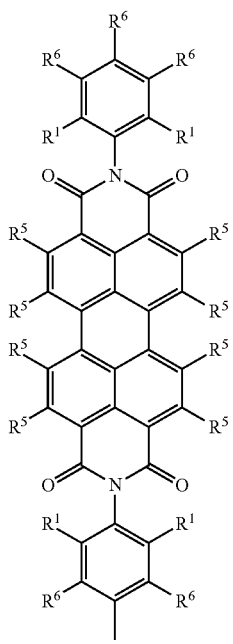
General formula (2-4)
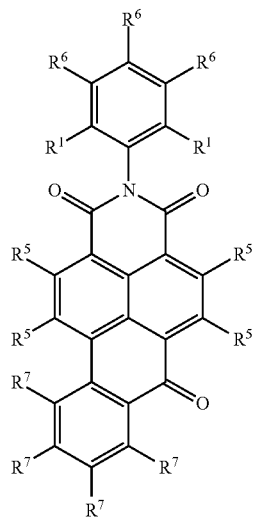
General formula (2-3)
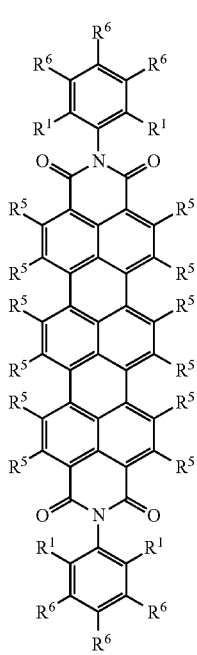
General formula (2-5)
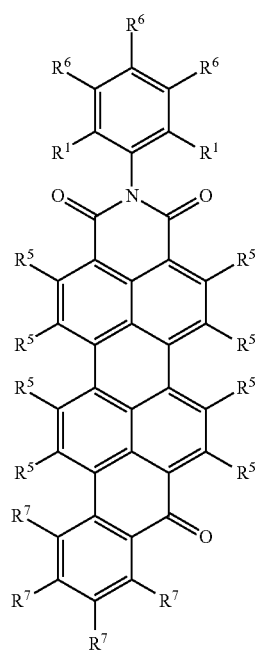

-continued

General formula (2-6)

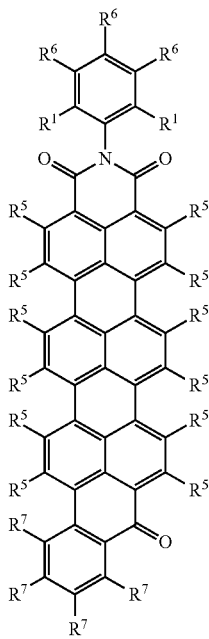

(In the formulas, a plurality of $R^1$ each independently represent a hydrogen atom or a substituent, and at least one $R^1$ represents a group having 4 to 30 carbon atoms. $R^5$, $R^6$, and $R^7$ each independently represent a hydrogen atom, an alkyl group, an aryl group, a heteroaryl group, an alkenyl group, an alkynyl group, an alkoxy group, or an aryloxy group. However, in the general formula (2-2), the aryloxy group represented by $R^5$ represents an aryloxy group other than the group represented by the following general formula (2-2-1).)

[Chem 15]

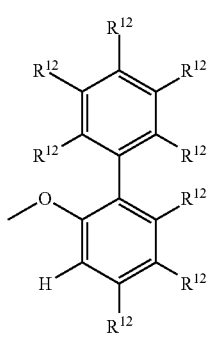

General formula (2-2-1)

(In the formula, $R^{12}$ represents a substituent.)

$R^1$ has the same meaning as $R^1$ in the general formula (1).

$R^5$, $R^6$ and $R^7$ each independently represent a hydrogen atom, an alkyl group, an aryl group, a heteroaryl group, an alkenyl group, an alkynyl group, an alkoxy group or an aryloxy group.

These groups have the same meaning as the alkyl group, aryl group, heteroaryl group, alkenyl group, alkynyl group, alkoxy group or aryloxy group listed as the substituents that * optionally has in the general formula (1).

$R^{12}$ represents a substituent and has the same meaning as the substituent that the compound optionally has on the position represented by * in the general formula (1).

[Imide Derivative Having a Structure Represented by General Formula (3)]

The imide derivative having a structure represented by general formula (2-2) preferably has a structure represented by general formula (3) below.

[Chem. 16]

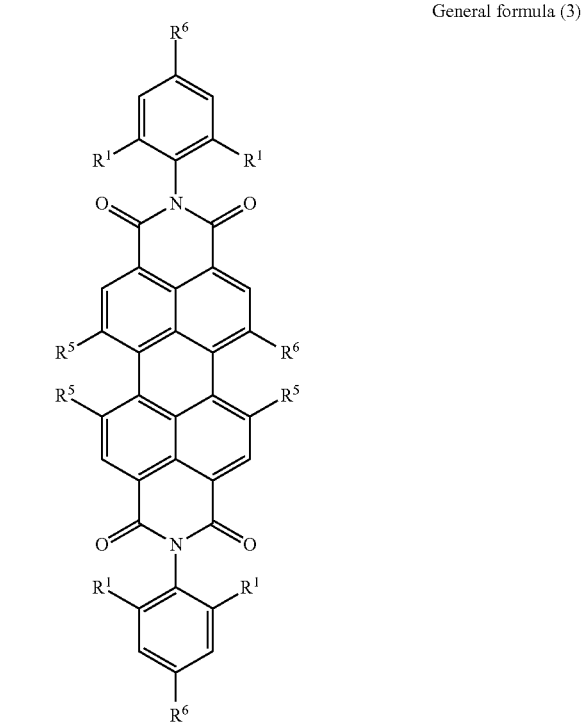

General formula (3)

(In the formula, a plurality of $R^1$ each independently represent a hydrogen atom or a substituent, and at least one $R^1$ represents a group having 4 to 30 carbon atoms. A plurality of $R^5$ each independently represent a hydrogen atom, an alkyl group, an aryl group, a heteroaryl group, an alkenyl group, an alkynyl group, an alkoxy group, or an aryloxy group. However, the aryloxy group represented by $R^5$ represents an aryloxy group other than the group represented by the above general formula (2-2-1). $R^6$ each independently represents a hydrogen atom, an alkyl group, an aryl group, a heteroaryl group, an alkenyl group, an alkynyl group, an alkoxy group, or an aryloxy group.)

A perylene bisimide derivative not only shows high luminous quantum yield but also shows high light resistance and therefore is desirable.

$R^5$ each independently represents a hydrogen atom, an alkyl group, an aryl group, a heteroaryl group, an alkenyl group, an alkynyl group, an alkoxy group, or an aryloxy group and has the same meaning as $R^5$ shown in general formula (2).

$R^6$ each independently represents a hydrogen atom, an alkyl group, an aryl group, a heteroaryl group, an alkenyl group, an alkynyl group, an alkoxy group, or an aryloxy group and has the same meaning as $R^6$ shown in general formula (2).

In the above general formula (3), $R^5$ preferably represents an aryloxy group other than the group represented by the above general formula (2-2-1)

[Imide Derivative Having a Structure Represented by General Formula (4)]

The imide derivative having a structure represented by general formula (3) preferably has a structure represented by general formula (4) below.

[Chem. 17]

General formula (4)

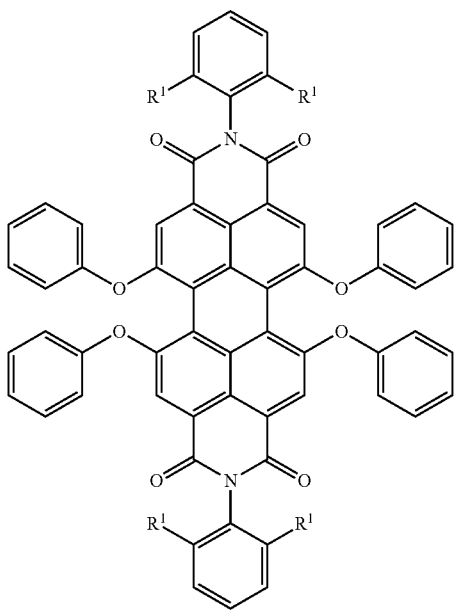

(In the formula, a plurality of $R^1$ each independently represent a hydrogen atom or a substituent, and at least one $R^1$ represents a group having 4 to 30 carbon atoms.)

When a phenoxy group is present in the bay areas, solubility can be improved, and a longer wavelength can be achieved, which is desirable as a fluorescent light-emitting colorant.

$R^1$ has the same meaning as $R^1$ in the general formula (1).

[Imide Derivative Having a Structure Represented by General Formula (5)]

The imide derivative of the present invention preferably has a structure represented by general formula (5).

[Chem 18]

General formula (5)

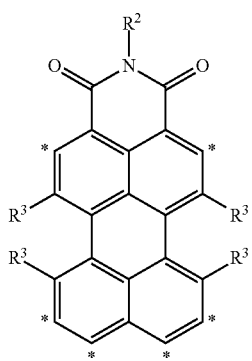

(In the formula, $R^2$ represents a substituted or unsubstituted alkyl group, aryl group, or heteroaryl group. A plurality of $R^3$ each independently represent a hydrogen atom or a group having a structure represented by general formula (6) below, and at least one $R^3$ represents a group having a structure represented by general formula (6) below. The naphthalene ring optionally further has a substituent, and * represents a position of a substituent that the naphthalene ring optionally has.)

[Chem 19]

General formula (6)

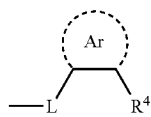

(In the formula, Ar represents an aryl ring or a heteroaryl ring. $R^4$ represents a substituent other than a phenyl group. When two or more groups represented by general formula (6) are present, two $R^4$ are optionally coupled to each other. L represents a single bond, an oxygen atom, a sulfur atom, or —NR'—. R' represents a hydrogen atom, an alkyl group, an aryl group, or a heteroaryl group.)

Since the ortho substituent $R^4$ of the aryl ring or heteroaryl ring represented by Ar is oriented toward the perylene ring and effectively shields the π plane, a high quantum yield can be exhibited.

Ar represents an aryl ring or heteroaryl ring that optionally has a substituent, and examples of the aryl ring can include a benzene ring, naphthalene ring, an azulene ring, an anthracene ring, a phenanthrene ring, a naphthacene ring, a pyrene ring, and the like.

The heteroaryl ring can include a pyridine ring, a pyrimidine ring, a furan ring, a pyrrole ring, an imidazole ring, a benzimidazole ring, a pyrazole ring, a pyrazine ring, a triazole ring, a pyrazolotriazole ring, an oxazole ring, a benzoxazole ring, a thiazole ring, a thiophene ring, a quinoline ring, a benzofuran ring, a dibenzofuran ring, an indole ring, a quinoxaline ring, a triazine ring, and the like.

Ar preferably represents an aryl ring.

$R^4$ represents a substituent other than a phenyl group, and any group can be selected from the substituents that * optionally has in general formula (1) except for a phenyl group.

The alkyl group, aryl group, and heteroaryl group represented by R' have the same meanings as the alkyl group, aryl group, and heteroaryl group listed as substituents that * optionally has in general formula (1), respectively.

$R^4$ is preferably an alkyl group (for example, a methyl group, an ethyl group, a propyl group, a butyl group, a pentyl group, a hexyl group, an isopropyl group, a tert-butyl group, an isobutyl group, or a neopentyl group), a cycloalkyl group (for example, a cyclopentyl group or a cyclohexyl group), an aryl group except for a phenyl group (for example, a naphthyl group or an anthryl group), a heteroaryl group (for example, a pyridyl group or a carbazolyl group), an alkenyl group (for example, a butenyl group, a pentenyl group, or a hexenyl group), an alkynyl group (for example, a propynyl group, a hexynyl group, a phenylethynyl group, or a trimethylsilylethynyl group), a silyl group (for example, a trimethylsilyl group, a triethylsilyl group, or a triphenylsilyl group), an alkoxy group (a methoxy group or a tert-butyloxy group), or an aryloxy group (a phenoxy group or a naphthoxy group).

[Imide Derivative Having a Structure Represented by General Formula (7-1) to General Formula (7-4)]

The imide derivative having a structure represented by general formula (5) preferably has a structure represented by general formula (7-1) to general formula (7-4) below.

[Chem 20]

General formula (7-1)

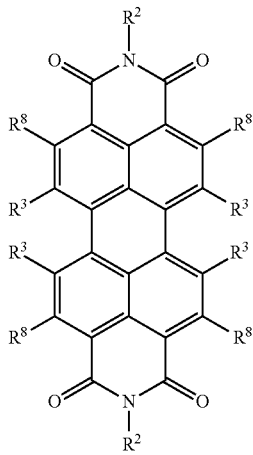

General formula (7-2)

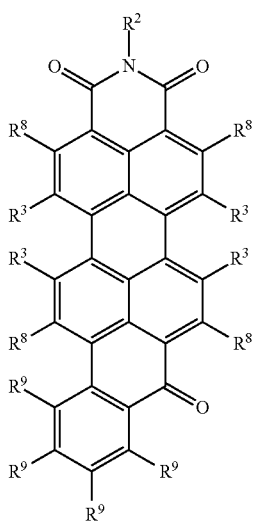

General formula (7-3)

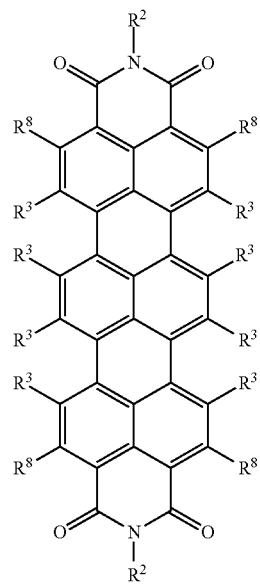

General formula (7-4)

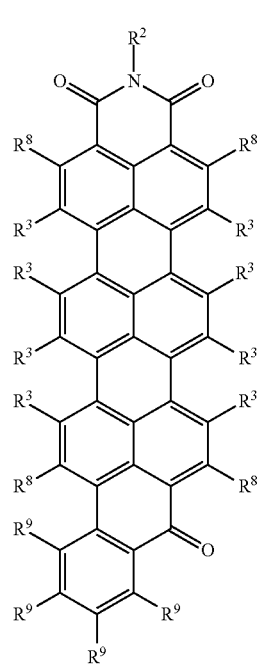

(In the formulas, $R^2$ each independently represents a substituted or unsubstituted alkyl group, aryl group, or heteroaryl group. A plurality of $R^3$ each independently represent a hydrogen atom or a group having a structure represented by the above general formula (6), and at least one $R^3$ represents a group having a structure represented by the above general formula (6). $R^8$ and $R^9$ each independently represent a hydrogen atom, an alkyl group, an alkenyl group, an alkynyl group, an aryl group, a heteroaryl group, an alkoxy group, or an aryloxy group.)

$R^2$ and $R^3$ have the same meanings as $R^2$ and $R^3$ in general formula (5), respectively.

The alkyl group, alkenyl group, alkynyl group, aryl group, heteroaryl group, alkoxy group, and aryloxy group represented by $R^8$ or $R^9$ have the same meanings as the alkyl group, alkenyl group, alkynyl group, aryl group, heteroaryl group, alkoxy group, and aryloxy group listed as substituents that * optionally has in general formula (1), respectively.

[Imide Derivative Having a Structure Represented by General Formula (8)]

The imide derivative having a structure represented by the above general formula (7-1) preferably has a structure represented by general formula (8) below.

[Chem 21]

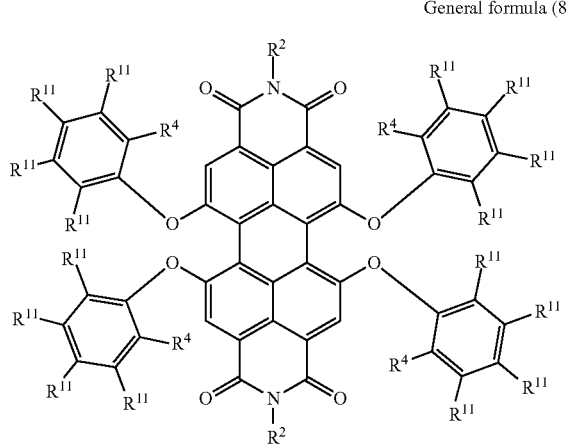

General formula (8)

(In the formula, a plurality of $R^2$ each independently represent a substituted or unsubstituted alkyl group, aryl group, or heteroaryl group. $R^4$ each represent a substituent other than a phenyl group. $R^4$ are optionally coupled to each other. $R^{11}$ each independently represents a hydrogen atom, an alkyl group, an aryl group, a heteroaryl group, an alkenyl group, an alkynyl group, an alkoxy group, an aryloxy group, an amino group, an acyl group, an acyloxy group, an amide group, a carboxy group, or a sulfo group.)

The case where all of the four bay areas are phenoxy groups is desirable because the substituents $R^4$ is each oriented upward or downward from the perylene ring, and shielding effect is enhanced.

$R^2$ and $R^4$ have the same meanings as $R^2$ and $R^4$ in general formula (5), respectively.

Furthermore, the imide derivative having the structure represented by the general formula (8) is preferably an imide derivative having the structure represented by the general formula (8A).

[Chem 22]

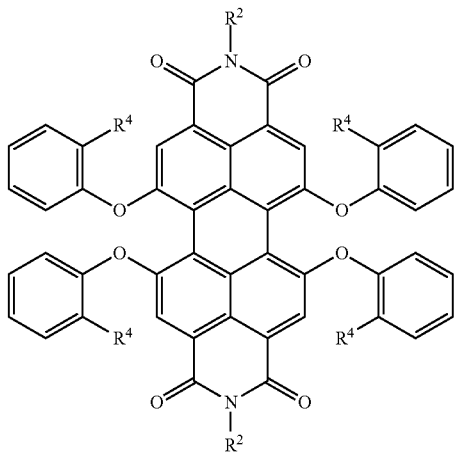

General formula (8A)

(In the formula, a plurality of $R^2$ each independently represents a substituted or unsubstituted alkyl group, aryl group, or heteroaryl group. $R^4$ each represent a substituent other than a phenyl group. $R^4$ are optionally coupled to each other.)

$R^2$ and $R^4$ have the same meanings as $R^2$ and $R^4$ in general formula (8), respectively.

Further, in general formula (8) above, it is desirable that any two $R^4$ are coupled to each other across perylene. The coupling effectively inhibits interaction between perylene rings, and a higher luminous quantum yield is exhibited.

Examples of imide derivatives having structures represented by general formula (1) to formula (8) of the present invention are shown below, but the present invention is not limited thereto.

[Chem 23]

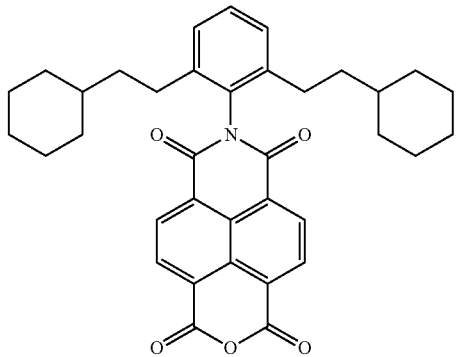

C-1

-continued
C-2
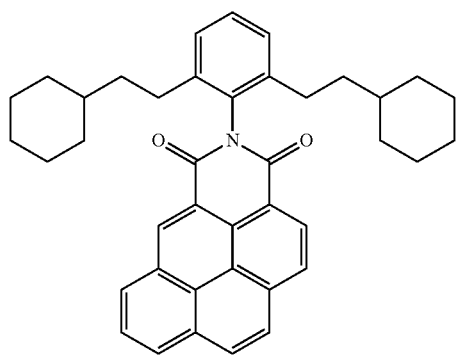
C-3
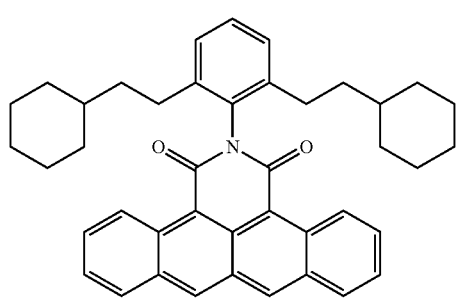
C-4
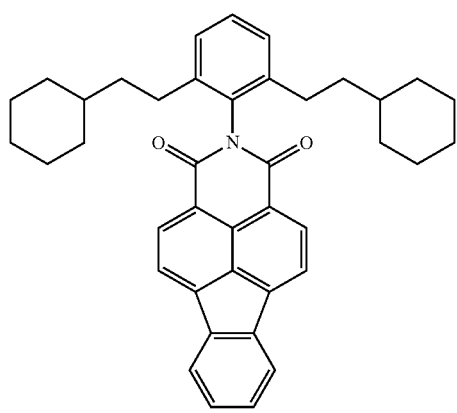
C-5
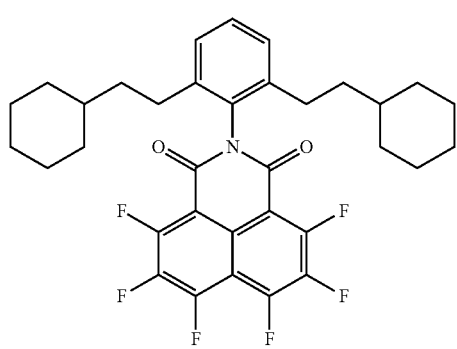
-continued
C-6
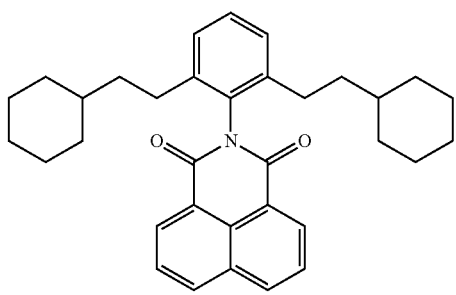
C-7
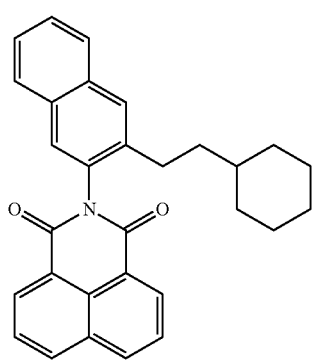
C-8
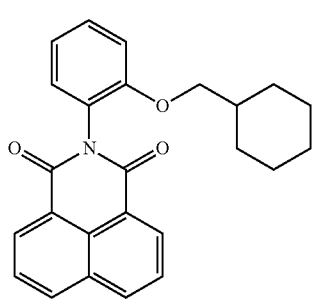
C-9
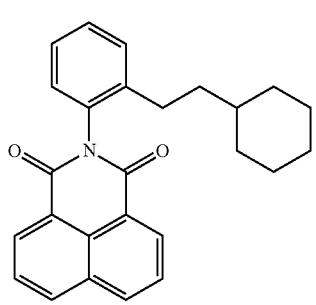

[Chem 24]
C-10
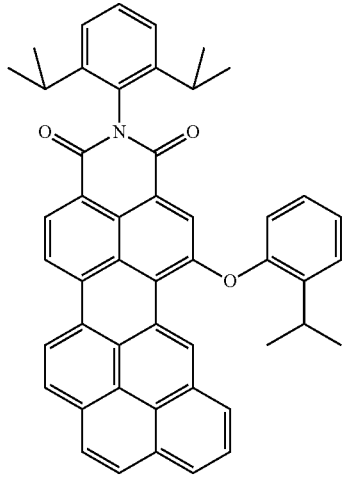
C-11
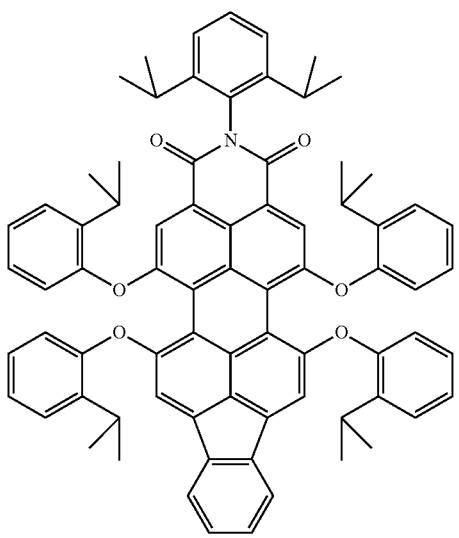
C-12
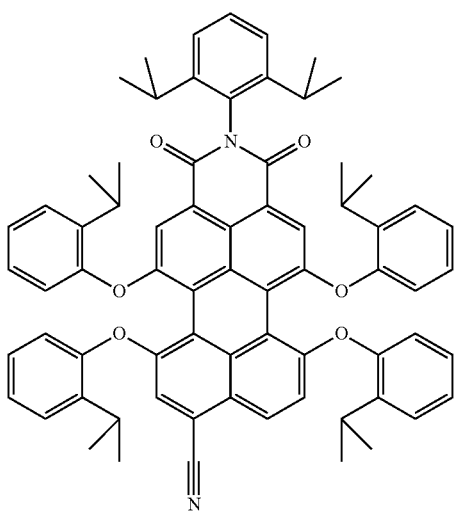
C-13
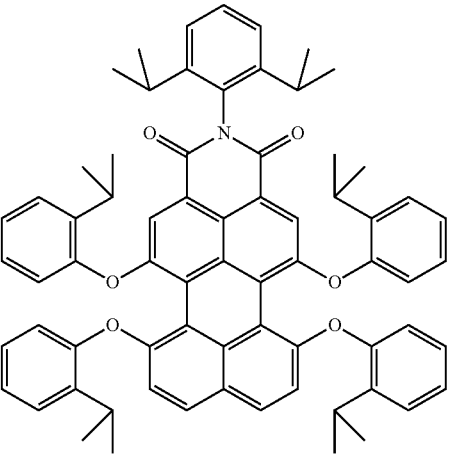
C-14
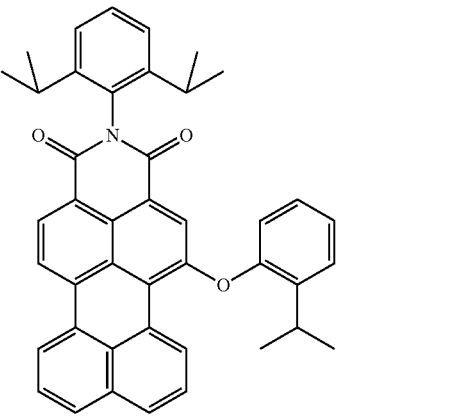
C-15
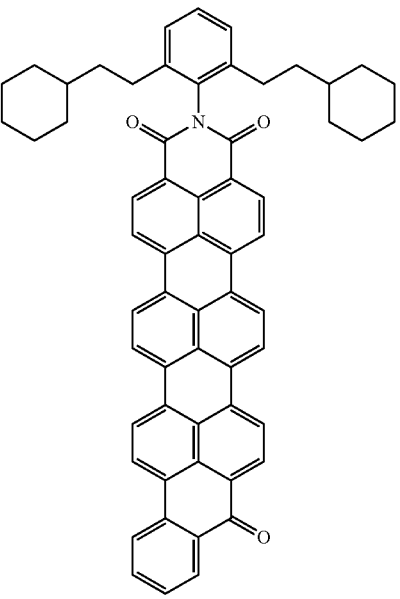

C-16
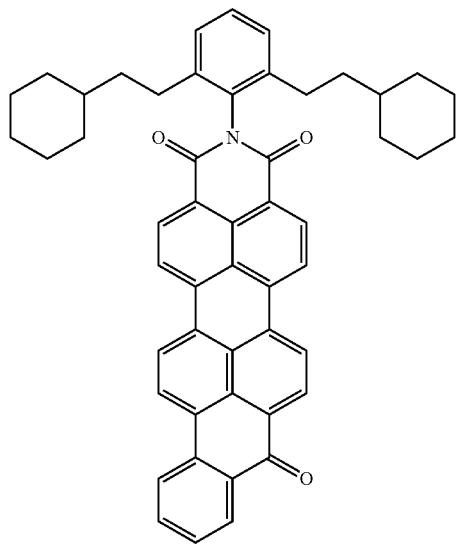
[Chem 25]
C-17
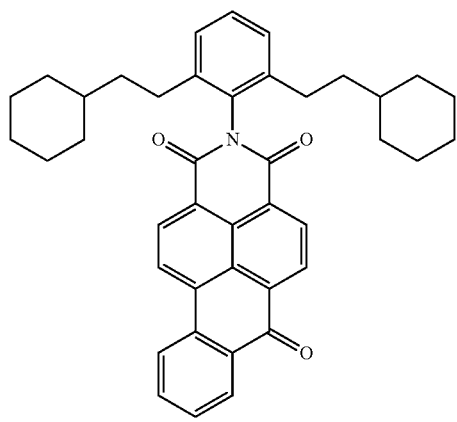
C-18
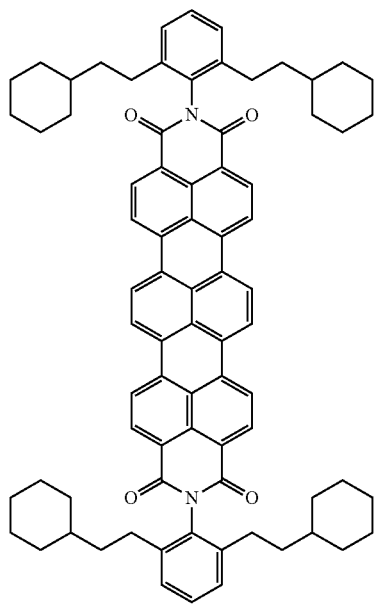
C-19
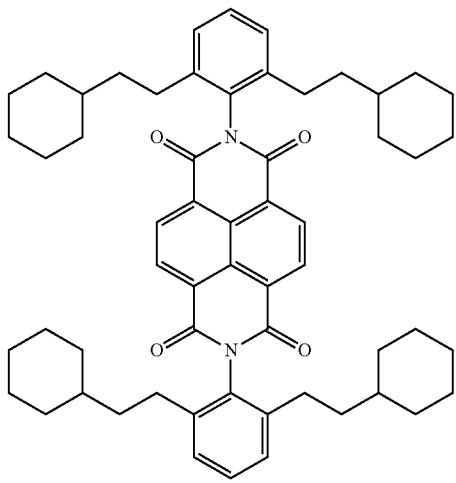
C-20
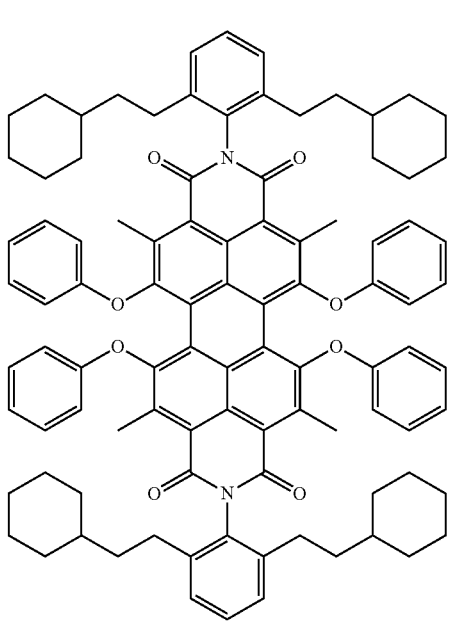

C-21
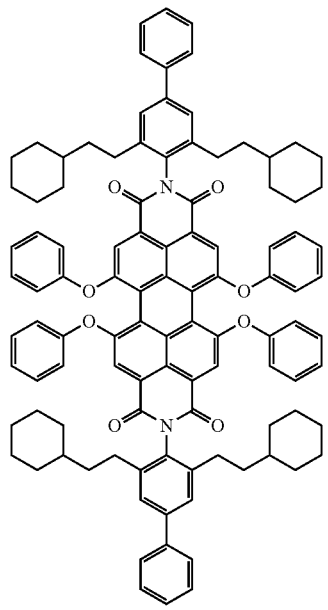
C-23
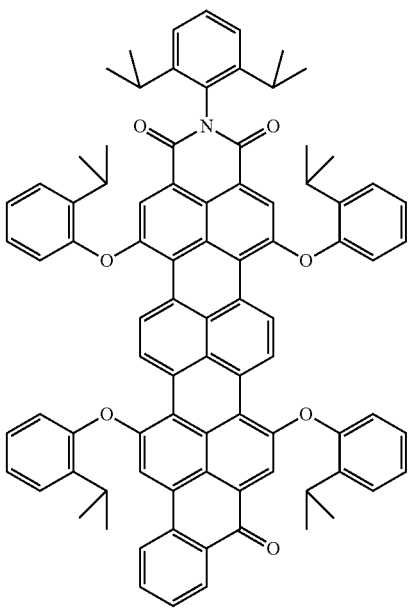
[Chem 26]
C-22
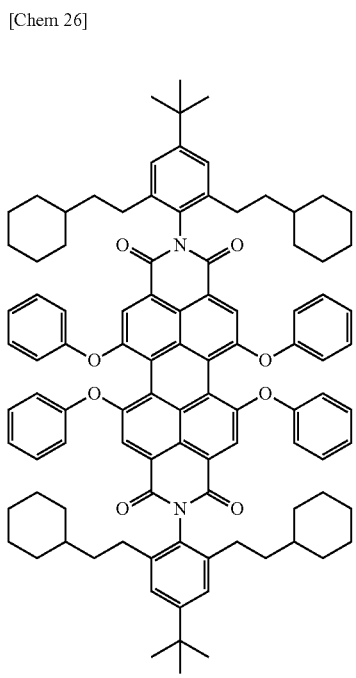
C-24
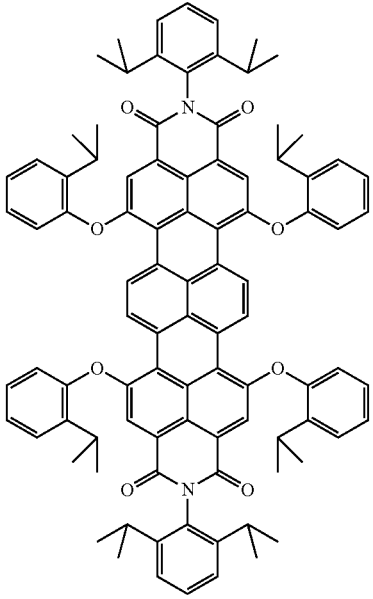

C-25
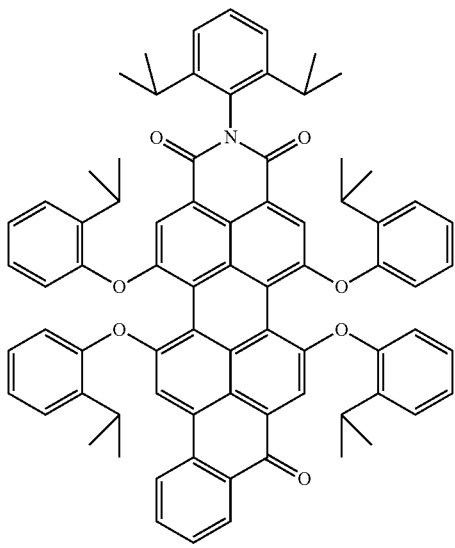
C-26
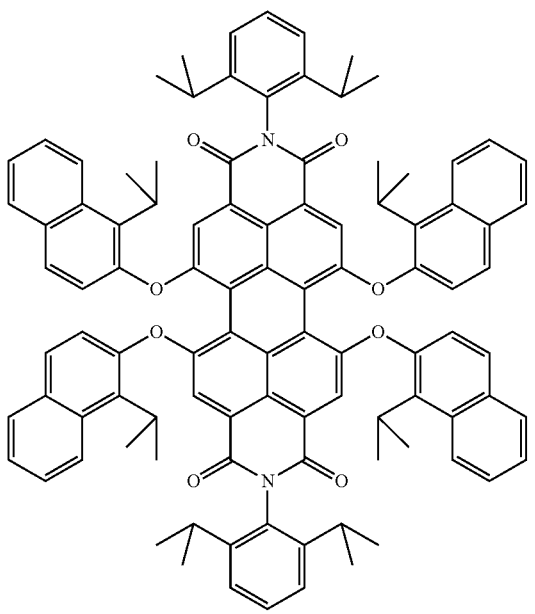
[Chem 27]
C-27
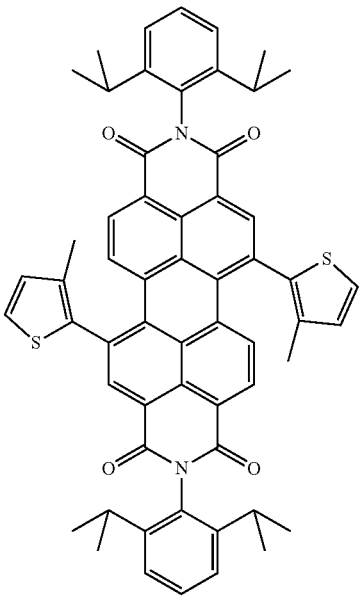
C-28
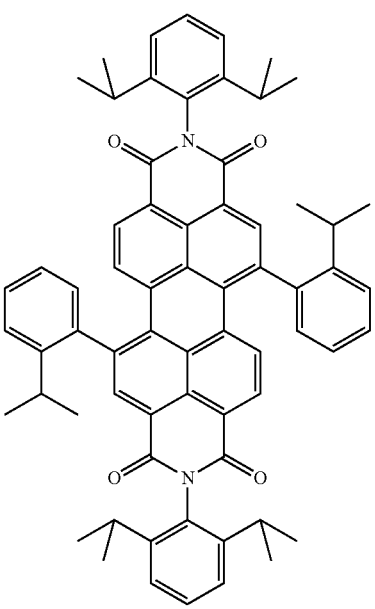

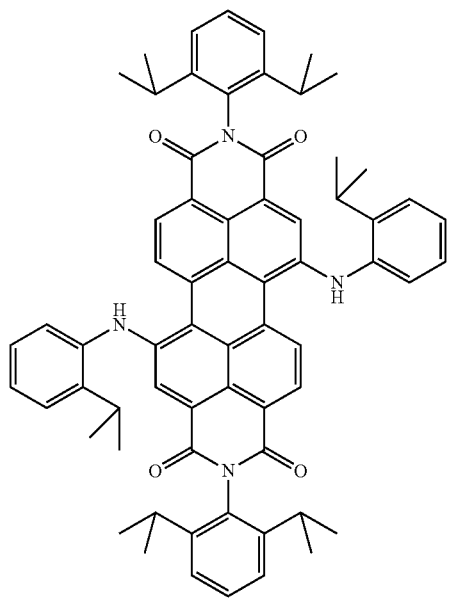
C-29
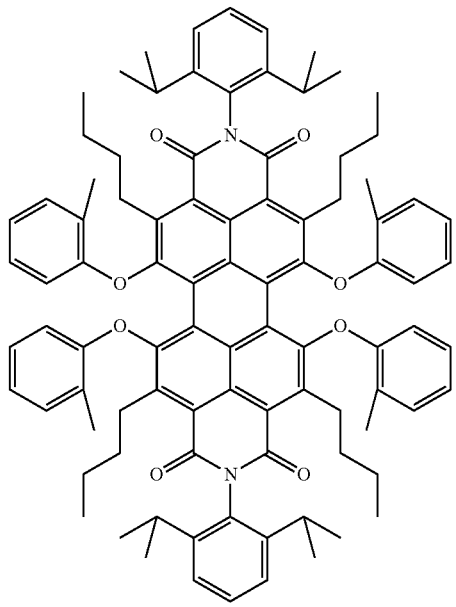
C-31
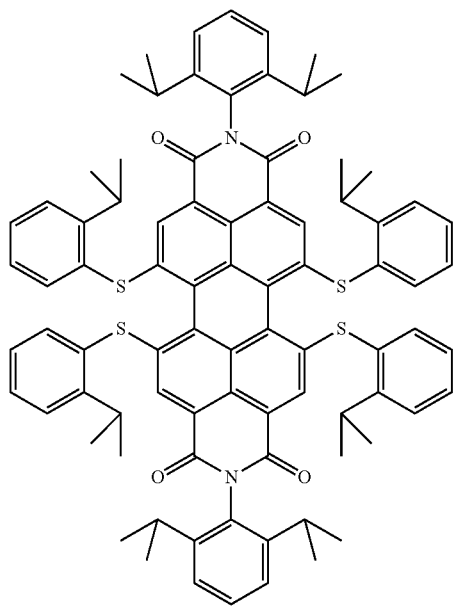
C-30
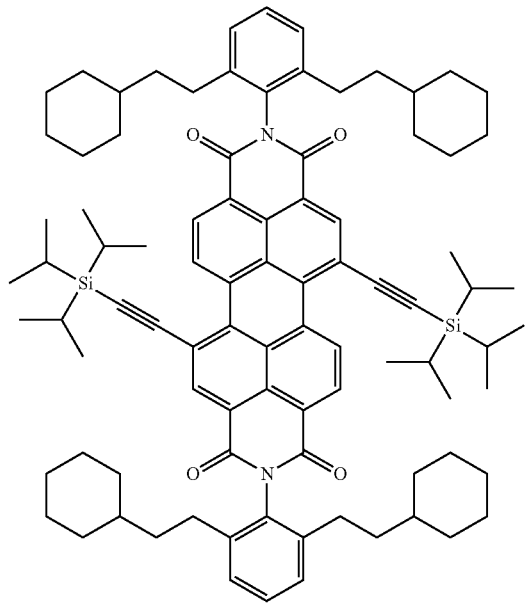
C-32

C-33
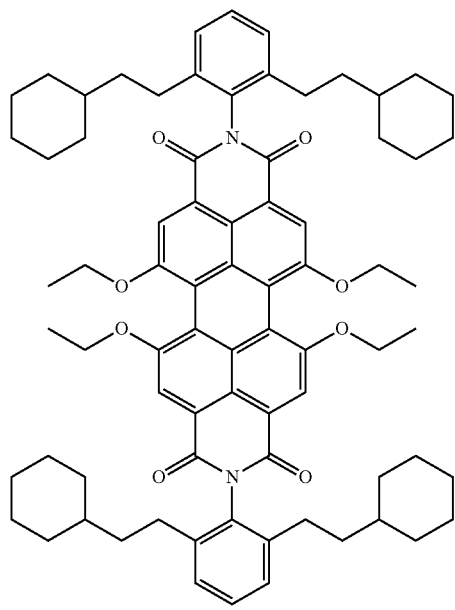
C-35
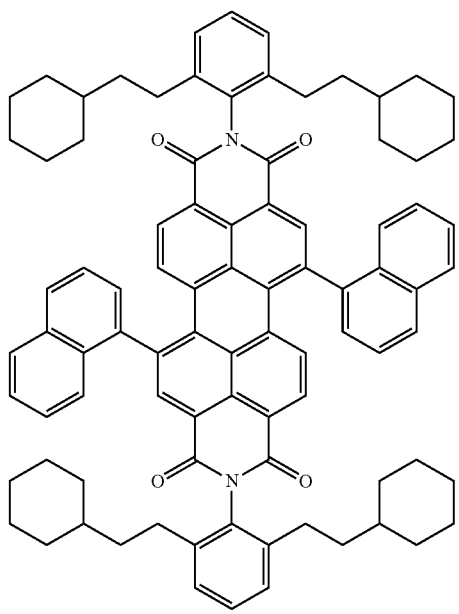
[Chem 28]
C-34
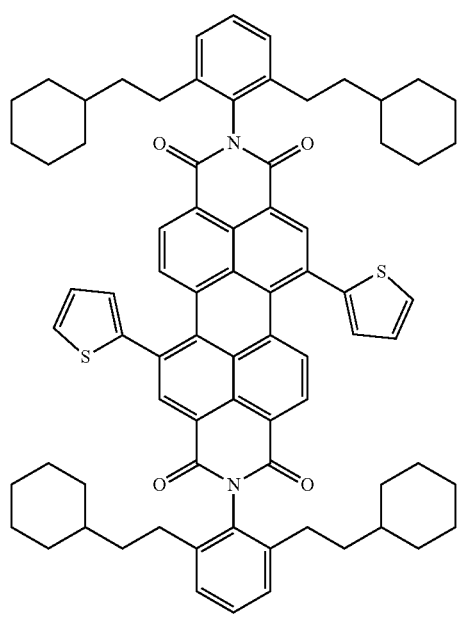
C-36
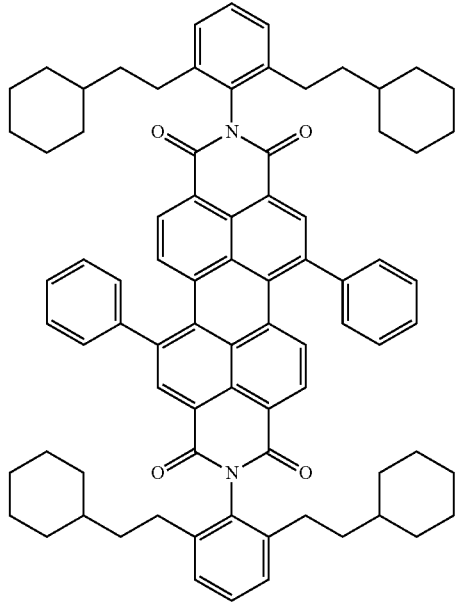

C-37
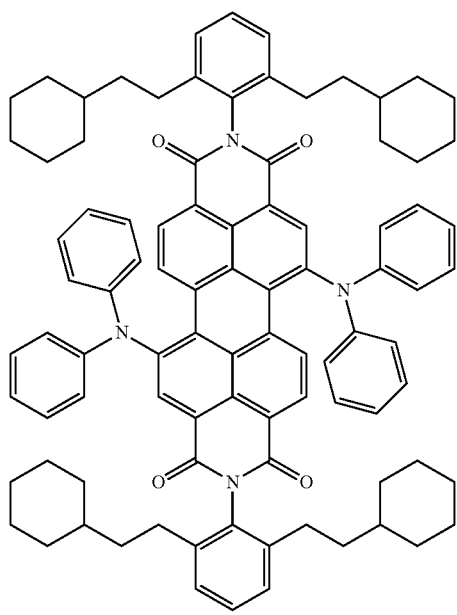
C-39
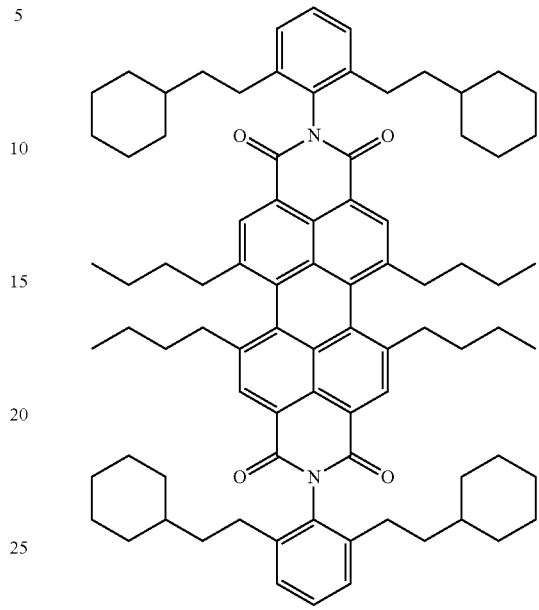
[Chem 29]
C-38
C-40
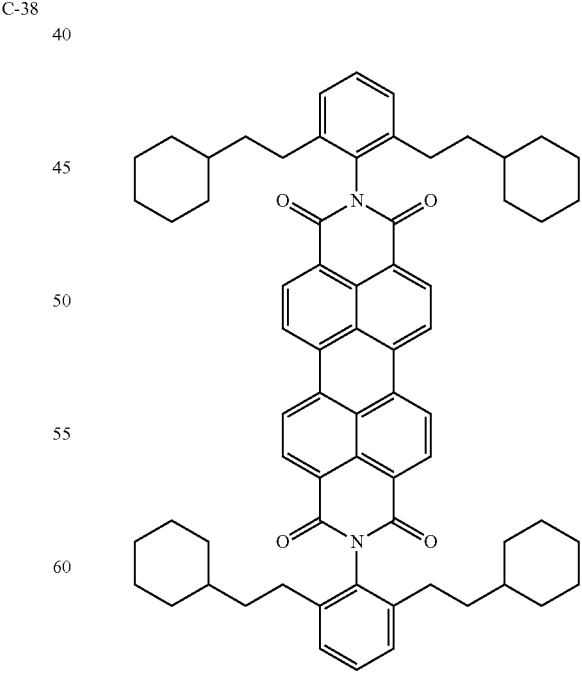

C-41
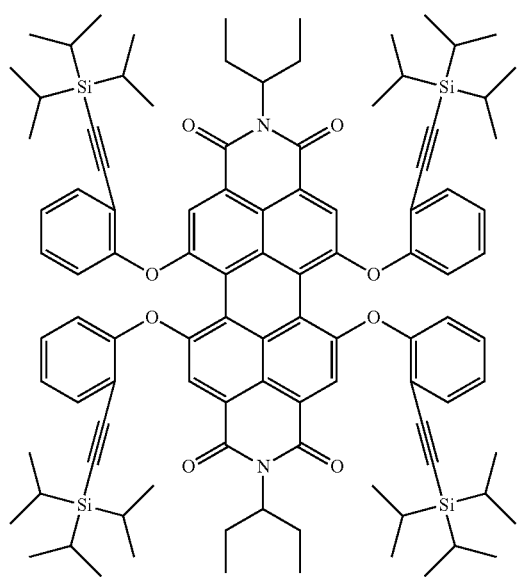
C-43
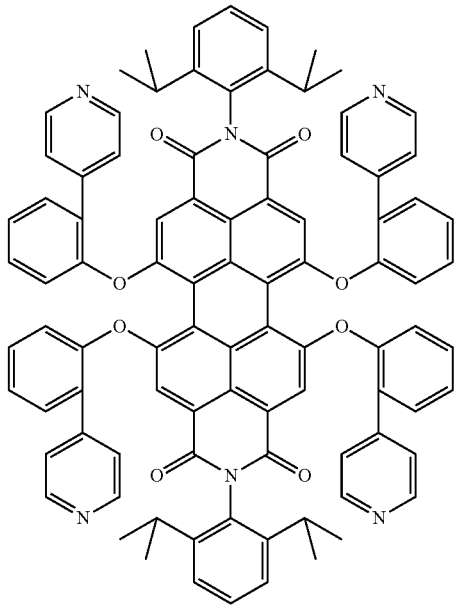
C-42
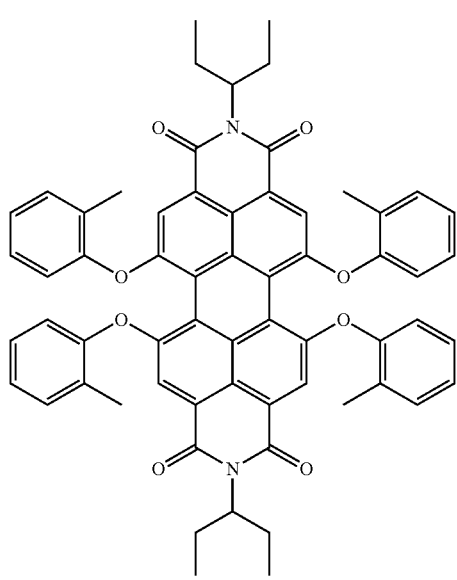
C-44
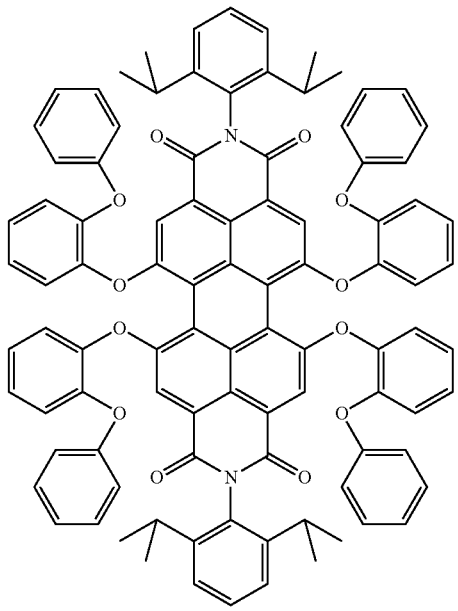

[Chem 30]
C-45
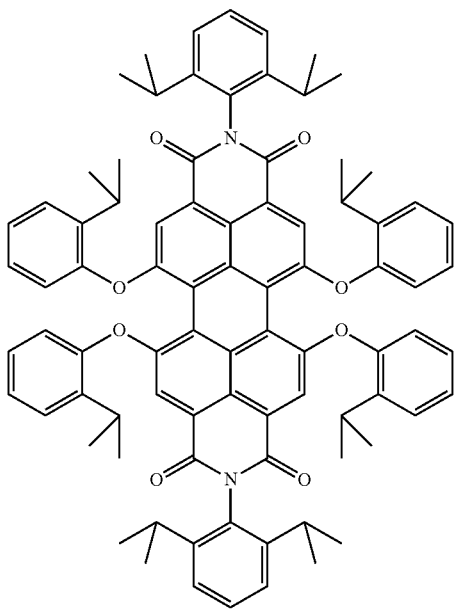
C-46
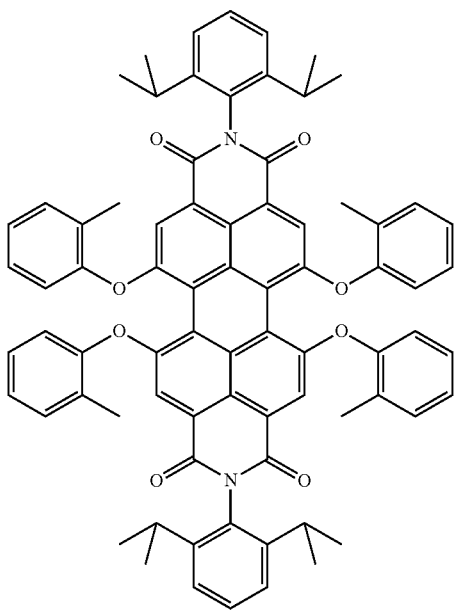
C-47
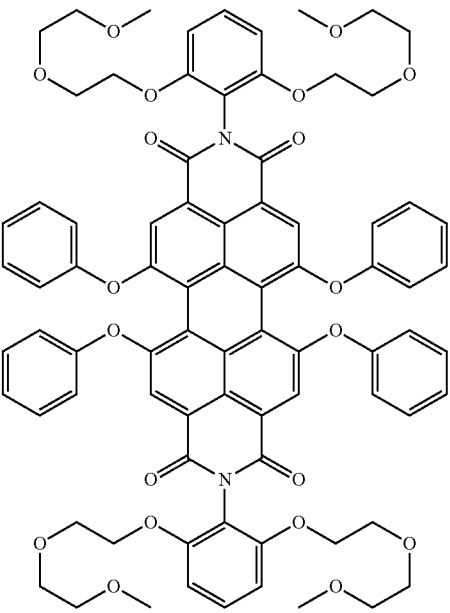
C-48
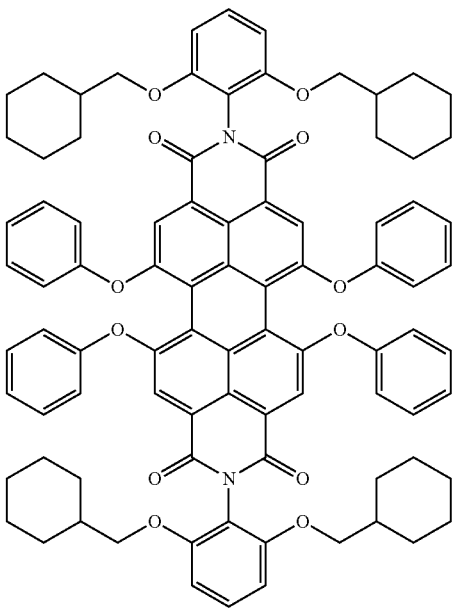

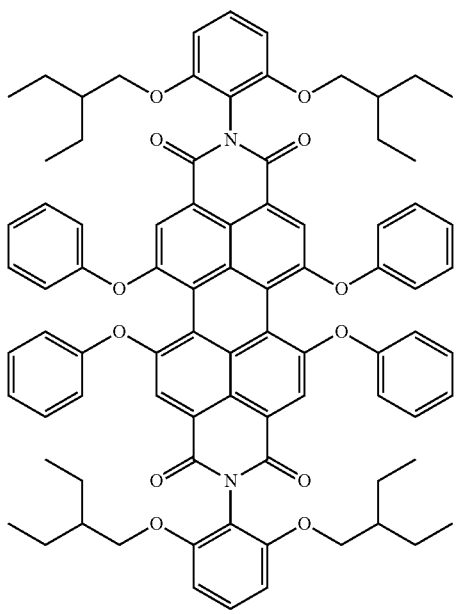
C-49
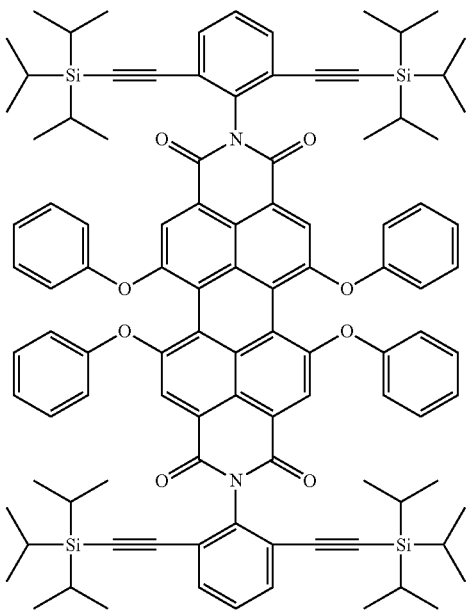
[Chem 31]
C-51
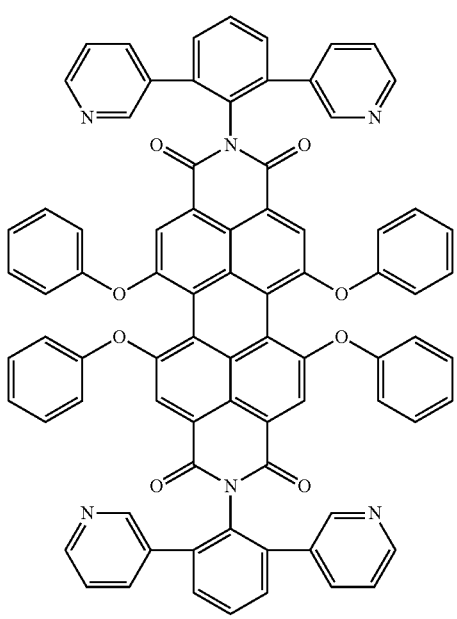
C-50
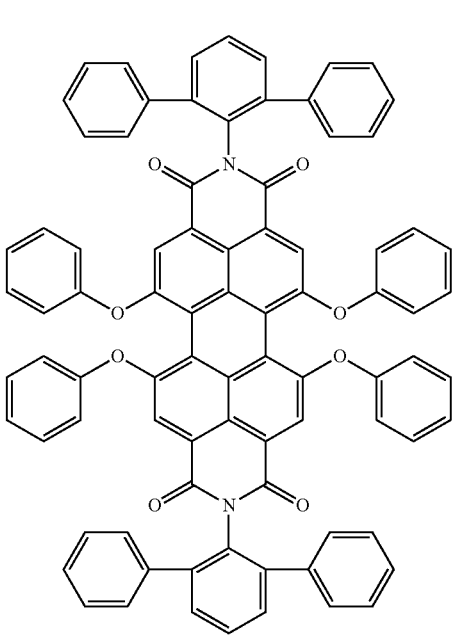
C-52

C-53
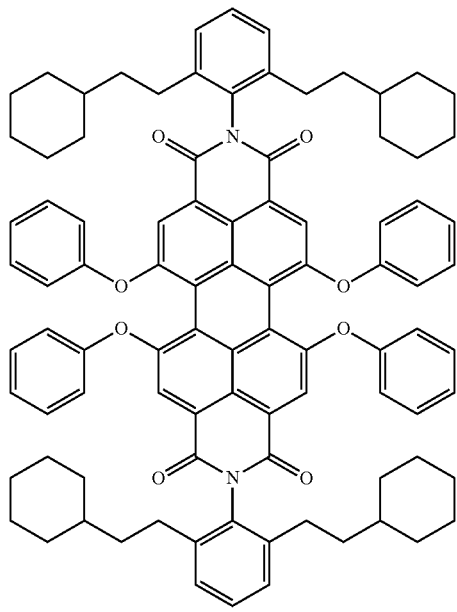
C-54
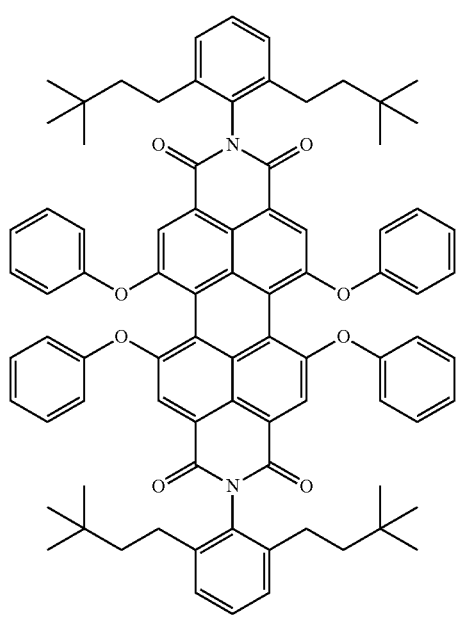
C-55
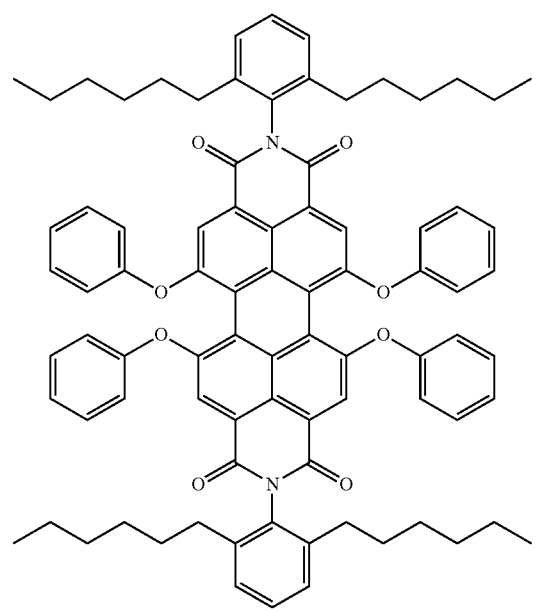
[Chem 32]
C-56
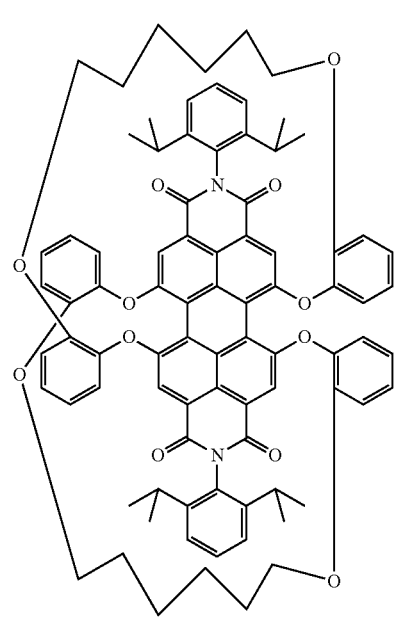

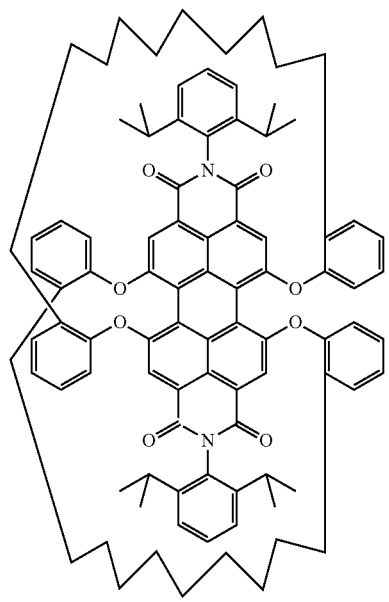
C-57
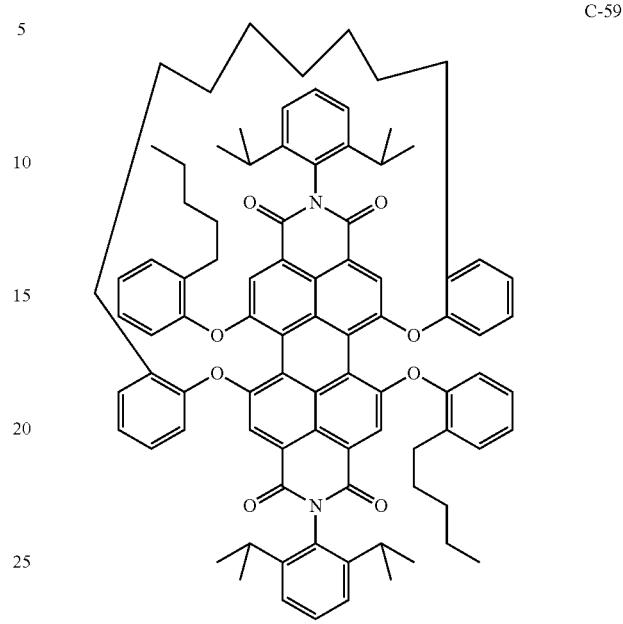
C-59
[Chem 33]
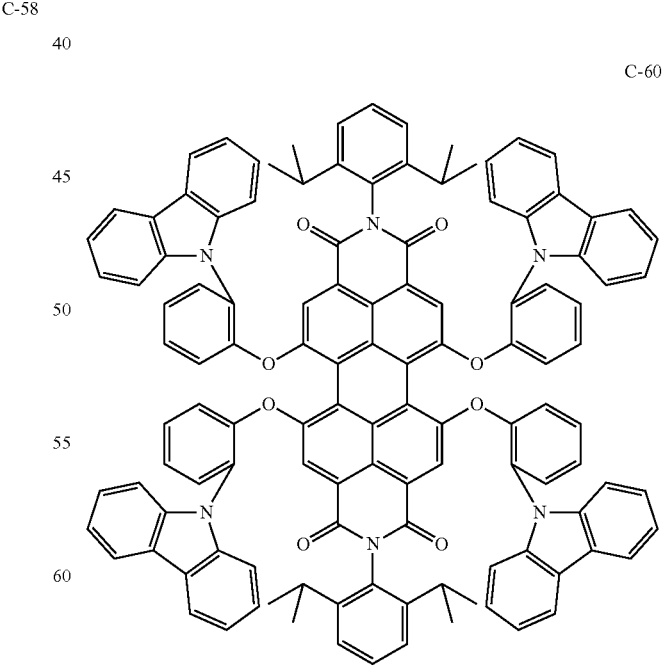
C-58
C-60

C-61
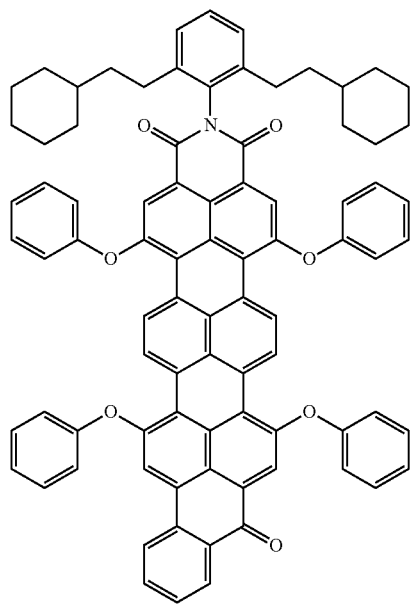
C-62
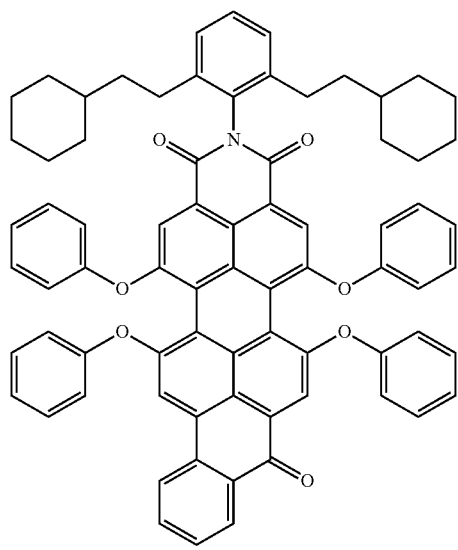
C-63
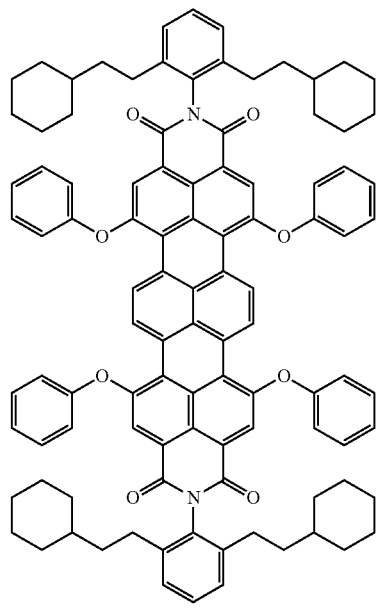
C-64
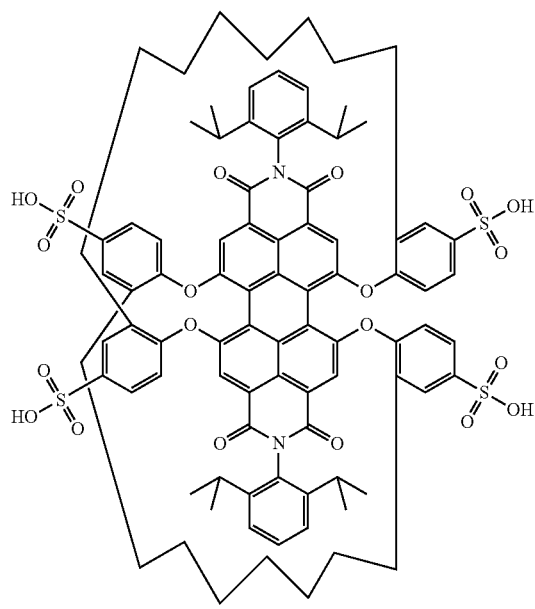

C-65
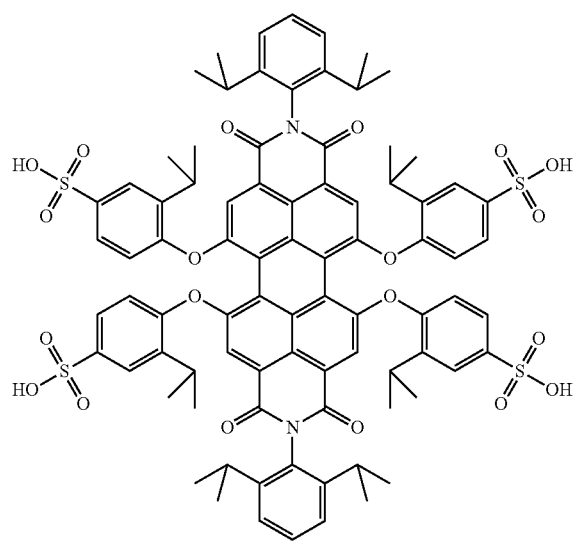
C-67
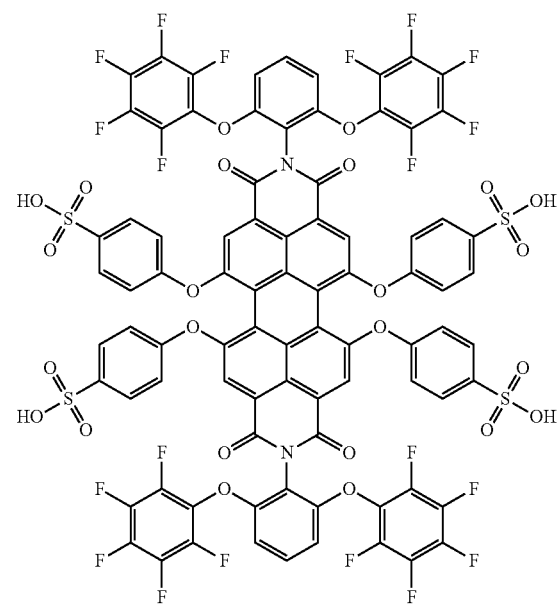
[Chem 35]
C-66
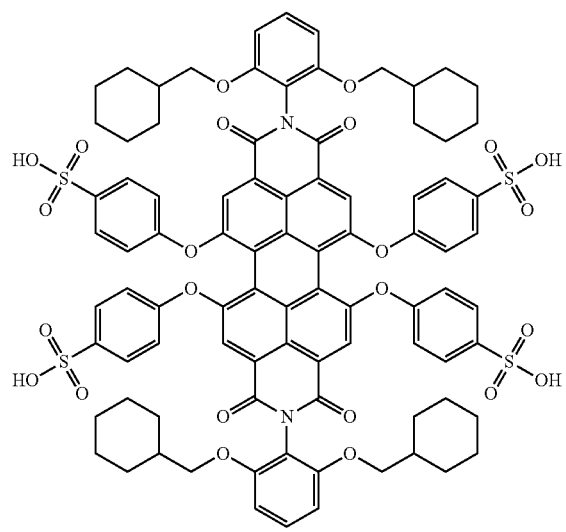
C-68

[Chem 36]
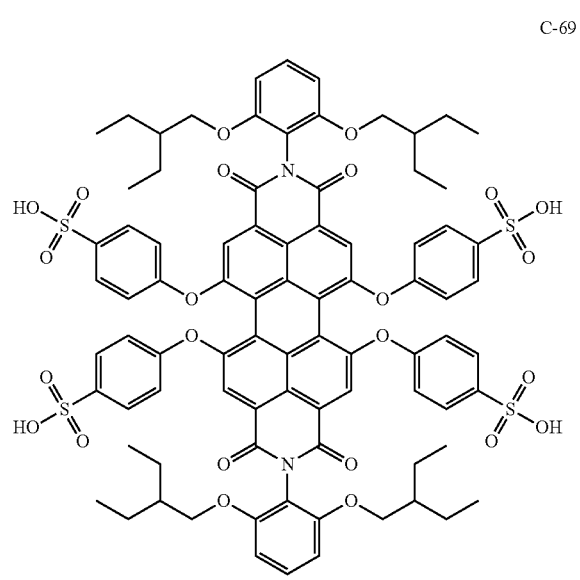
C-69
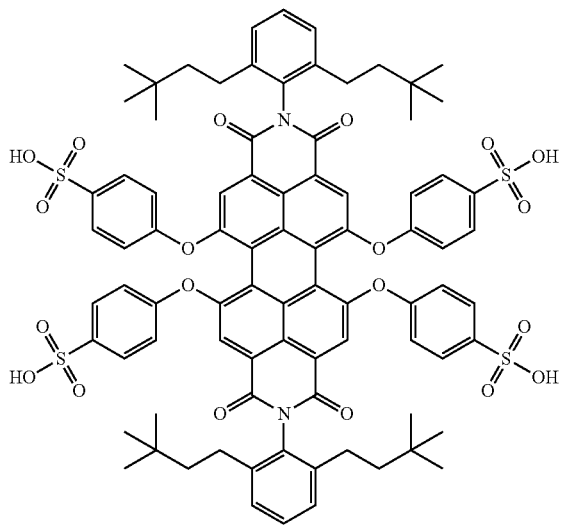
C-71
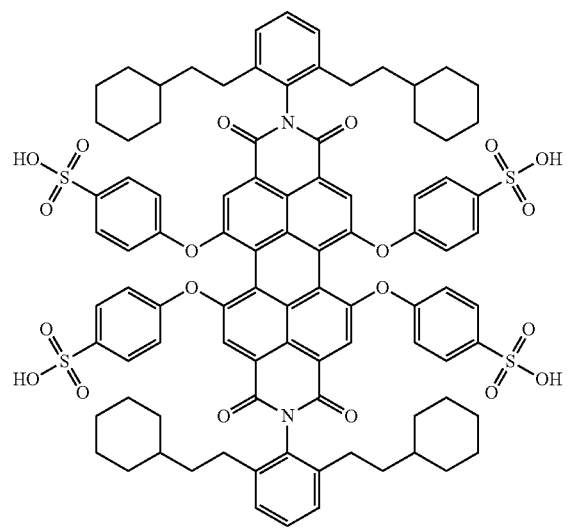
C-70
[Chem 37]
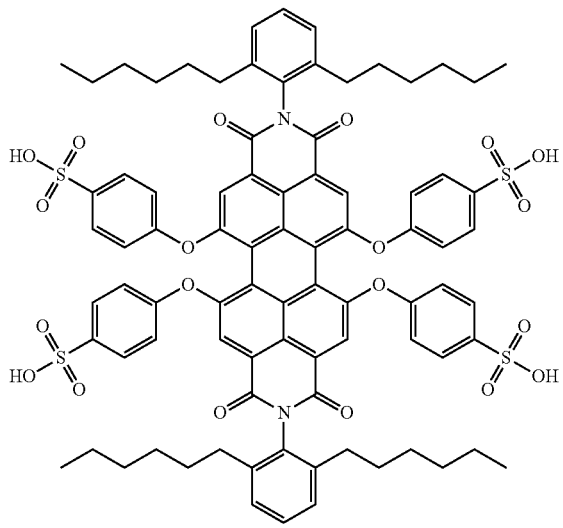
C-72

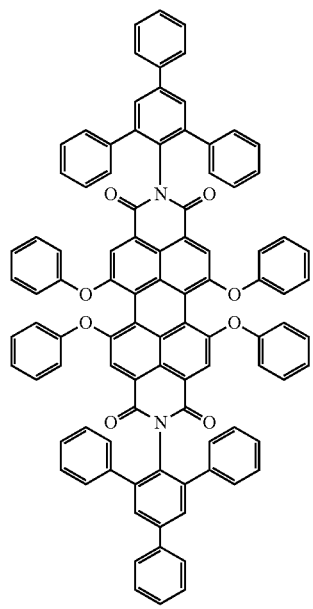
C-73
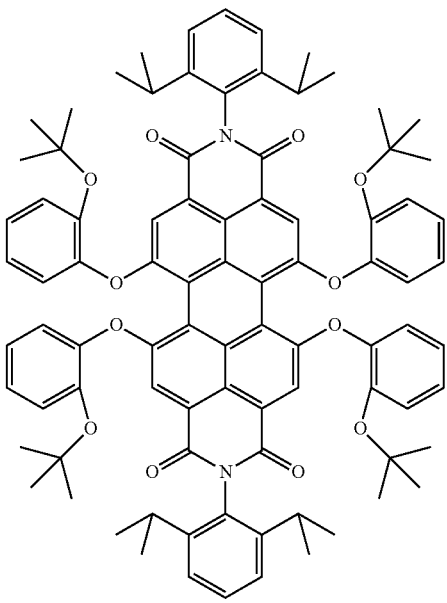
C-75
[Chem 38]
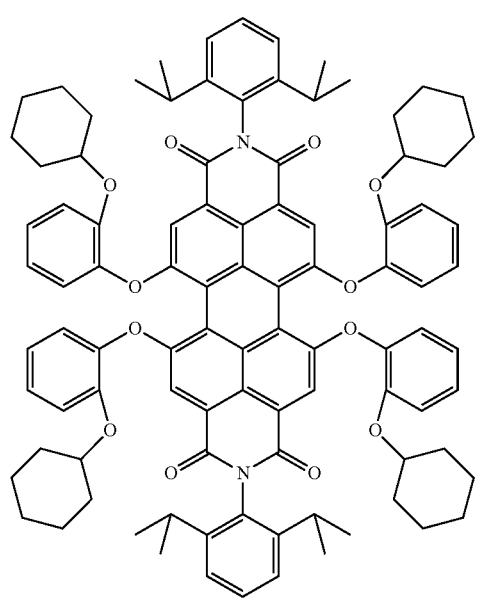
C-74
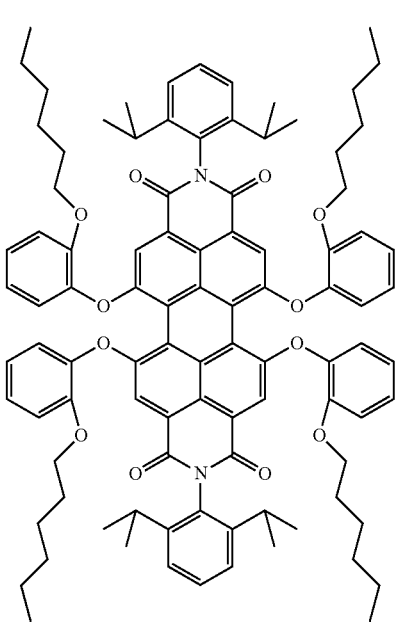
C-76

-continued
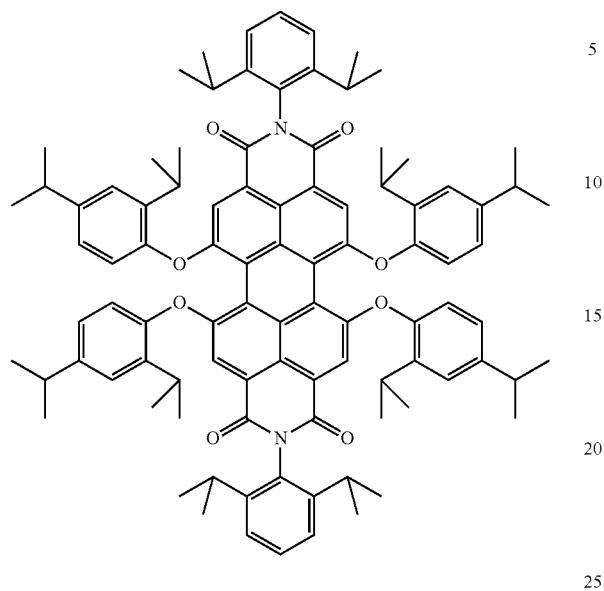
C-77
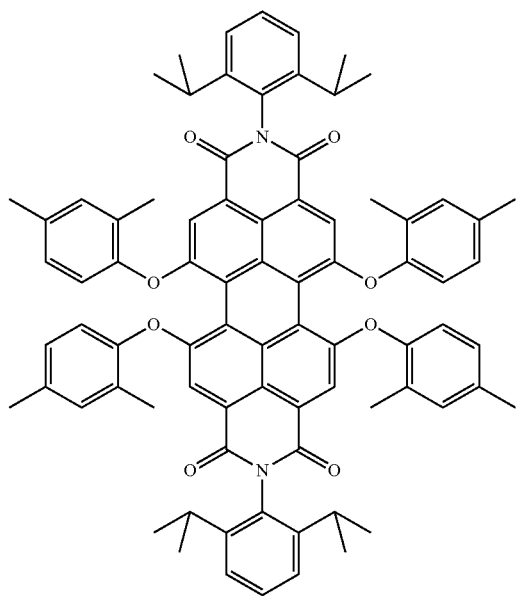
C-79
[Chem 39]
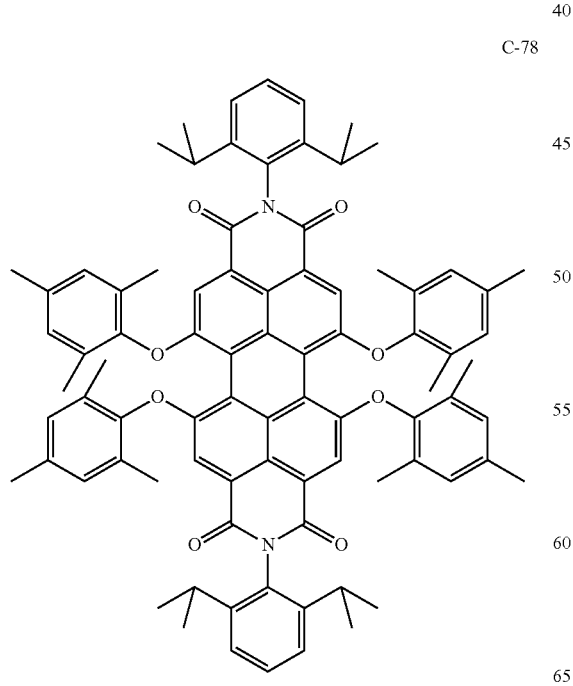
C-78
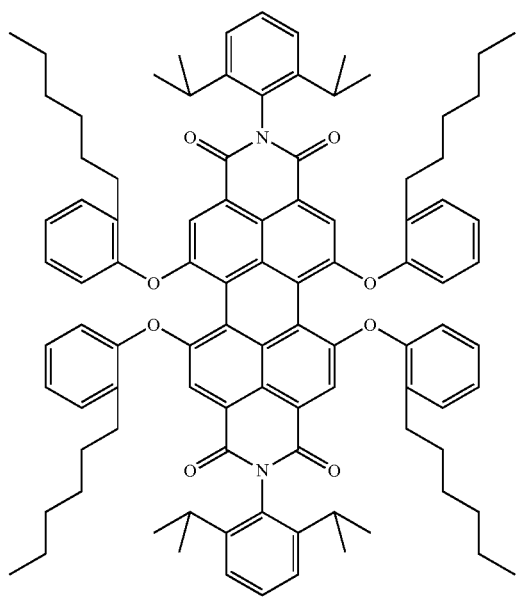
C-81

C-81
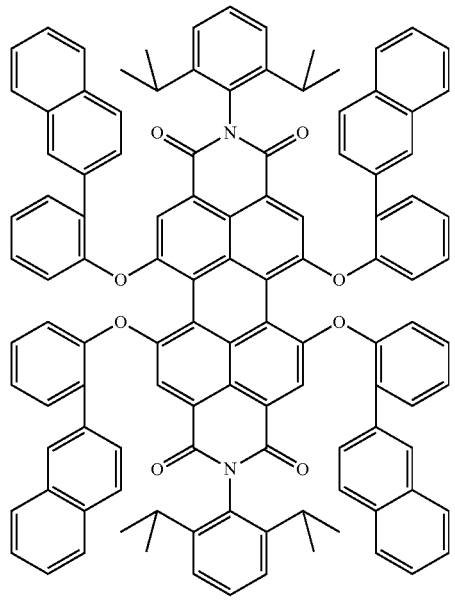
C-83
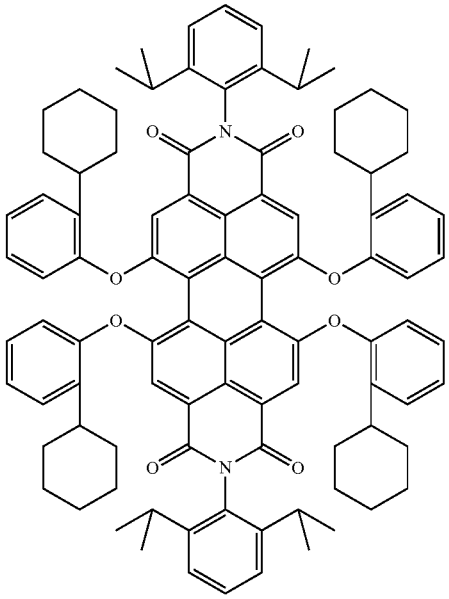
C-82
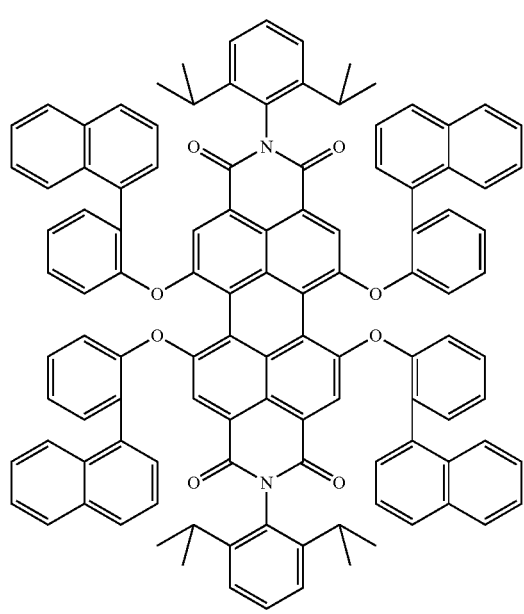
C-84
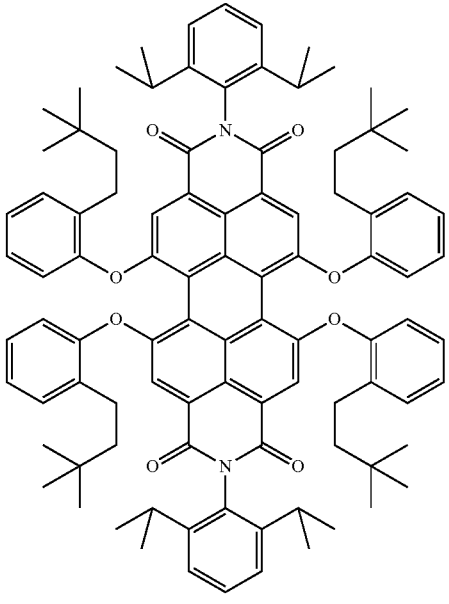

C-85
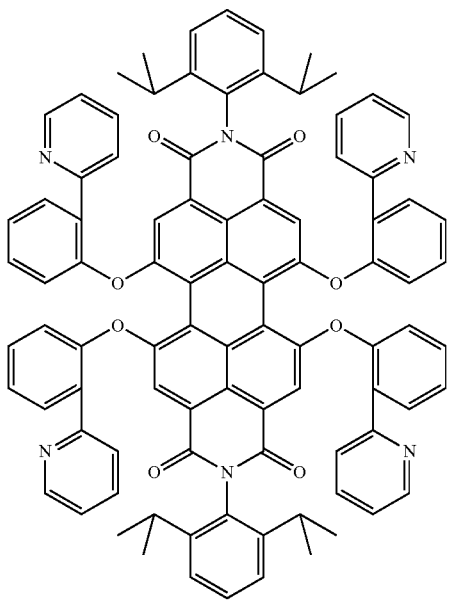
C-86
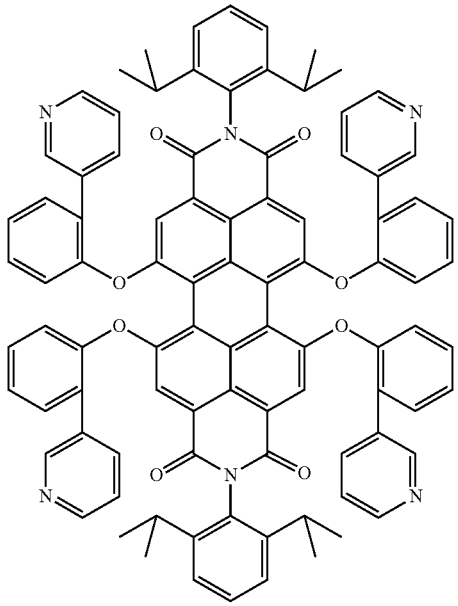
C-87
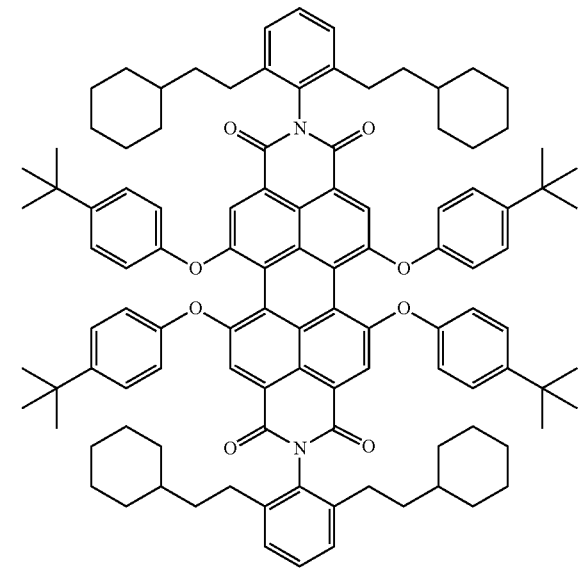
C-88
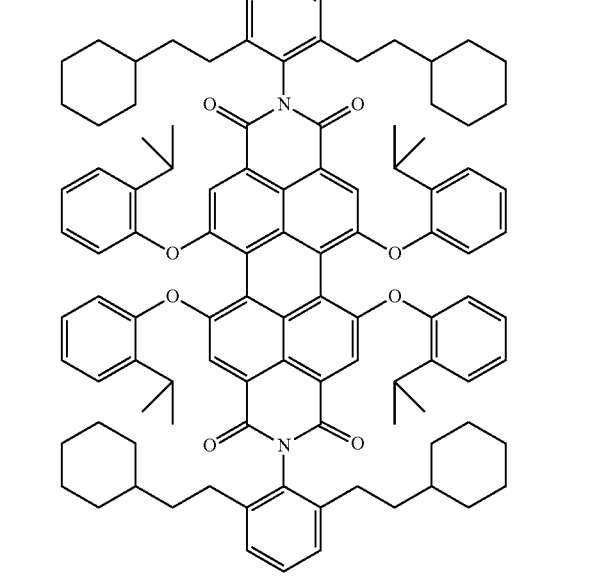

C-89
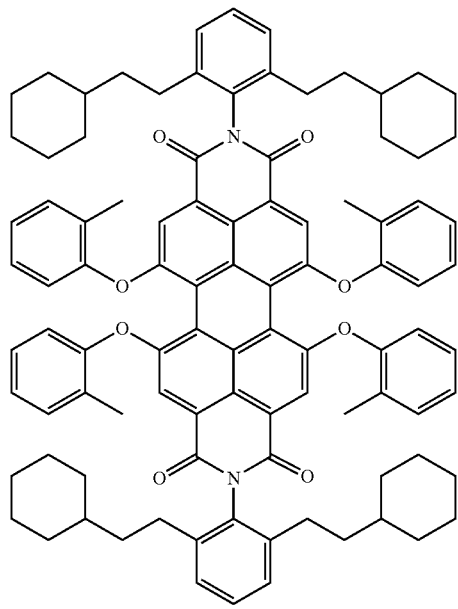
C-90
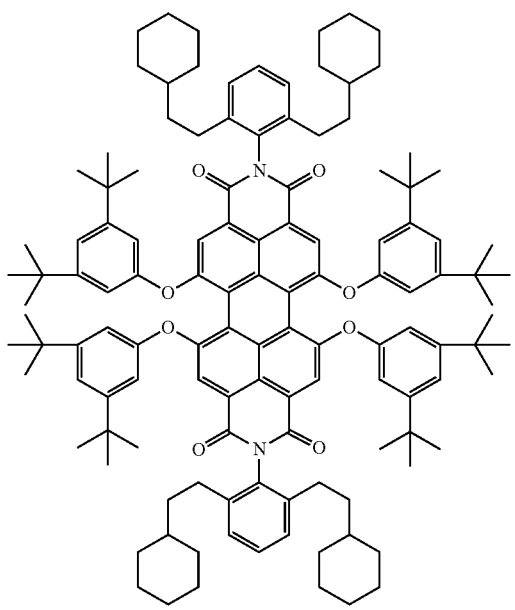
C-91
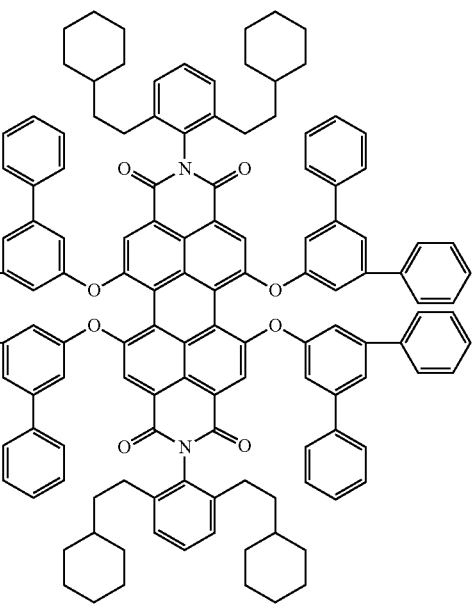
C-92

[Chem 42]
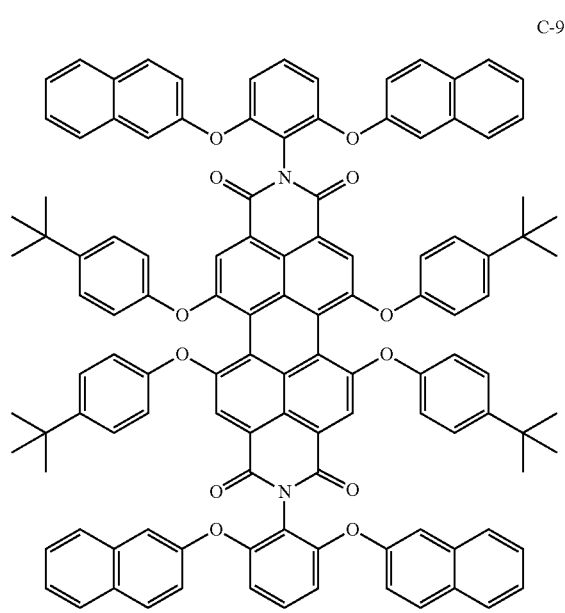
C-93
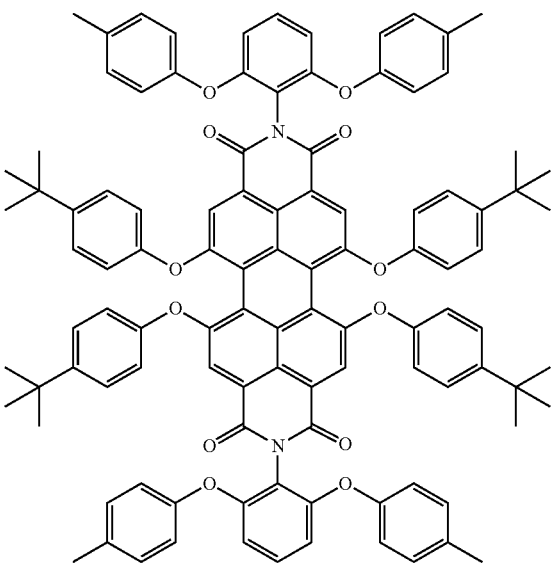
C-95
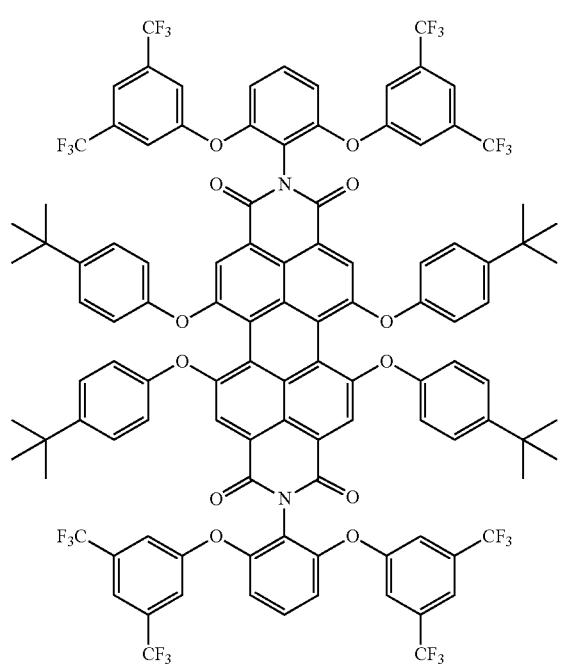
C-94
[Chem 43]
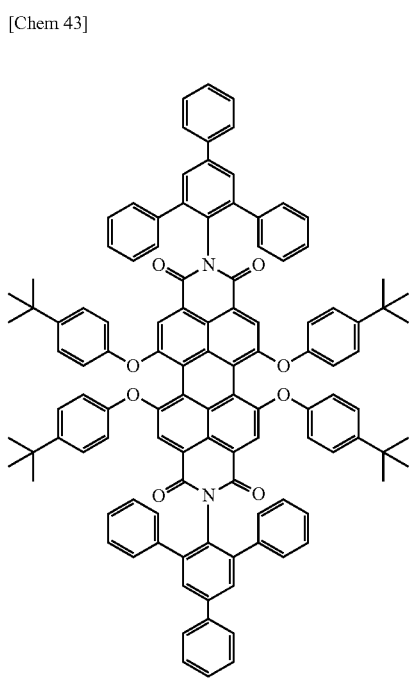
C-96

C-97
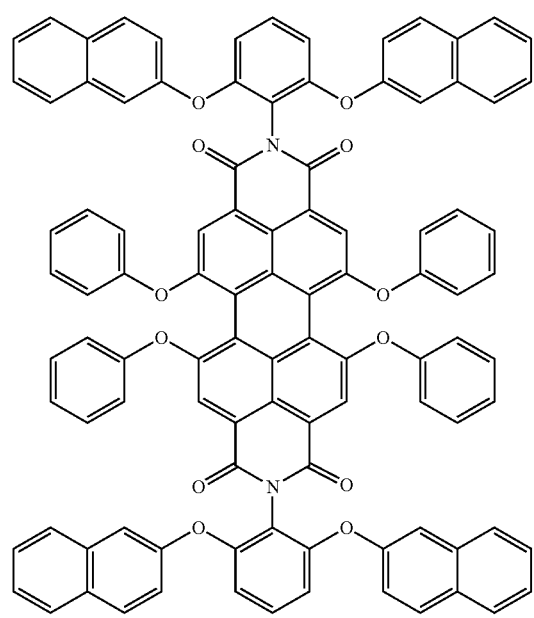
C-98
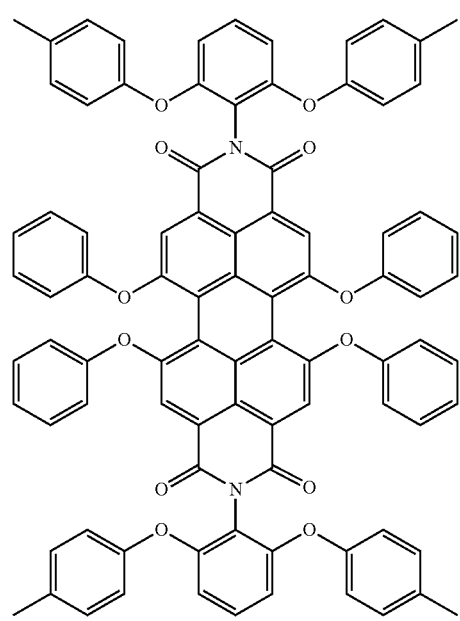
C-99
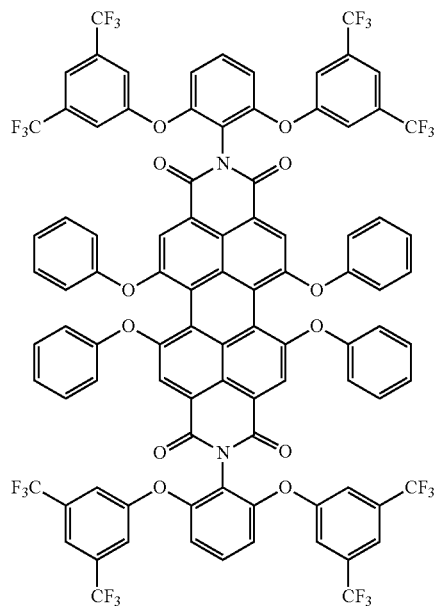
[Chem 44]
C-100
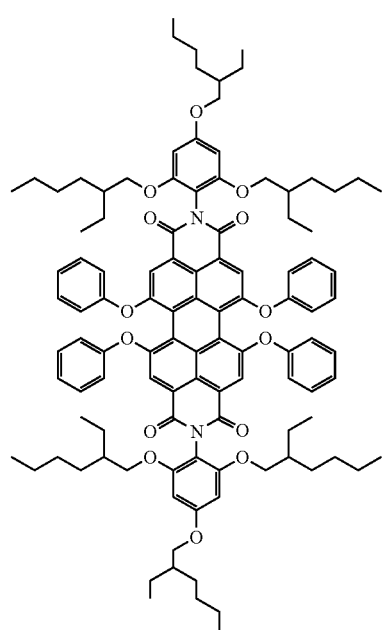

C-101
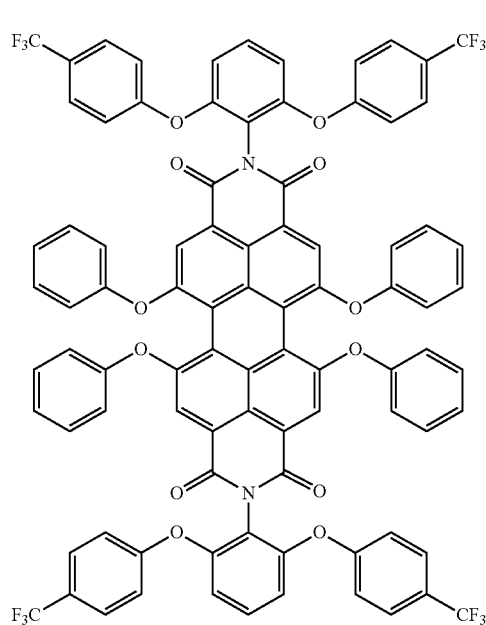
C-103
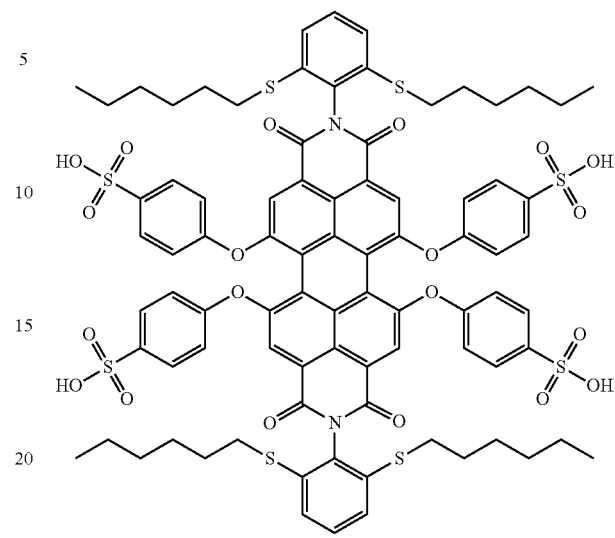
C-102
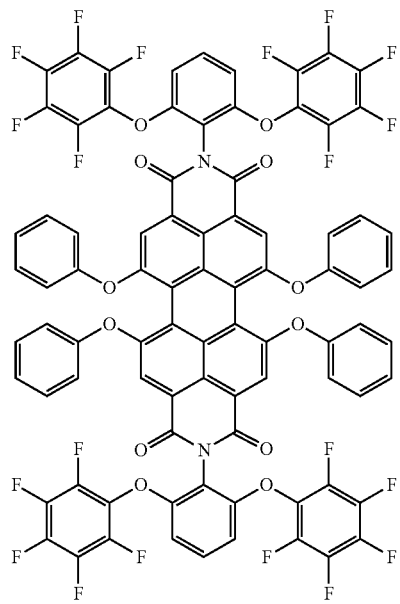
[Chem 45]
C-104
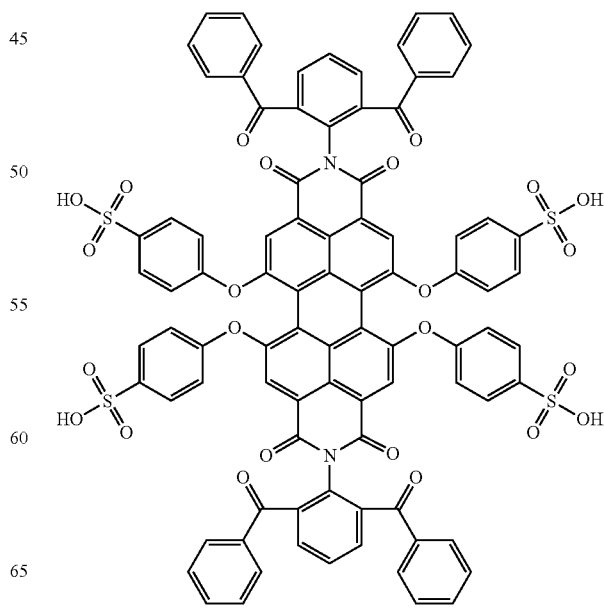

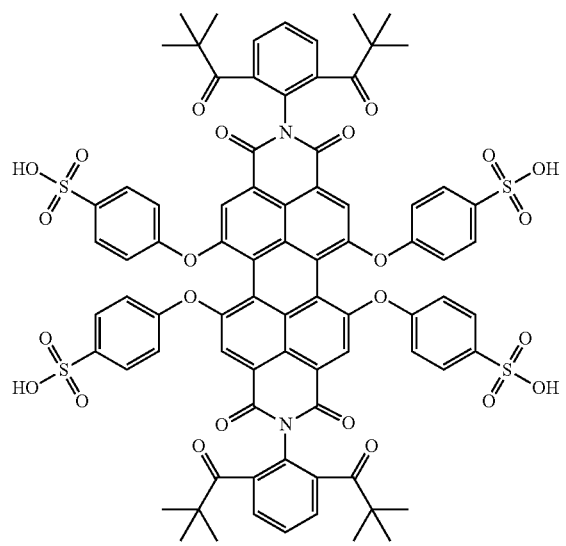
C-105
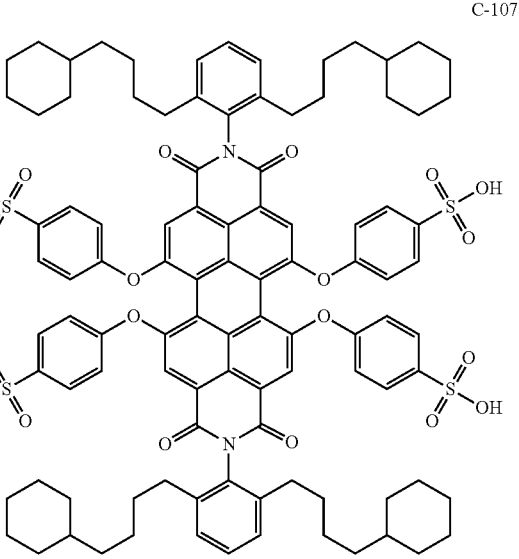
C-107
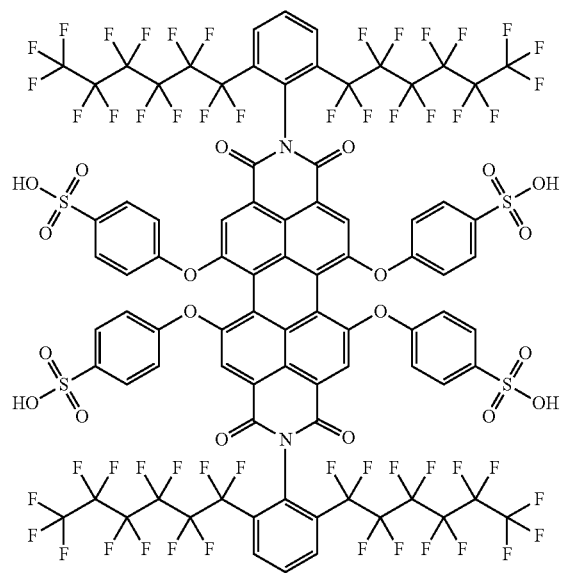
C-106
C-108

[Chem 47]
C-109
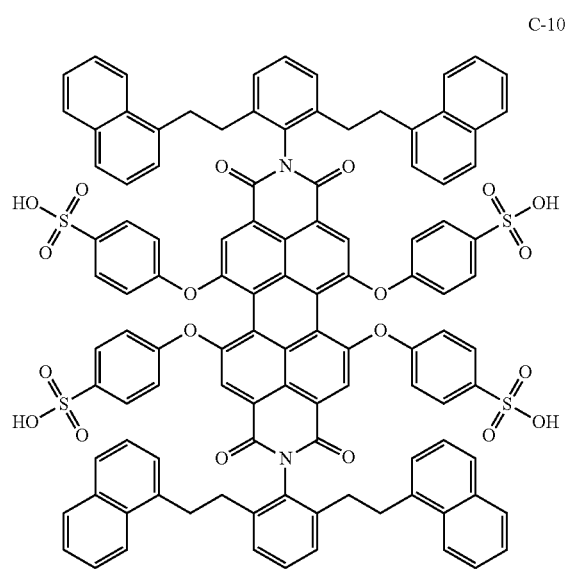
C-111
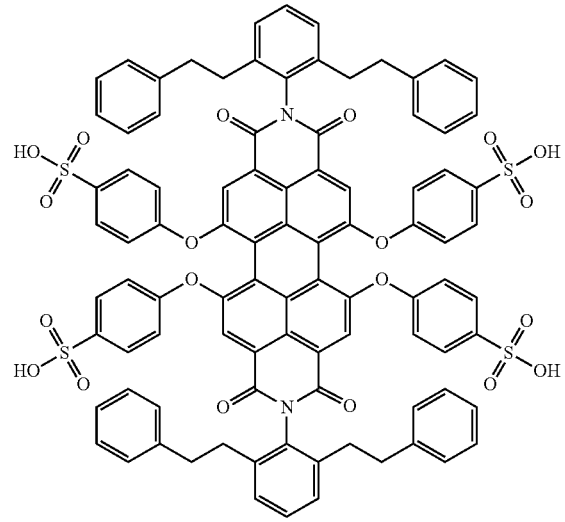
C-110
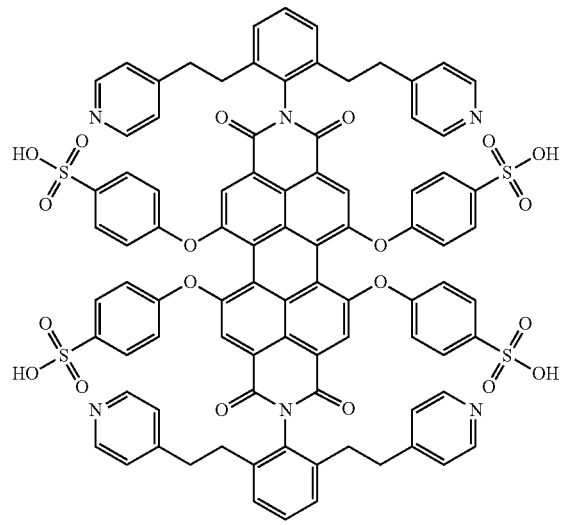
[Chem 48]
C-112
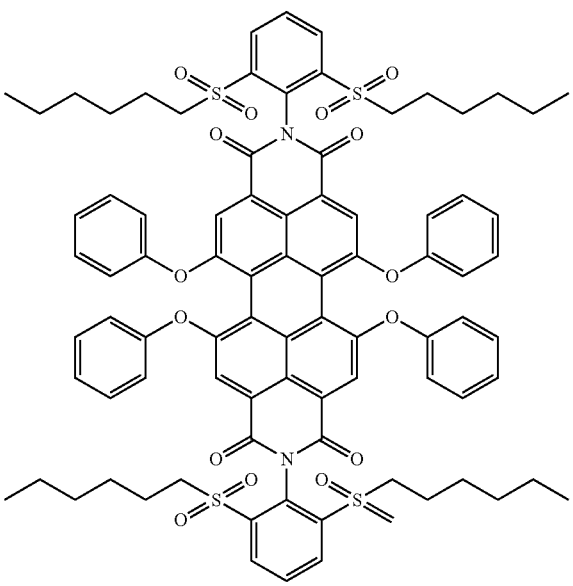

C-113
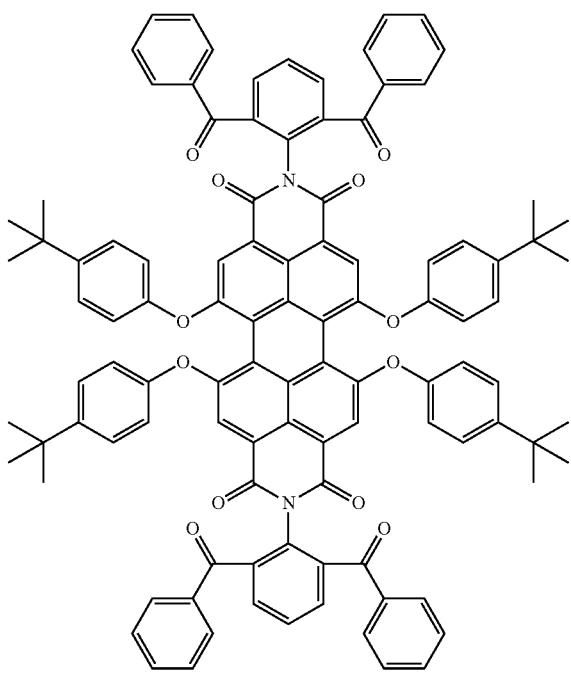
[Chem 49]
C-115
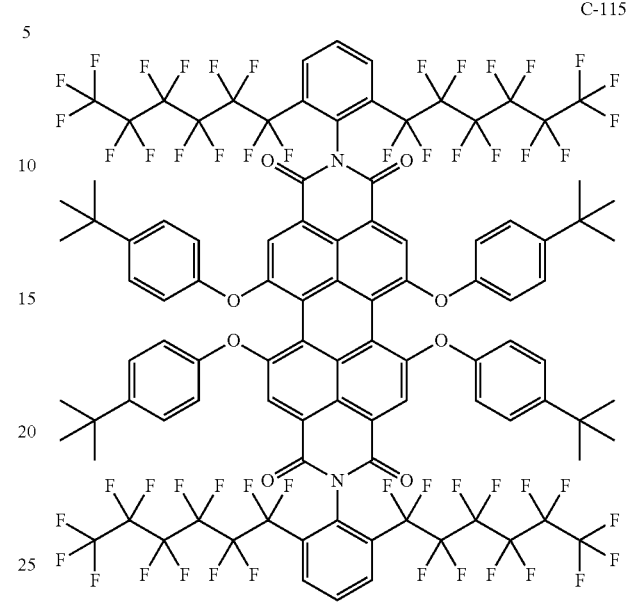
C-114
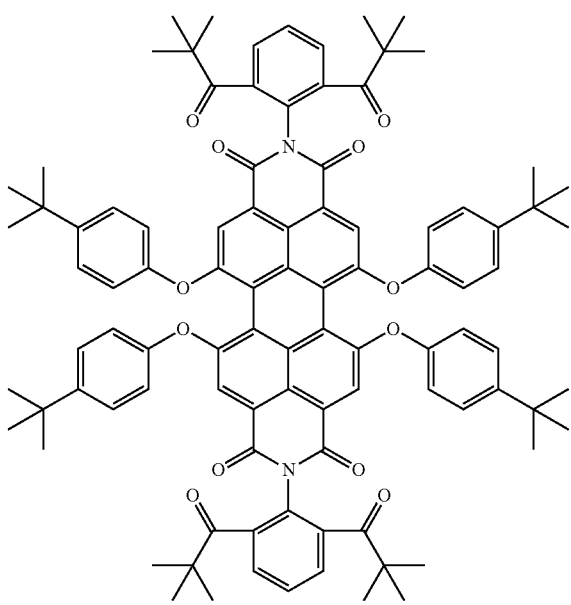
C-116
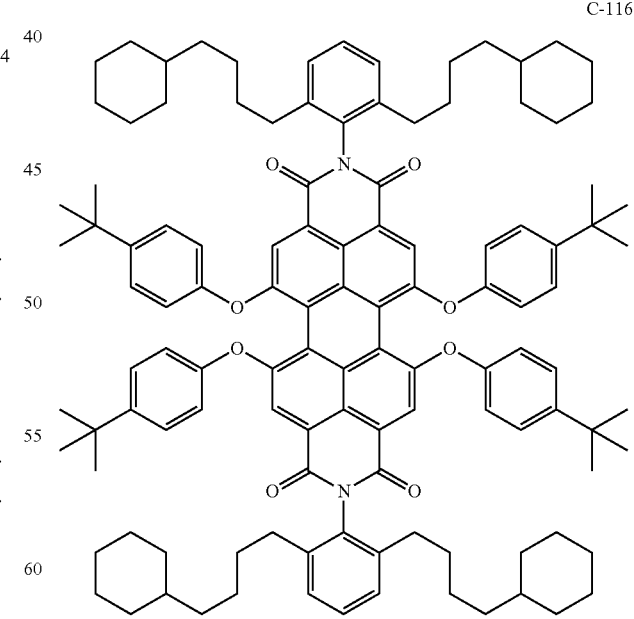

C-117
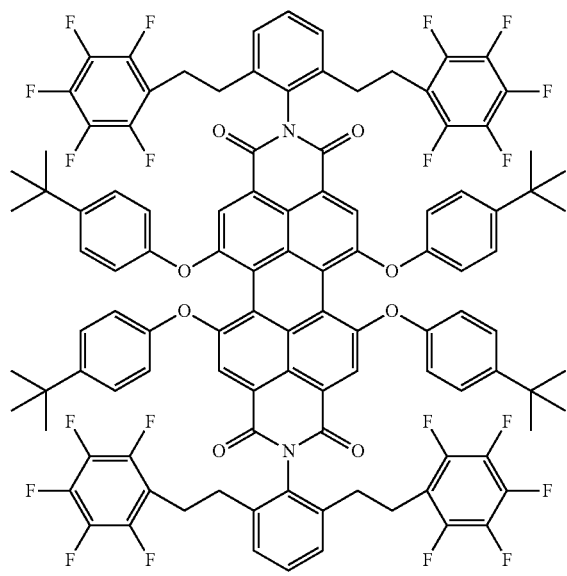
C-119
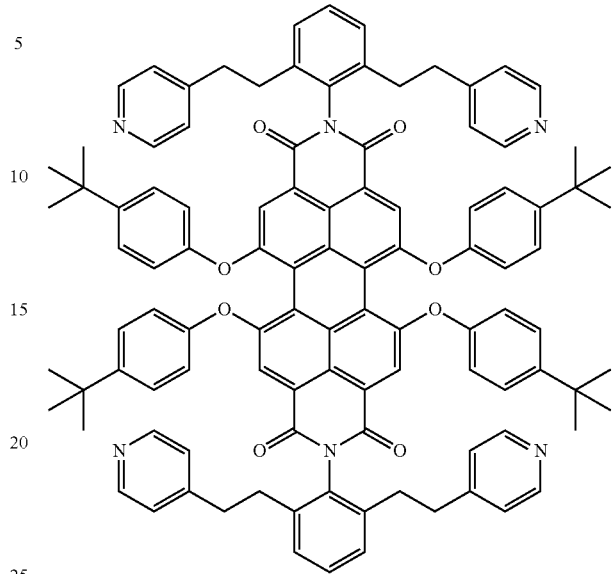
[Chem 50]
C-118
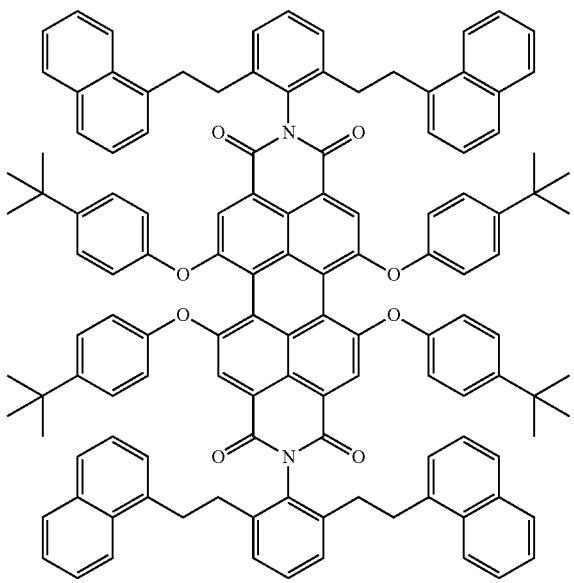
C-120
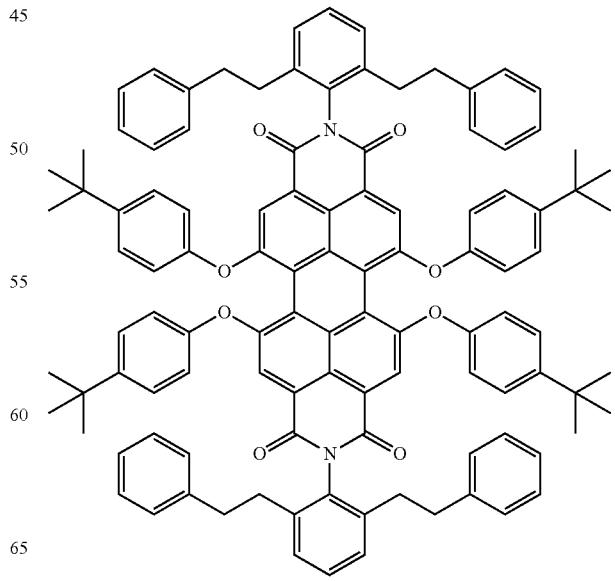

-continued
C-121
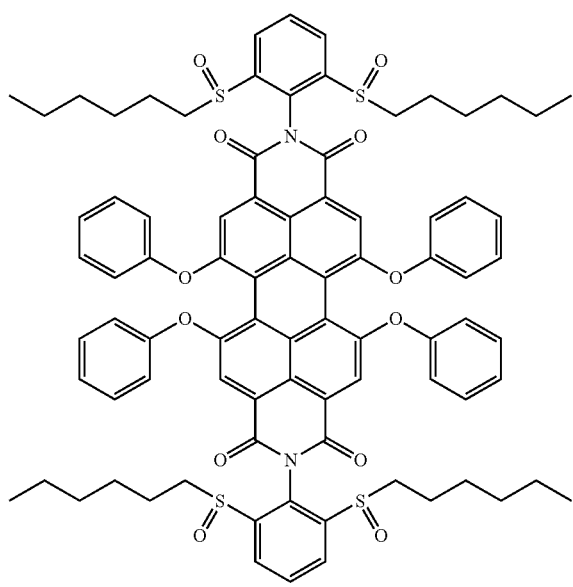
[Chem 51]
C-122
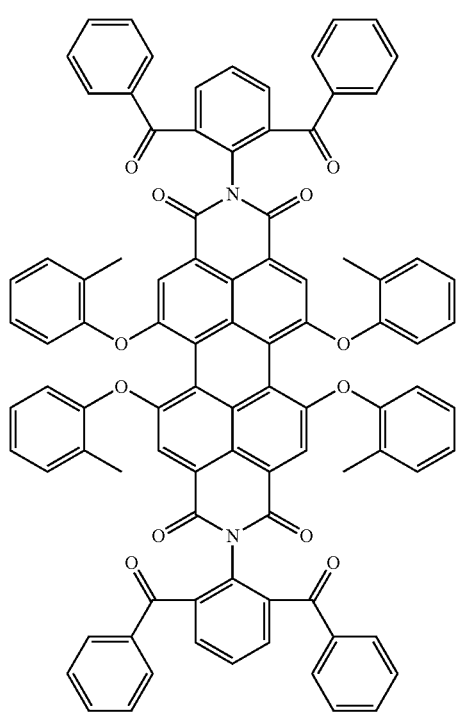
-continued
C-123
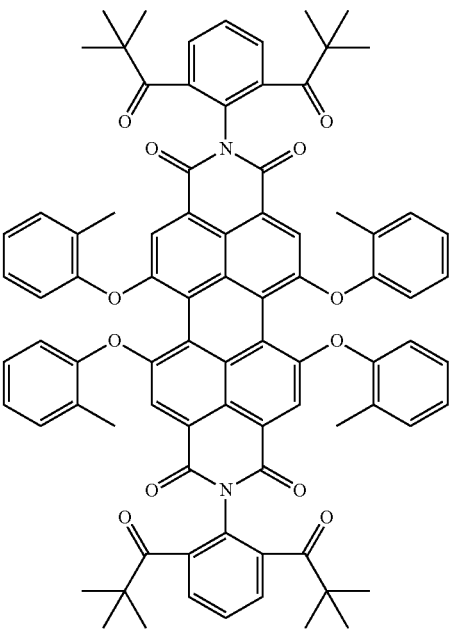
C-124
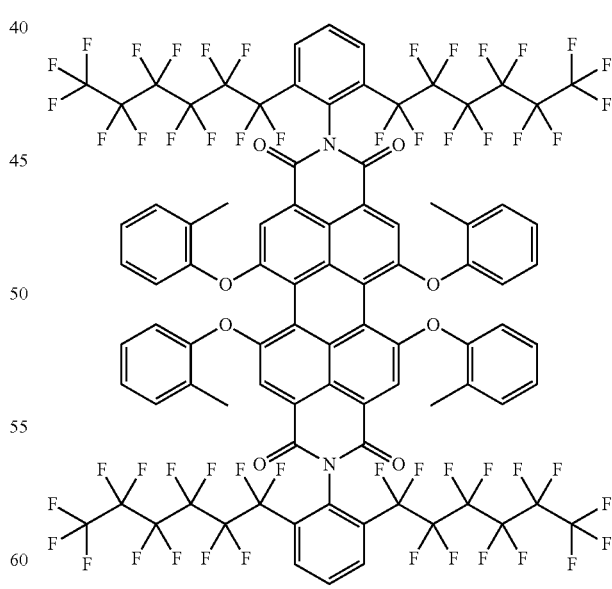

C-125
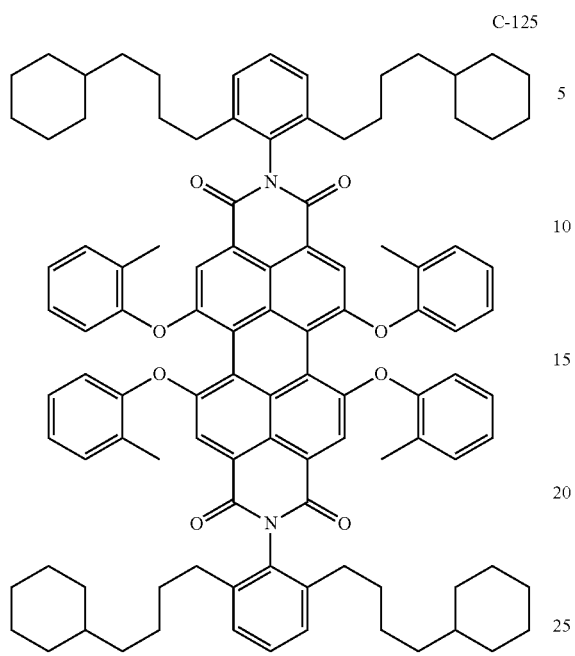
C-127
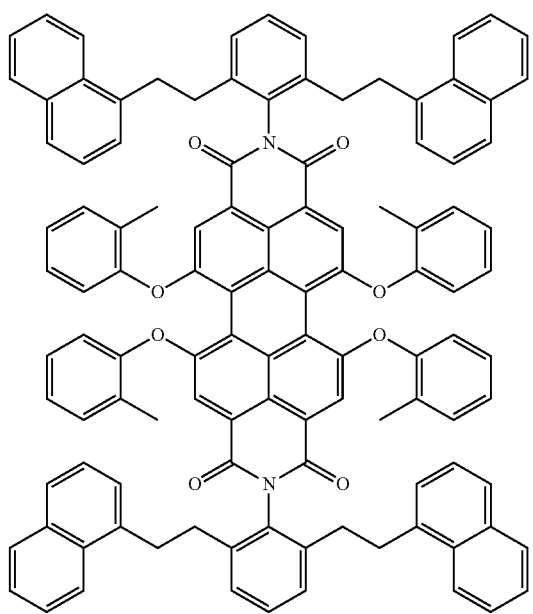
[Chem 52]
C-126
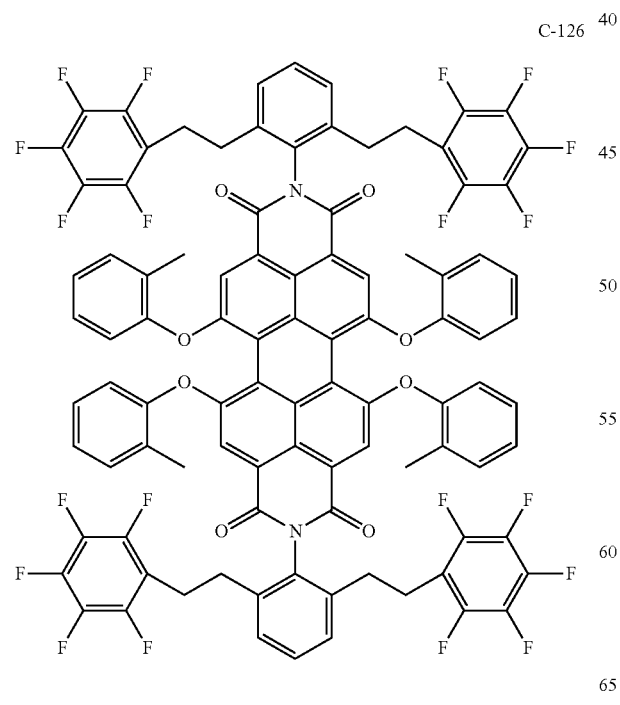
C-128
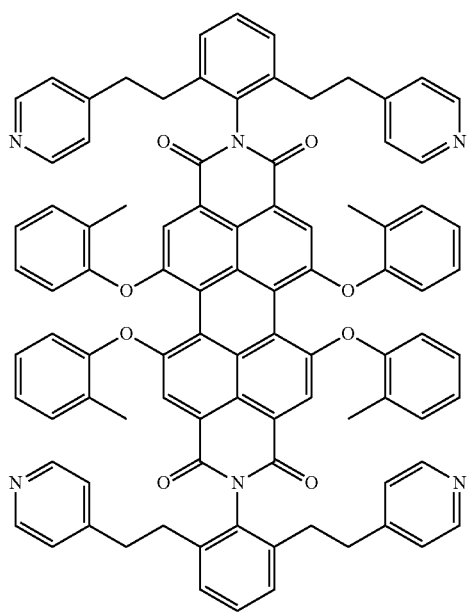

[Chem 53]
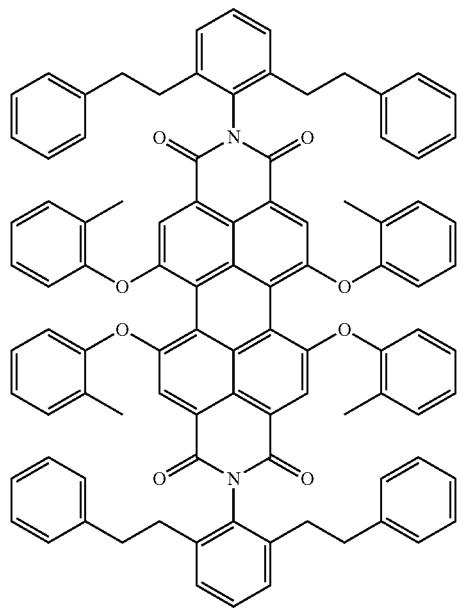
C-129
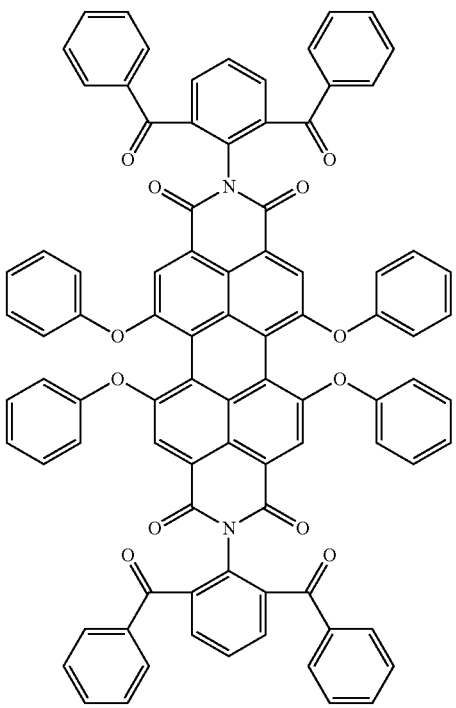
C-131
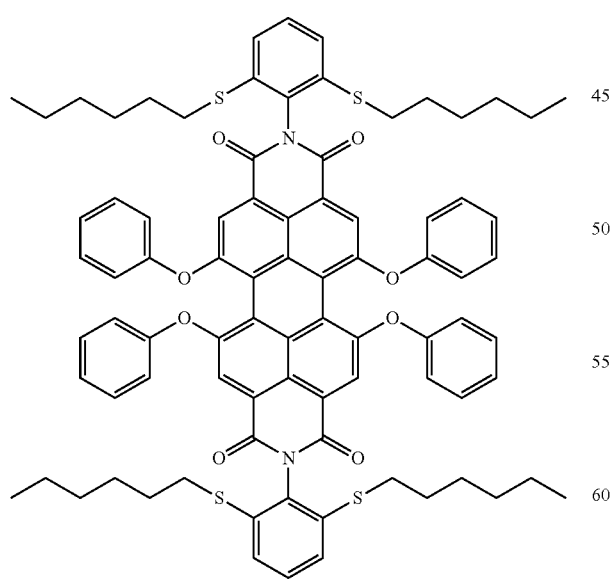
C-130
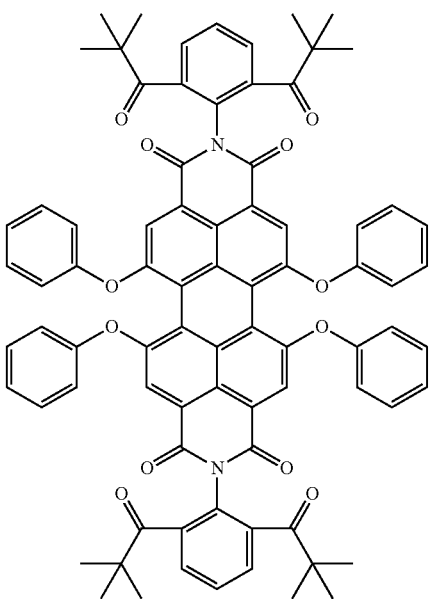
C-132

C-133
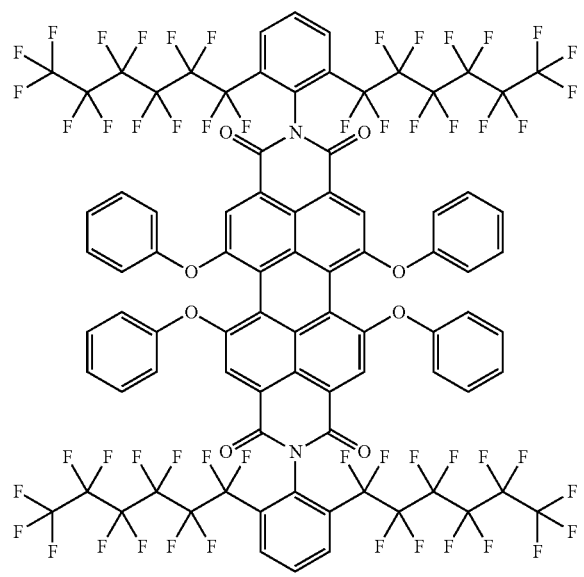
C-135
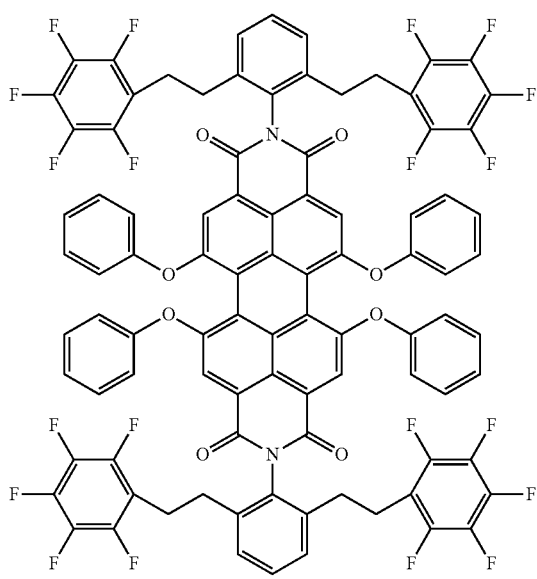
[Chem 54]
C-134
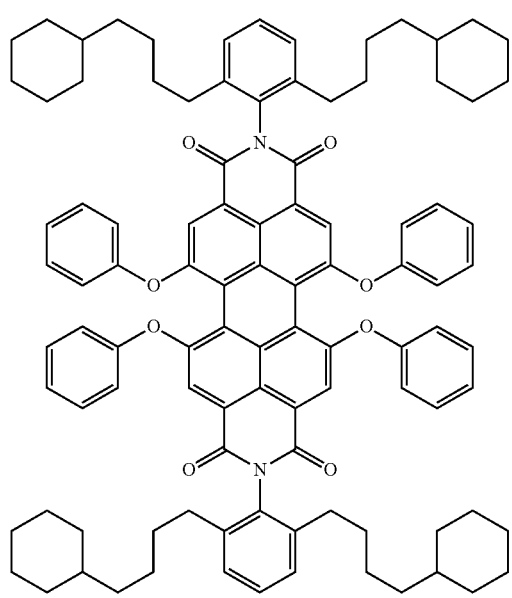
C-136
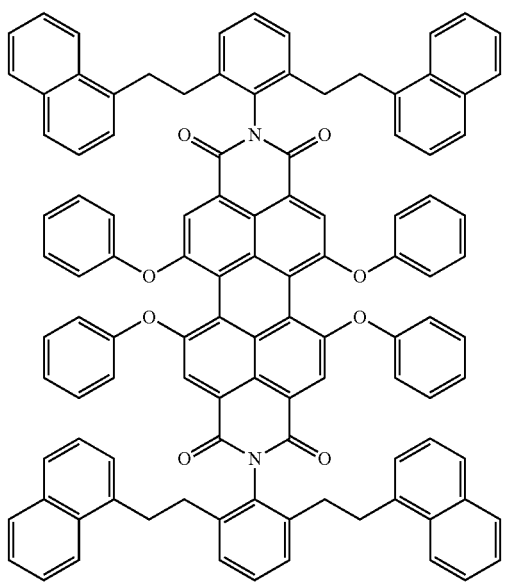

C-137
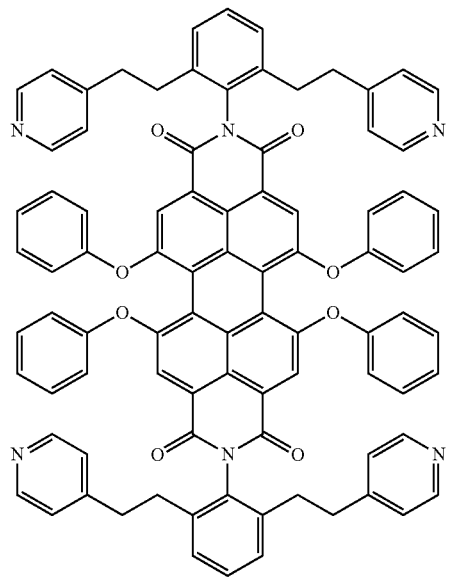
[Chem 55]
C-138
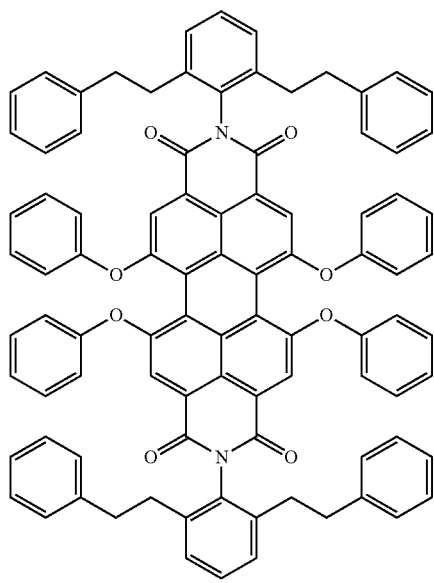
C-139
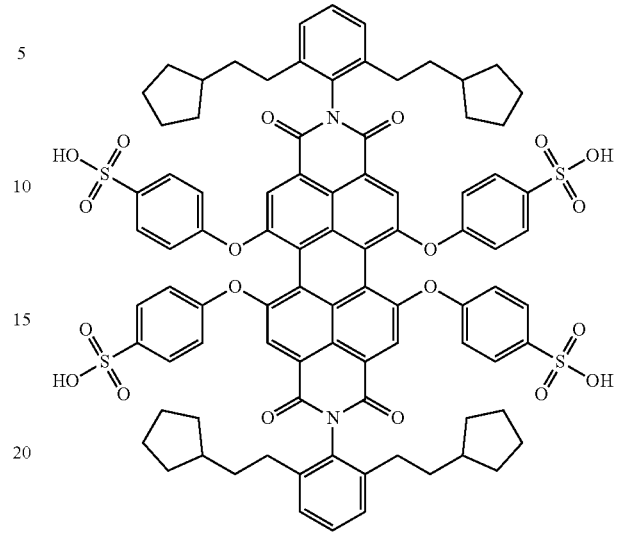
C-140
C-141
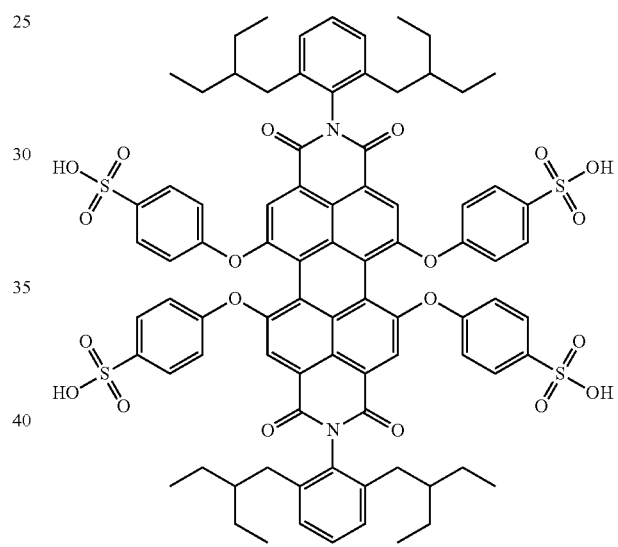
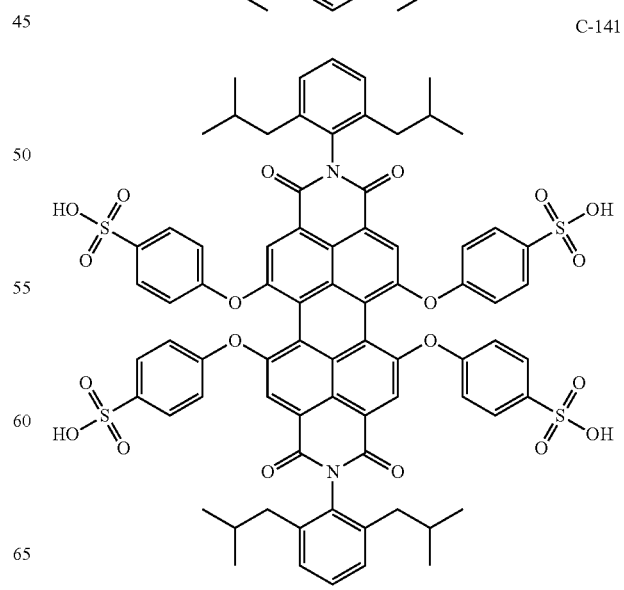

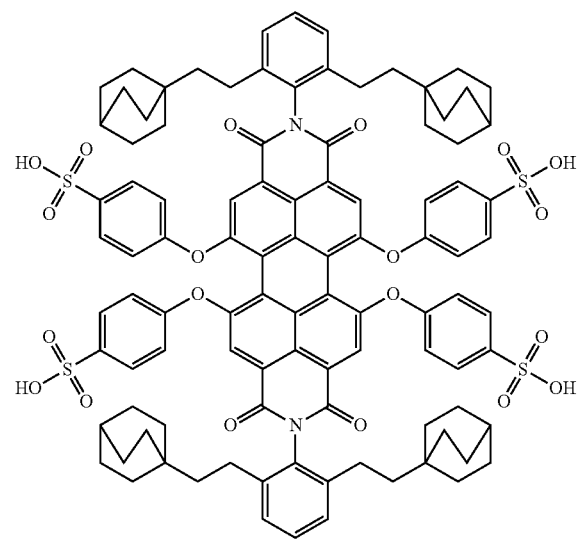
C-142
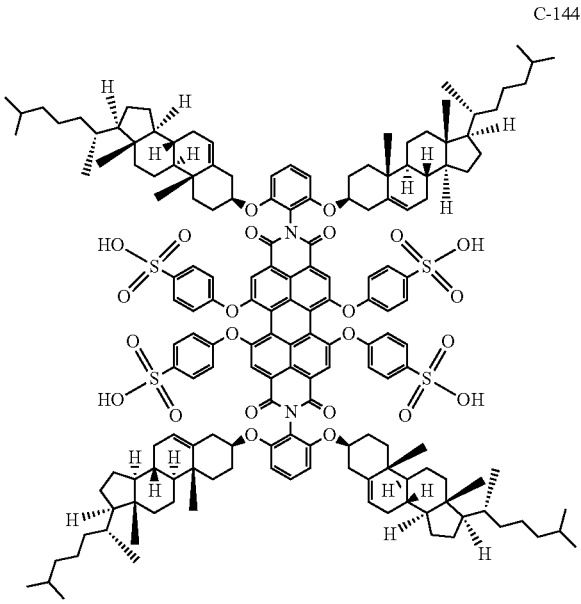
C-144
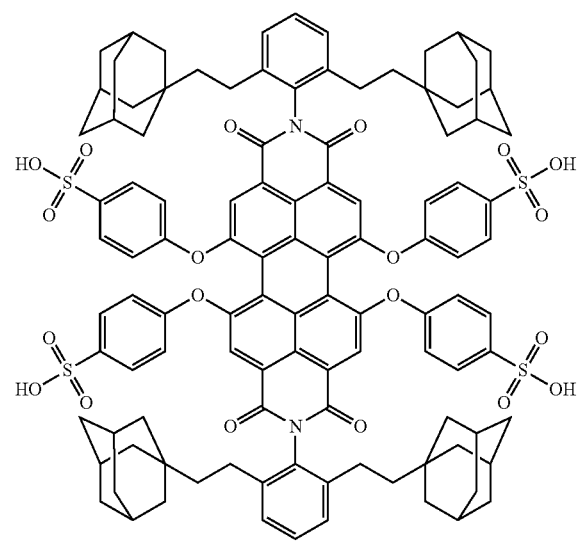
C-143
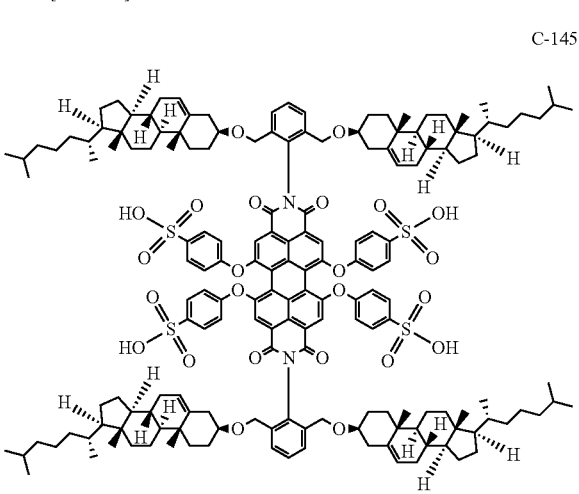
C-145

-continued
C-146
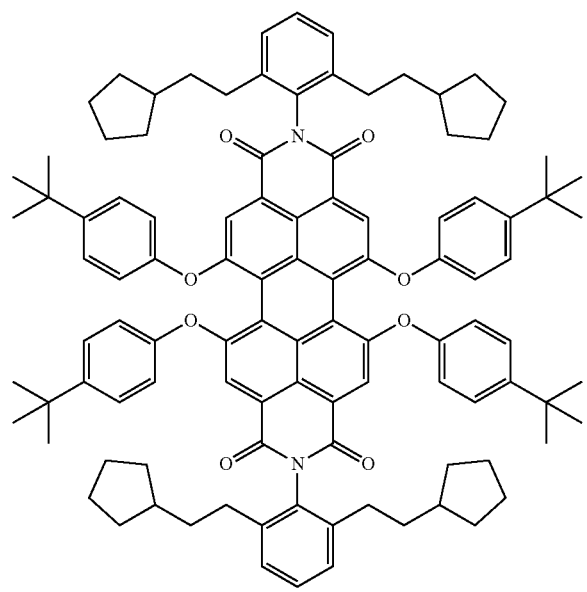
C-148
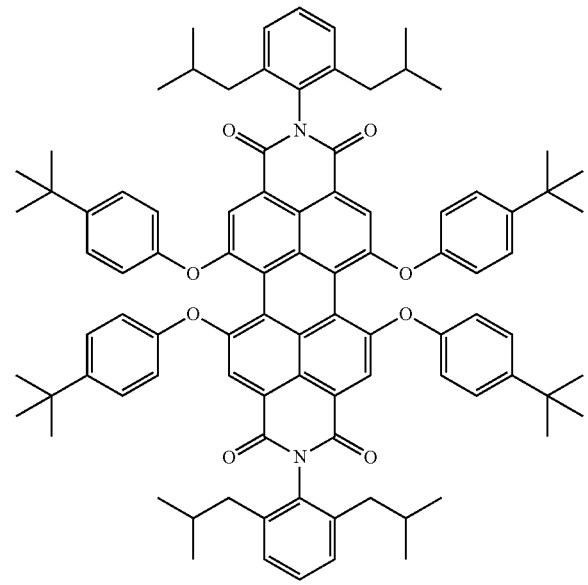
[Chem 59]
C-147
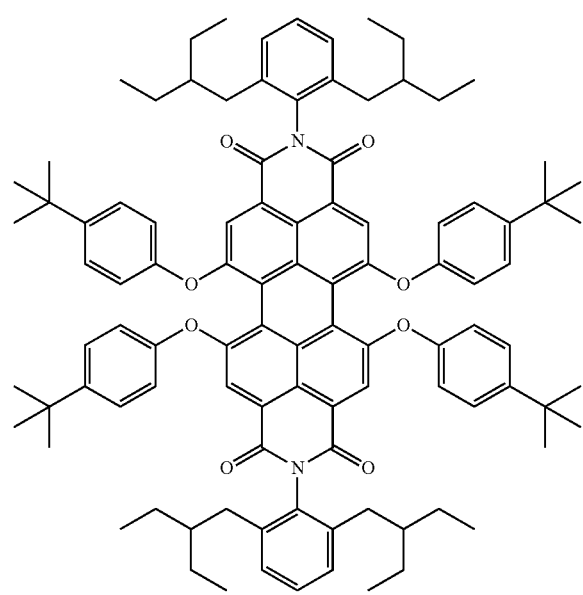
C-149
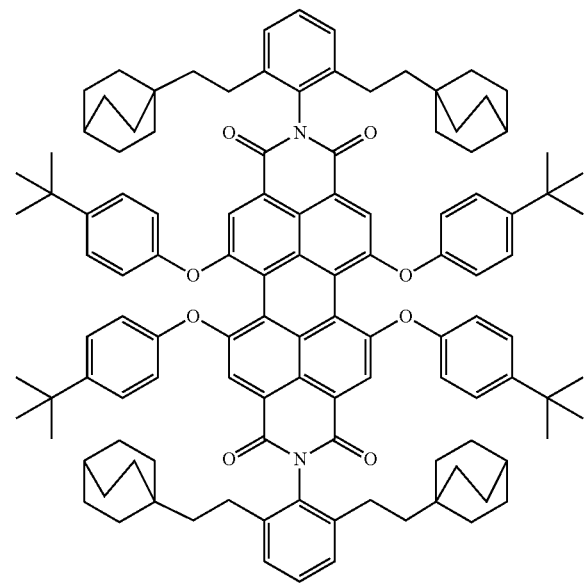

-continued
C-150
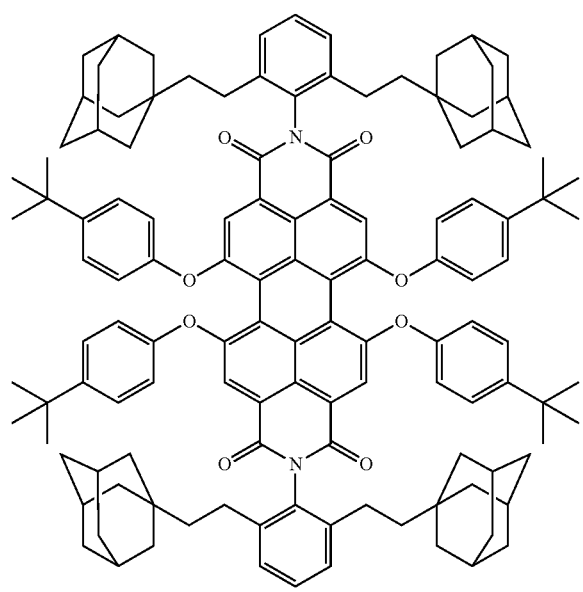
[Chem 60]
C-151
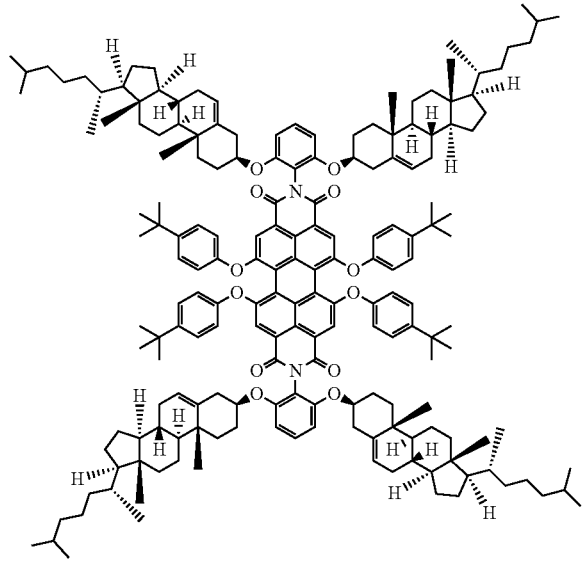
-continued
[Chem 61]
C-152
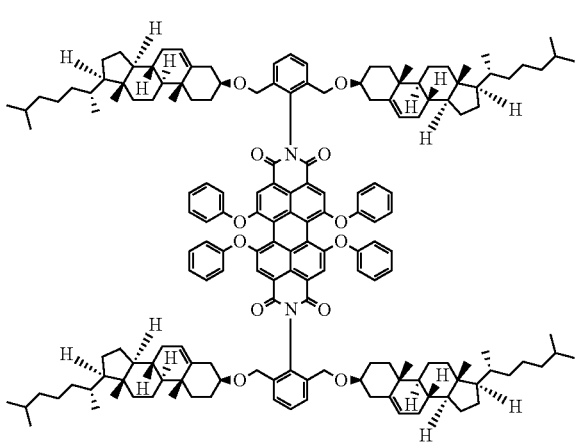
C-153
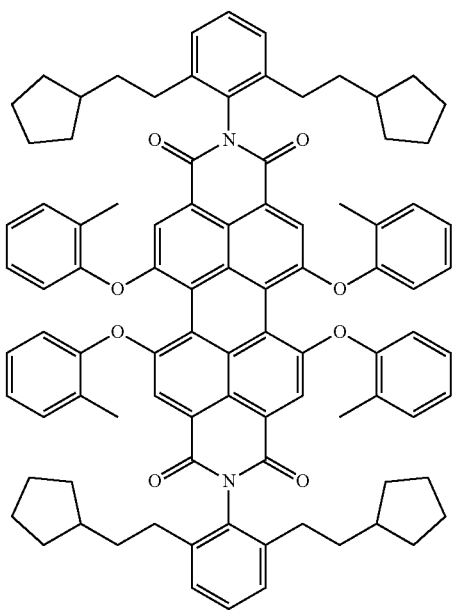

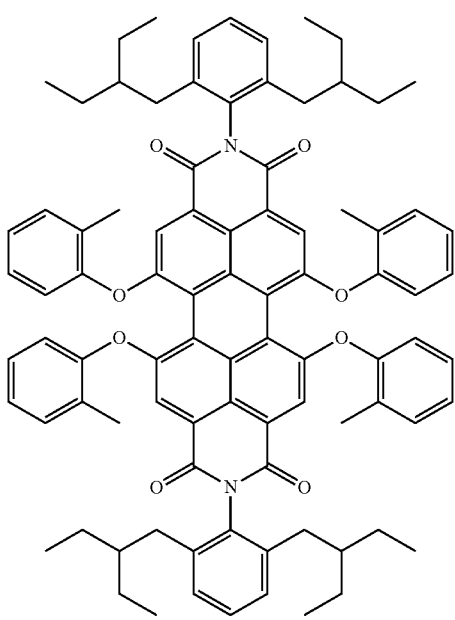
C-154
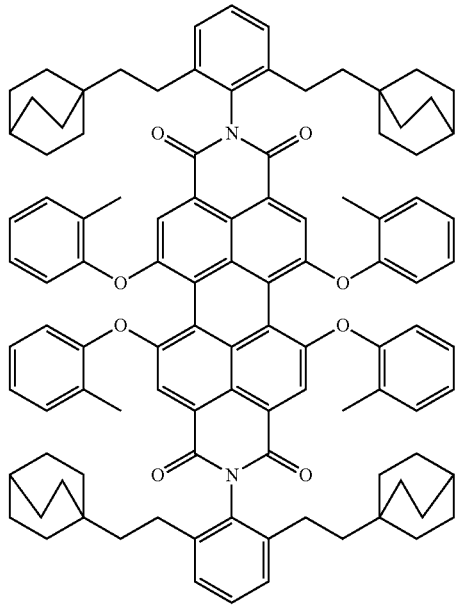
C-156
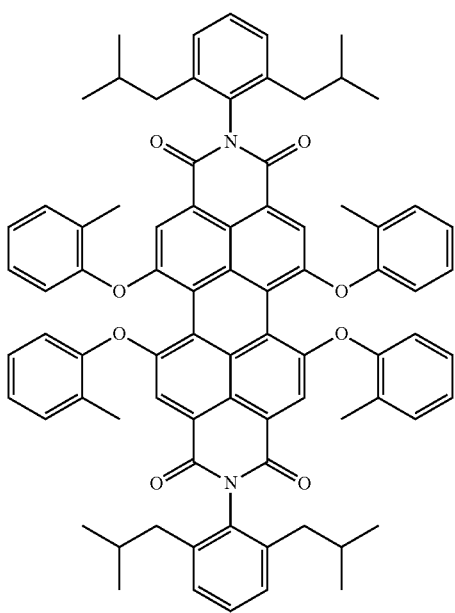
C-155
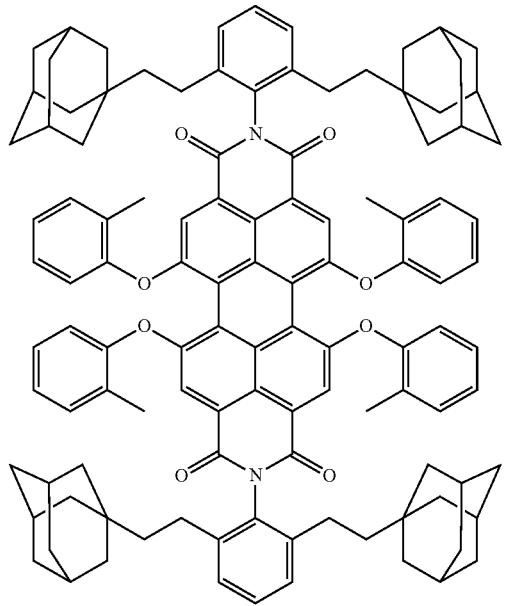
C-157

[Chem 63]
C-158
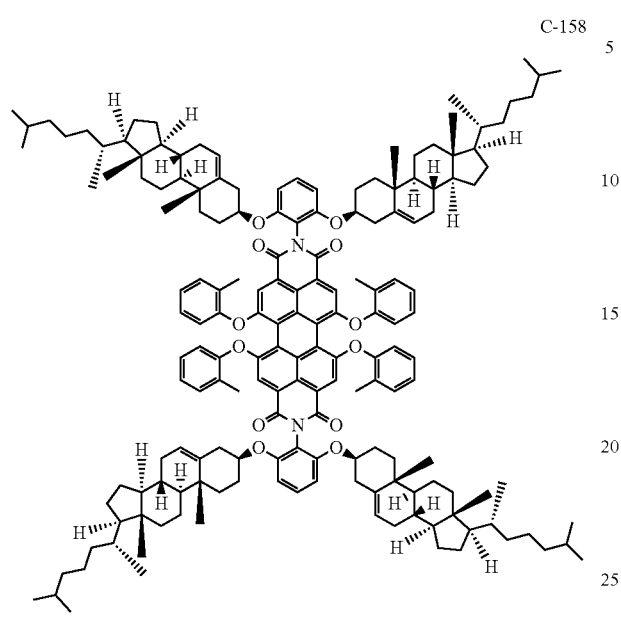
[Chem 64]
C-159
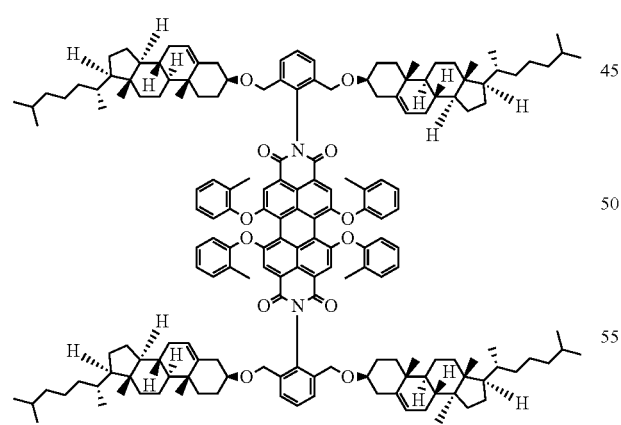
[Chem 65]
C-160
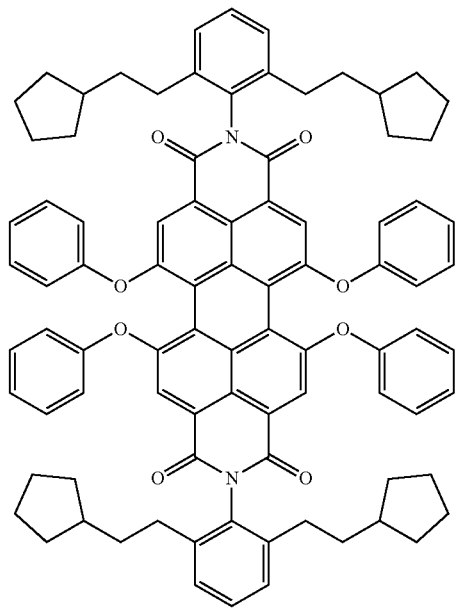
C-161
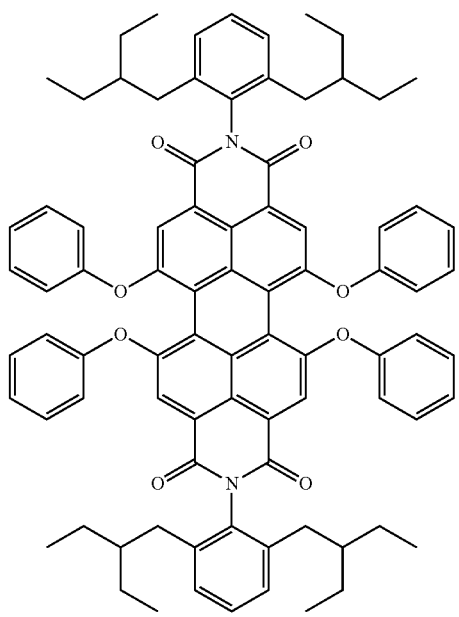

C-162
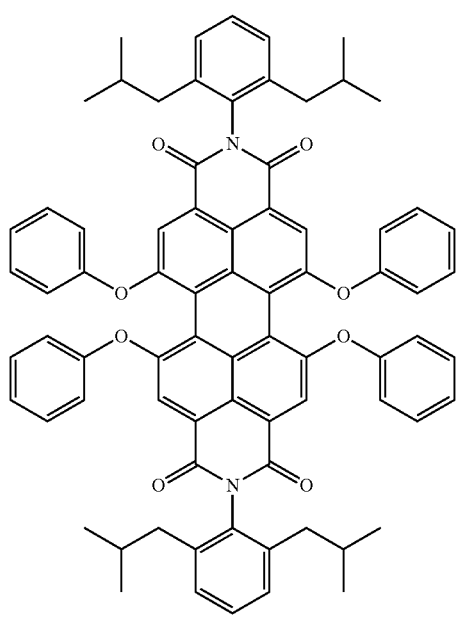
C-164
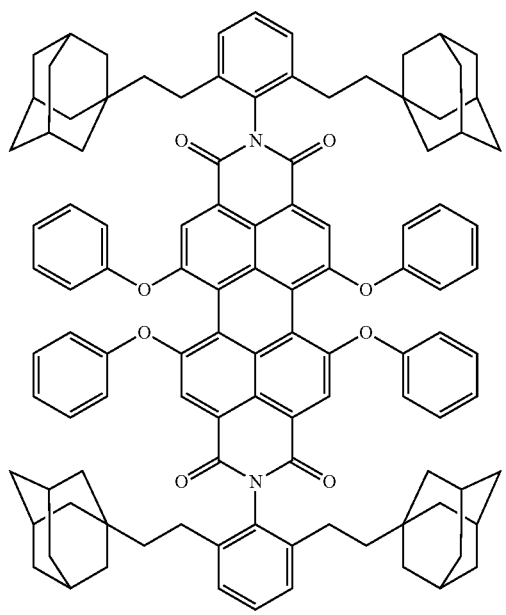
C-163
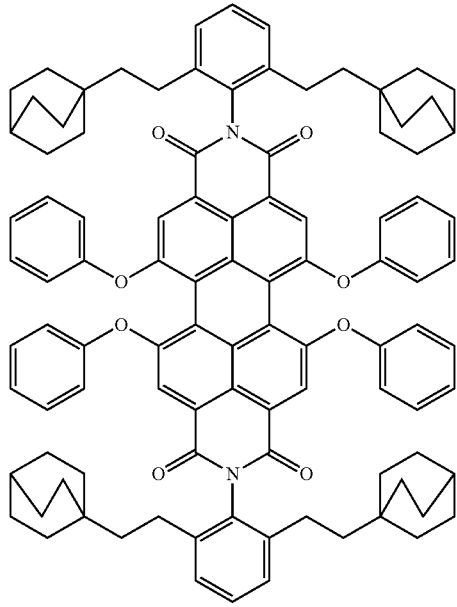
[Chem 66]
C-165
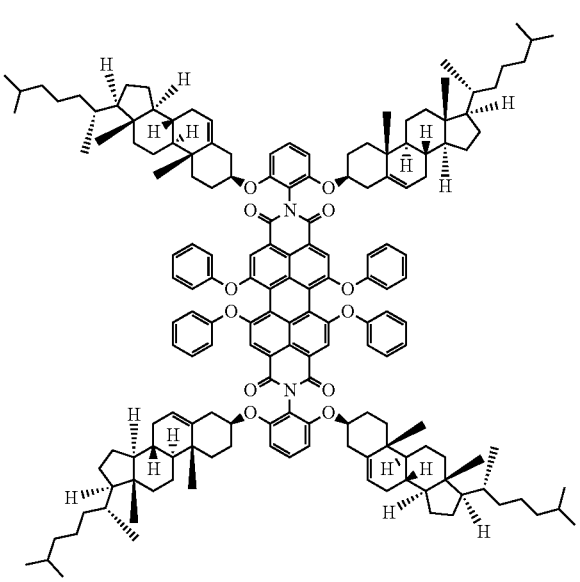

[Chem 67]
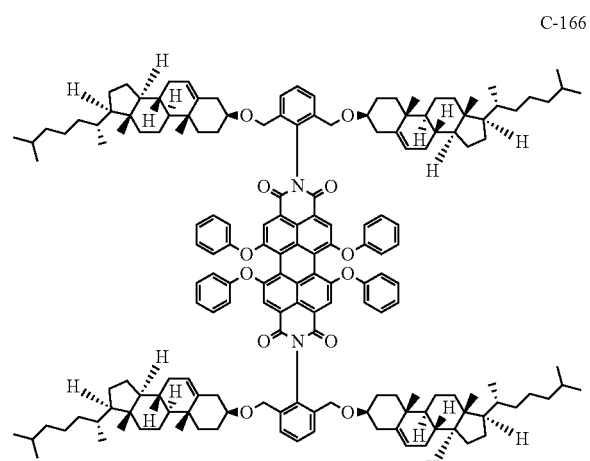
C-166
[Chem 68]
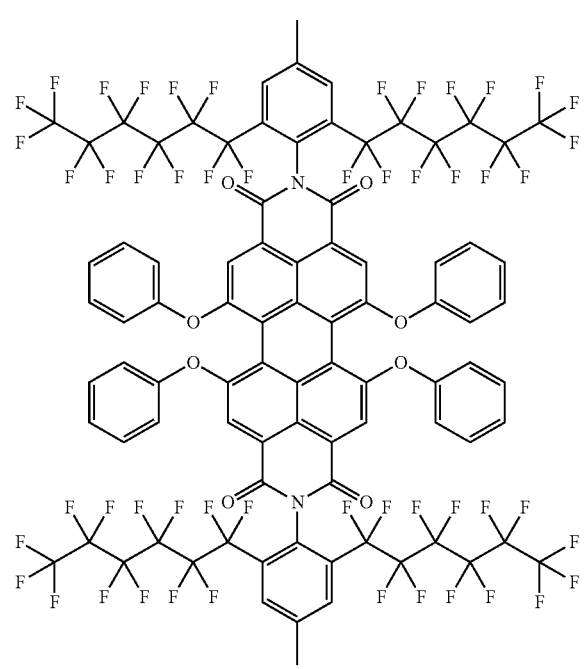
C-167
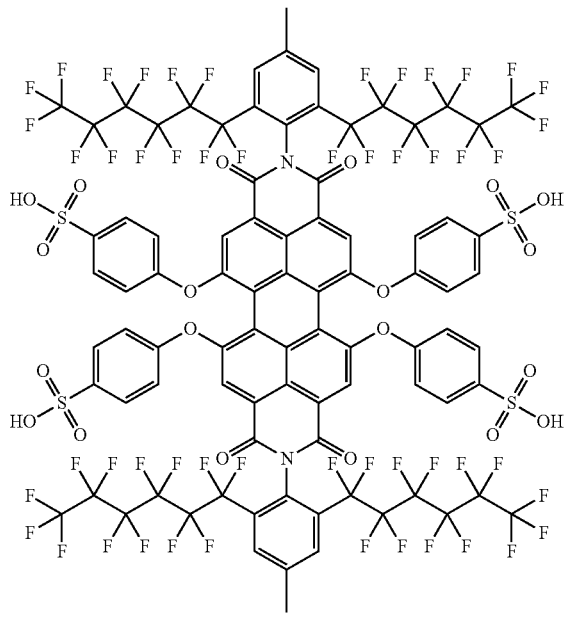
C-168
[Chem 69]
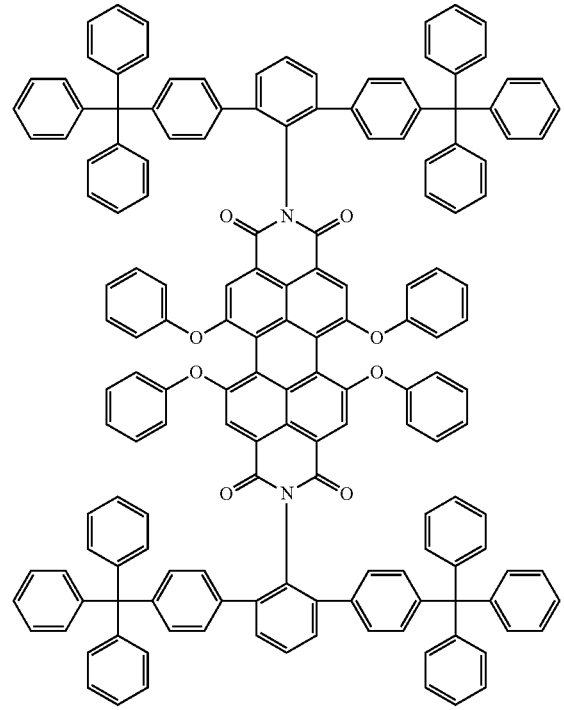
C-169

-continued
C-170
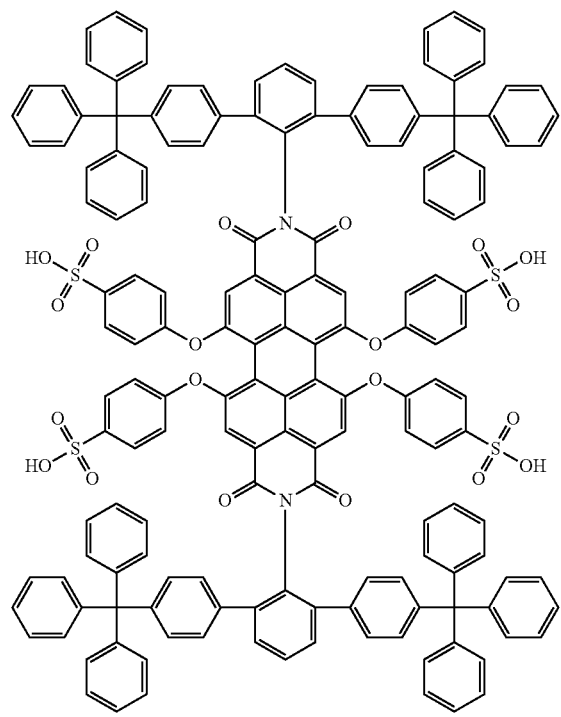
[Chem 70]
C-171
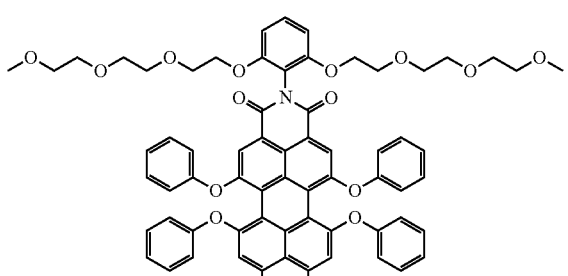
C-172
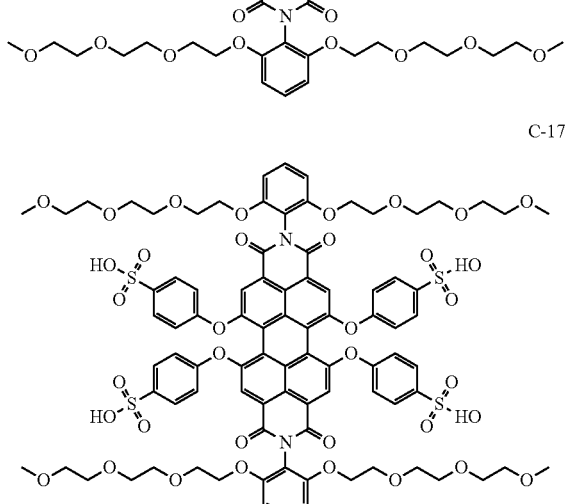
-continued
[Chem 71]
C-173
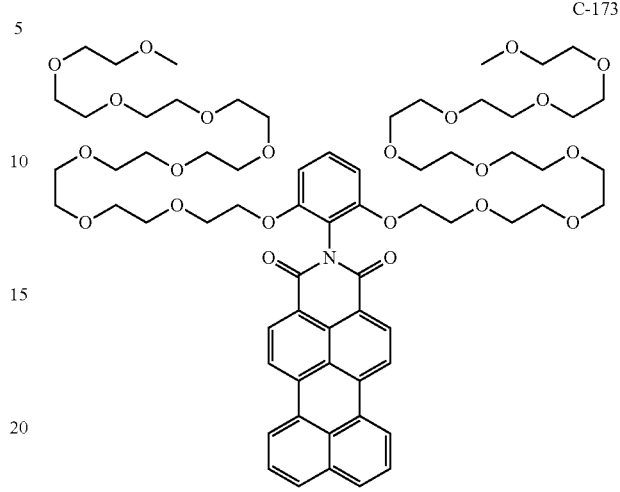
C-174
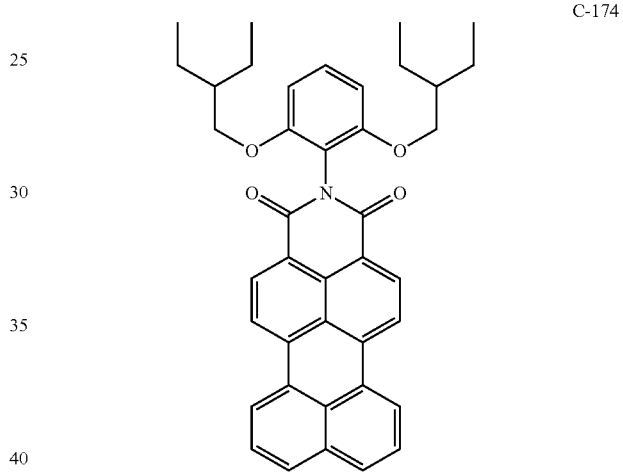
C-175
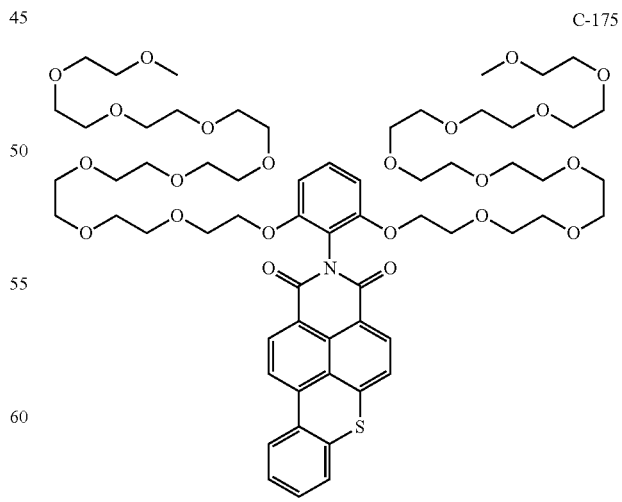

C-176
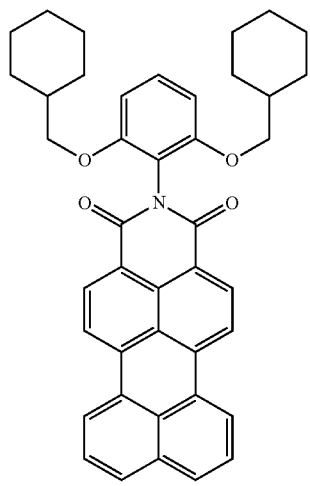
C-177
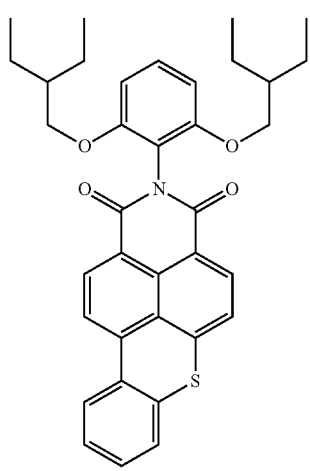
C-178
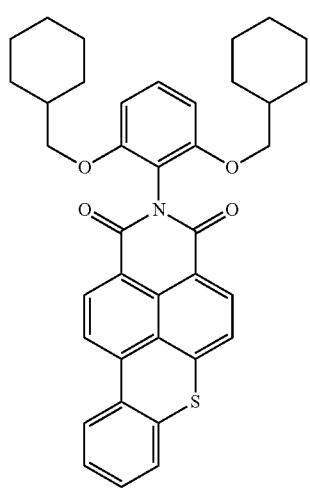
[Chem 72]
C-179
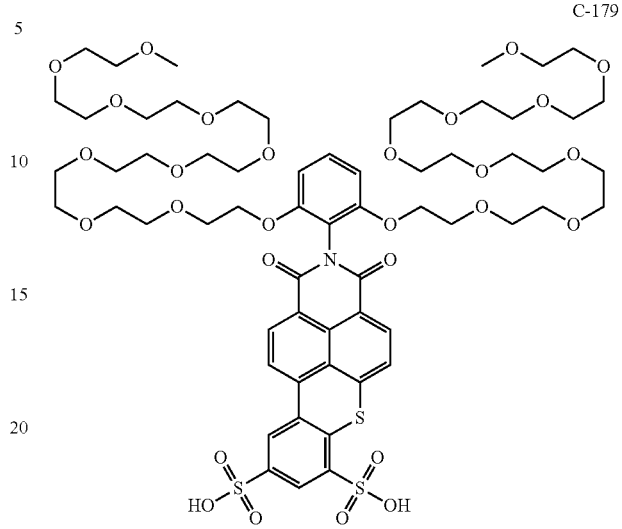
C-180

-continued

C-181

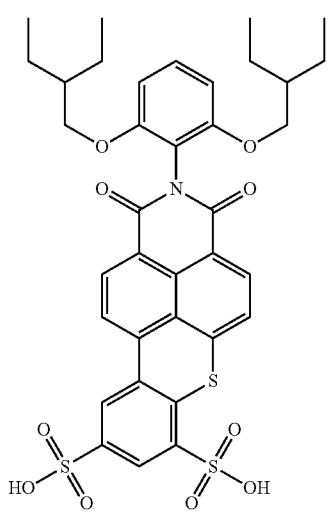

C-182

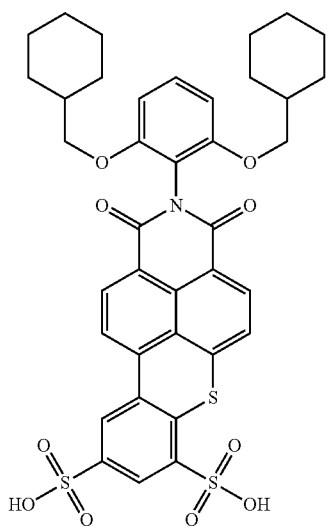

(Synthesis of Imide Derivative)

The imide derivative of the present invention can synthesized by a known method, for example, by referring to Chem. Eur. J. 2004, 10, 5297-5310. As examples, synthetic schemes of Exemplified Compounds C-53 and C-30 among the known compounds in the above document are shown below. Other exemplified compounds can be synthesized in the same manner. In the synthetic scheme, NMP represents N-methyl-2-pyrrolidone.

<Synthesis of Exemplified Compound C-53>

[Chem 73]

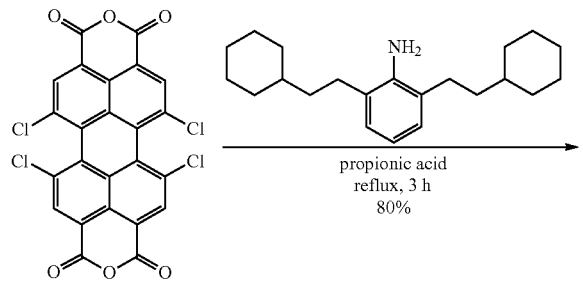

-continued

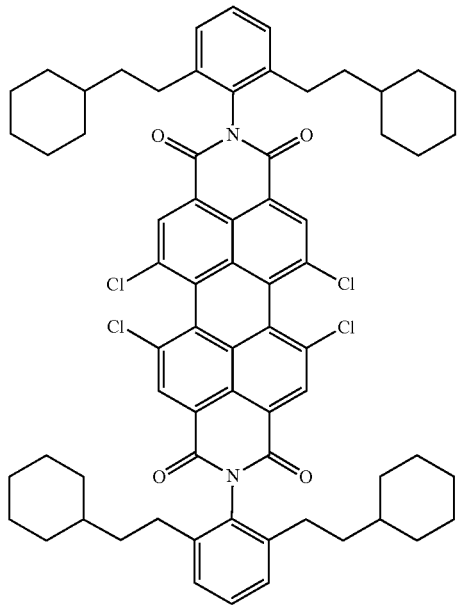

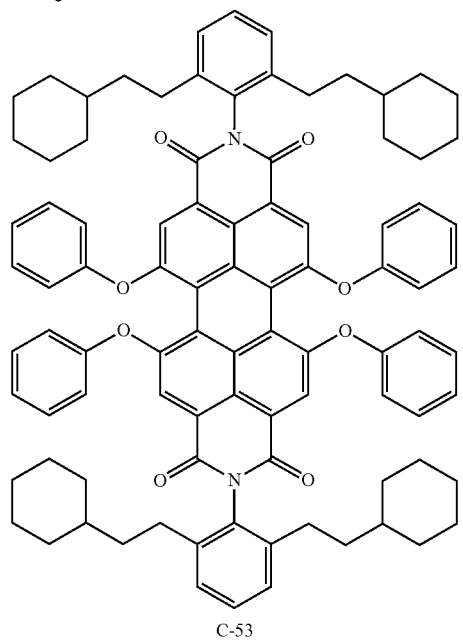

C-53

Synthesis of Exemplified Compound C-30

[Chem 74]

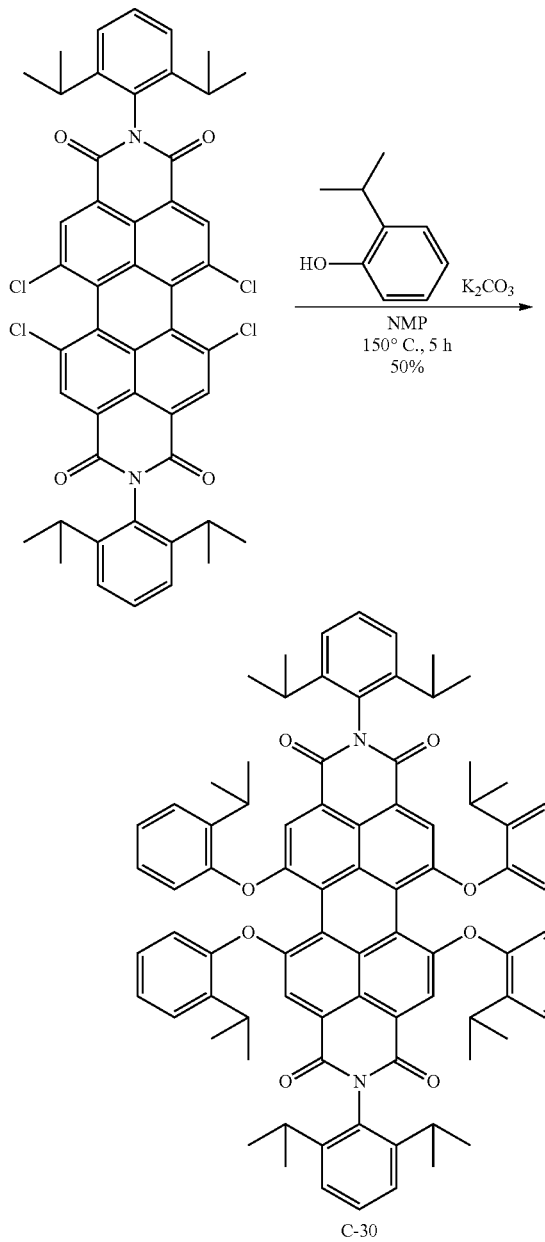

C-30

[Luminous Quantum Yield]

The luminous quantum yield is expressed as the ratio of the number of absorbed photons to the number of emitted photons. When all the excited molecules return to the ground state by emitting fluorescence, the luminous quantum yield is 1, but it is not 1 in reality due to non-radiative deactivation.

Non-radiative deactivation is a transition that returns to the ground state without emitting fluorescence, and includes, in addition to relaxation to the triplet state by intersystem crossing, internal conversions in which the energy of the electronic state is converted into vibration energy and finally becomes thermal energy, and energy transfer in which the energy is transferred to other molecules.

Assuming that the rate constants of the fluorescence transition and the non-radiation transition of the excited molecule are Kf and Knr, respectively, the luminous quantum yield Φ (%) is represented by the following.

$$\Phi(\%) = (Kf/(Kf+Knr)) \times 100$$

Therefore, in order to improve the luminous quantum yield, it is necessary to suppress the non-radiative deactivation of the excited molecules.

In the present invention, in order to suppress non-radiative deactivation, the imide derivative of the present invention has a substituent that causes steric hindrance. This substituent suppresses π-plane stacking of molecules and may suppress the aggregation between the molecules. As a result, it is presumed that the quenching caused by aggregation becomes smaller and the luminescence is improved.

[Measurement of Luminous Quantum Yield]

The imide derivative of the present invention can exhibit a high luminous quantum yield not only in a dilute solution but also in a high concentration solution or in a film state due to suppressed concentration quenching.

<Measurement of Luminous Quantum Yield in Solution State>

For measurement of luminous quantum yield in solution state, an imide derivative is dissolved in 2-methyl tetrahydrofuran. The luminous quantum yield can be measured as an absolute fluorescence quantum yield using a fluorescence quantum yield spectrometer (C11347-01 manufactured by Hamamatsu Photonics K.K.), for example.

<Measurement of Luminous Quantum Yield in Film State>

The imide derivative of the present invention is ultrasonically washed with isopropyl alcohol, and dried with dry nitrogen gas. Then, while a UV ozone-washed quartz substrate (1 cm square) placed on a hot plate is heated at 150° C., a chlorobenzene solution of each compound is added thereto dropwise, and is baked after that at 150° C. for 30 minutes to prepare a single film. The absolute luminous quantum yield of this single film can be measured in a nitrogen atmosphere using the fluorescence quantum yield spectrometer (C11347-01 manufactured by Hamamatsu Photonics K.K.). This can be measured as the luminous quantum yield.

<<Applications>>

The imide derivative of the present invention can exhibit a high luminous quantum yield not only in a dilute solution but also in a high concentration solution or in a film state due to suppressed concentration quenching. Because of such properties, the imide derivative of the present invention can be applied to a luminescent composition, a luminous thin film, and luminous particles. For example, it can be applied, as a highly efficient light emitting material, to an organic electronic device such as an organic electroluminescence element. It can also be applied, as a new type of dye for fluorescent probes, to a marker in biology and medicine in bioimaging. Furthermore, the imide derivative of the present invention, which emits fluorescence as extra energy when the excited electrons return to the ground state, has a wavelength conversion ability due to the difference in energy between absorption and emission, and can be used as a color conversion filter applicable to dyes, pigments, optical filters, agricultural films, and the like.

<Luminescent Composition and Luminous Thin Film>

The luminescent composition of the present invention includes the imide derivative of the present invention. The luminescent composition of the present invention is preferably used as a composition in which a dispersant is added to the imide derivative for film formation stability and the like, or a composition in which a solvent is further added. Furthermore, the luminous thin film of the present invention includes the imide derivative of the present invention. Specifically, the luminous thin film can be produced by forming the luminescent composition of the present invention in the form of a thin film.

Examples of the dispersant are a (meth)acrylate resin, a polyester resin, a polyamide resin, a polyimide resin, a polystyrene resin, a polyepoxy resin, a polyester resin, an amino resin, a fluorine resin, a phenol resin, a polyurethane resin, a polyethylene resin, a polypropylene resin, a polyvinyl chloride resin, a polyvinyl alcohol resin, a polyether resin, a polyether ketone resin, a polyphenylene sulfide resin, a polycarbonate resin, and an aramid resin. Among them, a polystyrene resin, a polyethylene resin, a polypropylene resin, and a polyvinyl chloride resin are preferable. The copolymers of these are also preferable.

The (meth)acrylate resin is synthesized by homopolymerizing or copolymerizing various methacrylate monomers or acrylate monomers, and by changing the monomer species and the monomer composition ratio, the desired (meth)acrylate may be obtained. Furthermore, in the present invention, a methacrylate monomer can be copolymerized with a copolymerizable monomer having an unsaturated double bond other than the (meth) acrylate-based monomer. Furthermore, in the present invention, a poly(meth) acrylate-based resin may be mixed with a plurality of other resins for use.

Examples of a monomer component that forms a (meth)acrylate resin used in the present invention include (Meth)acrylic acid, methyl (meth)acrylate, ethyl (meth)acrylate, propyl (meth)acrylate, butyl (meth)acrylate, isopropyl (meth)acrylate, isobutyl (meth)acrylate, t-butyl (meth)acrylate, stearyl (meth)acrylate, 2-hydroxyethyl (meth)acrylate, acetoacetoxyethyl (meth)acrylate, dimethylaminoethyl (meth)acrylate, 2-hydroxypropyl (meth)acrylate, di(ethylene glycol) ethyl ether (meth)acrylate, ethyleneglycol methyl ether (meth)acrylate, isobonyl (meth)acrylate, ethyltrimethylammonium chloride (meth)acrylate, trifluoroethyl (meth)acrylate, octafluoropentyl (meth)acrylate, 2-acetamidomethyl (meth)acrylate, 2-methoxyethyl (meth)acrylate, 2-dimethylaminoethyl (meth)acrylate, 3-trimethoxysilanepropyl (meth)acrylate, benzyl (meth)acrylate, tridecyl (meth)acrylate, 4-hydroxybutyl (meth)acrylate, tetrahydrofurfuryl (meth)acrylate, dodecyl (meth)acrylate, octadecyl (meth)acrylate, 2-diethylaminoethyl (meth)acrylate, 2-ethylhexyl (meth)acrylate, cyclohexyl (meth)acrylate, phenyl (meth)acrylate, and glycidyl (meth)acrylate. Among them, (meth)acrylic acid, methyl (meth)acrylate, ethyl (meth)acrylate, propyl (meth)acrylate, butyl (meth)acrylate, stearyl (meth)acrylate, 2-hydroxyethyl (meth)acrylate, acetoacetoxyethyl (meth)acrylate, benzyl (meth)acrylate, tridecyl (meth)acrylate, dodecyl (meth)acrylate, and 2-ethylhexyl (meth)acrylate are preferable.

The polystyrene resin includes a homopolymer of a styrene monomer, or a random copolymer, a block copolymer, or a graft copolymer obtained by copolymerizing another monomer having an unsaturated double bond copolymerizable with the styrene monomer. Further included are blends and polymer alloys in which such polymers are blended with other polymers. Examples of the styrene monomer include: a nucleus alkyl substituted styrene such as styrene, α-methylstyrene, α-ethylstyrene, α-methylstyrene-p-methylstyrene, o-methylstyrene, m-methylstyrene, and p-methylstyrene; and a nucleus halogen substituted styrene such as o-chlorstyrene, m-chlorstyrene, p-chlorstyrene, p-bromstyrene, dichlorostyrene, dibromostyrene, trichlorostyrene, and tribromostyrene. Among them, styrene and α-methylstyrene are preferred.

Examples of the resin used in the present invention by homopolymerizing or copolymerizing these monomers include: a copolymer resin of benzyl methacrylate/ethyl acrylate or butyl acrylate, a copolymer resin of methyl methacrylate/2-ethylhexyl methacrylate, and a copolymer resin of methyl methacrylate/methacrylate/stearyl methacrylate/acetoacetoxyethyl methacrylate, a copolymer resin of styrene/acetoacetoxyethyl methacrylate/stearyl methacrylate, a copolymer resin of styrene/2-hydroxyethyl methacrylate/stearyl methacrylate, and a copolymer resin of 2-ethylhexyl methacrylate/2-hydroxyethyl methacrylate.

Regarding the content of the luminescent material in the luminescent composition and the luminous thin film of the present invention, the preferable lower limit is 0.001 parts by mass and the preferable upper limit is 50 parts by mass with respect to 100 parts by mass of the dispersant. When the content of the luminescent material is within this range, it has high transparency and may display a high-luminance image by being irradiated with light. A more preferable lower limit of the content of the luminescent material is 0.01 parts by mass, a more preferable upper limit is 10 parts by mass, a further preferable lower limit is 0.05 parts by mass, a further preferable upper limit is 8 parts by mass, and a particularly preferable lower limit is 0.1 parts by mass, a particularly preferable upper limit is 5 parts by mass.

Furthermore, the luminous thin film of the present invention can be appropriately used when it has a thickness within a range of 0.1 nm to 1 mm.

<Luminous Particles>

The luminous particles of the present invention includes the imide derivative of the present invention. It may be luminous particles in which an imide derivative is adsorbed on the particle surface, or luminous particles containing an imide derivative.

For example, luminous particles can be produced by aggregating the imide derivative in a polymer particle dispersion in a liquid. Alternatively, it may be luminous particles containing the imide derivative by using a swellable polymer whose volume expands when the polymer particles are immersed in and adsorbs a solvent.

As the polymer particles, a commercially available product may be used, or those synthesized by a conventionally known method may be used. The conventionally known method is preferably an emulsion polymerization method, but is not particularly limited, and examples thereof include a dispersion polymerization method, a suspension polymerization method, and an emulsion polymerization method. As the monomer used as a raw material for the polymer, various monomers listed as the dispersant can be used.

The solvent used for aggregation of the imide derivative in the polymer dispersion in the liquid is not particularly limited. A known solvent can be used.

The volume average particle diameter of the polymer particles is preferably in the range of 0.01 to 50 μm, more preferably 0.02 to 40 μm, and even more preferably 0.04 to 20 μm.

When the volume average particle diameter is in the above range, the obtained luminous particles can be applied to various uses. Specifically, the volume average particle diameter can be measured by a LS 13320 Laser Diffraction Light Scattering Particle Size Analyzer.

The weight average molecular weight of the polymer particles is preferably in the range of 1,000 to 1,000,000, more preferably 5,000 to 800,000, and more preferably 10,000 to 600,000.

The polymer particles contained in the luminous particles of the present invention may be one kind or two or more kinds, but are usually one kind.

[Organic Electroluminescence Element]

The organic electroluminescence element (organic EL element) has a substrate and a light emitting layer including a light emitting compound (luminescent material) sandwiched between a cathode and an anode on the substrate. Electrons and holes injected into the light emitting layer are recombined to form an exciton. Light emitted in response to deactivation of the exciton is used as the luminescence of the organic EL element. The imide derivative of the present invention can be applied to an organic EL device as a fluorescent light emitting material.

Preferable specific examples of the layer structure of the organic EL element are shown below.

(i) Anode/light emitting layer/electron transport layer/cathode (ii) Anode/hole transport layer/light emitting layer/electron transport layer/cathode (iii) Anode/hole transport layer/light emitting layer/hole blocking layer/electron transport layer/cathode (iv) Anode/hole transport layer/light emitting layer/hole blocking layer/electron transport layer/cathode buffer layer/cathode (v) Anode/anode buffer layer/hole transport layer/light emitting layer/hole blocking layer/electron transport layer/cathode buffer layer/cathode The light emitting layer is a layer in which electrons injected from the electrode or the electron transport layer and holes injected from the hole transport layer are recombined, and light is emitted. The light emitting layer may emit light either inside the light-emitting layer or at the interface between the light emitting layer and its adjacent layer. The imide derivative of the present invention can be used in the light emitting layer. Because of the small concentration quenching, a high luminous quantum yield can be realized even in the form of a film.

When the imide derivative of the present invention is used as a luminescent material of an organic EL element, known host compound can be used as a dispersant. Specific examples thereof include compounds disclosed in the followings, but the present invention is not limited thereto: Japanese Patent Laid-Open Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837, US Patent Application Nos. 2003/0175553, 2006/0280965, 2005/0112407, 2009/0017330, 2009/0030202, and 2005/238919, WO2001/039234, WO2009/021126, WO2008/056746, WO2004/093207, WO2005/089025, WO2007/063796, WO2007/063754, WO2004/107822, WO2005/030900, WO2006/114966, WO2009/086028, WO2009/003898, WO2012/023947, Japanese Patent Laid-Open Nos. 2008-074939 and 2007-254297, European Patent Laid-Open No. 2034538, WO2011/055933, WO2012/035853, and Japanese Patent Laid-Open No 2015-38941.

A known material such as another fluorescent light emitting material or a phosphorescent light emitting material can be used in combination in the light emitting layer. A charge injection layer is a layer provided between the electrode and the light emitting layer in order to reduce the driving voltage and improve the luminous intensity, and includes a hole injection layer and an electron injection layer.

The hole transport layer is made of a hole transport material having a function of transporting holes, and in a broad sense, the hole injection layer and the electron blocking layer also have the function of the hole transport layer. One or a plurality of hole transport layer may be provided.

The electron transport layer is made of a material having a function of transporting electrons, and in a broad sense, an electron injection layer and a hole blocking layer also functions as the electron transport layer. The electron transport layer can be provided as a single-layer structure or a laminated structure of a plurality of layers.

Examples of the blocking layer include a hole blocking layer and an electron blocking layer, which are layers provided as needed in addition to the constituent layers of the organic functional layers described above.

Known materials can be used for the substrate, electrodes, charge injection layer, hole transport layer, electron transport layer, blocking layer, and the like.

[Bioimaging]

The imide derivative of the present invention can be used as a fluorescent dye. In the application to bioimaging, living cells are stained with a fluorescent dye, the luminescent color of the stained cells is examined.

It is possible to know the environment around the cells from the luminescent color, and imaging of the intracellular environment can be performed.

For example, in a known technique to examine an expression state of a target biological substance, fluorescent labeling is performed using fluorescent substance-accumulated nanoparticles to which a biological substance recognition site is bound so as to be able to recognize and bind to the target biological substance. Specifically, a tissue sample is stained with fluorescent substance-accumulated nanoparticles, peaks in luminance distributions of the fluorescent emission bright points are analyzed to obtain the average luminance value per particle, and the number of particles in each bright point is calculated. By comparing the calculated number of particles, the expression level of the target biological substance can be evaluated.

Since the imide derivative of the present invention has a high luminous quantum yield, the luminance value per particle can be increased in the fluorescent substance-accumulated nanoparticles. Therefore, when the imide derivative is applied to bioimaging in this way, it has the advantage of being able to quantitatively detect a trace amounts of biological substances.

[Color Conversion Filter]

The color conversion filter can be used in, for example, an image display device such as a liquid crystal display (LCD), a plasma display panel (PDP), an electroluminescence display (ELD), a cathode ray tube display device (CRT), a fluorescent display tube, an electric field radiation type display, and the like, and a lighting device such as LED lighting, electroluminescence lighting, and the like. When used in an image display device, the hue can be corrected to a preferable hue without reducing the display brightness, and when used in a lighting device (particularly LED lighting), emitted white light that can be more comfortably recognized.

The color conversion filter may be the same as the conventional optical filter except that it contains at least one imide derivative of the present invention that emits fluorescence, and its configuration is not limited. For example, as well as the conventional one, it has at least a support, and may have various functional layers such as an optical functional layer, an undercoat layer, an antireflection layer, a hard coat layer, and a lubricating layer, if necessary. In the color conversion filter, the imide derivative of the present invention that emits fluorescence may be included in any of the support and various functional layers, and is usually preferably included in the support or the optical functional layer. The size and shape of the color conversion filter are not particularly limited and are appropriately determined depending on the intended use.

EXAMPLES

Hereinafter, the present invention is specifically described with reference to examples, but the present invention is not limited thereto. The representation "part(s)" or "%" used in the examples represents "part(s) by mass" or "% by mass" unless otherwise stated.

Example 1

Comparative compound 1 to Comparative compound 6 used in comparative examples are shown below.
[Chem 75]

Comparative compound 1

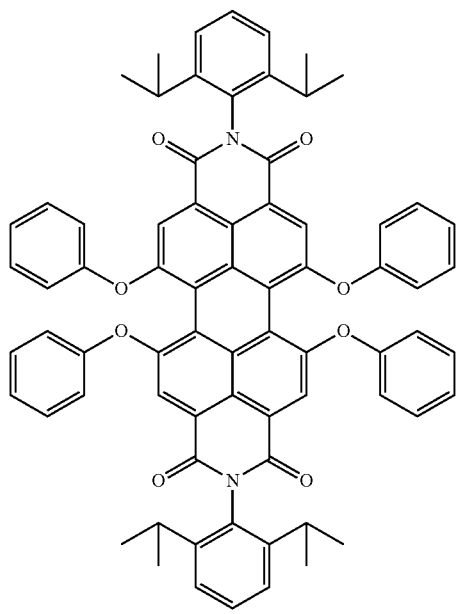

Comparative compound 2

Comparative compound 3

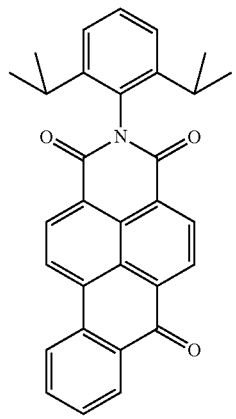

Comparative compound 4

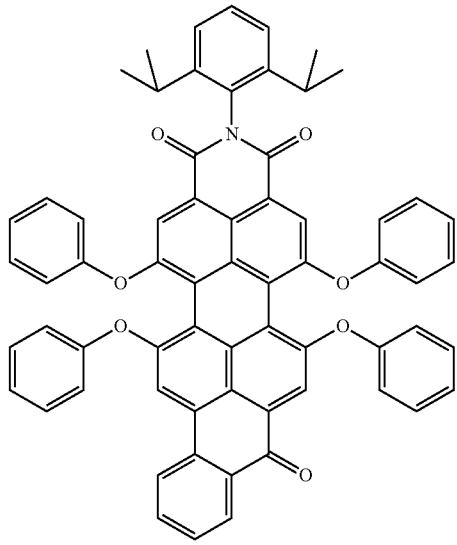

Comparative compound 5

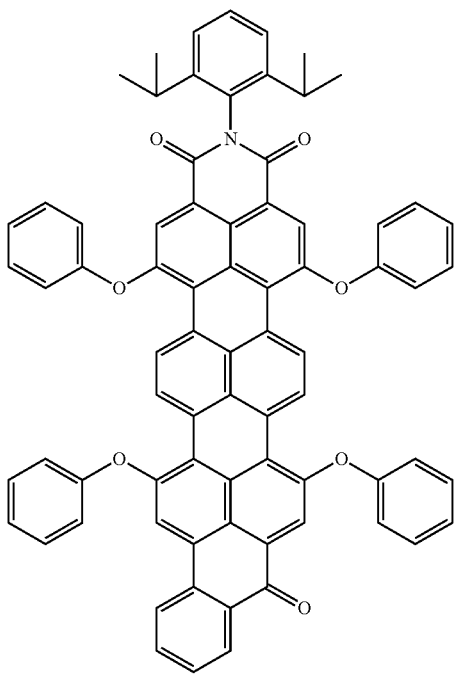

Comparative Compound 6

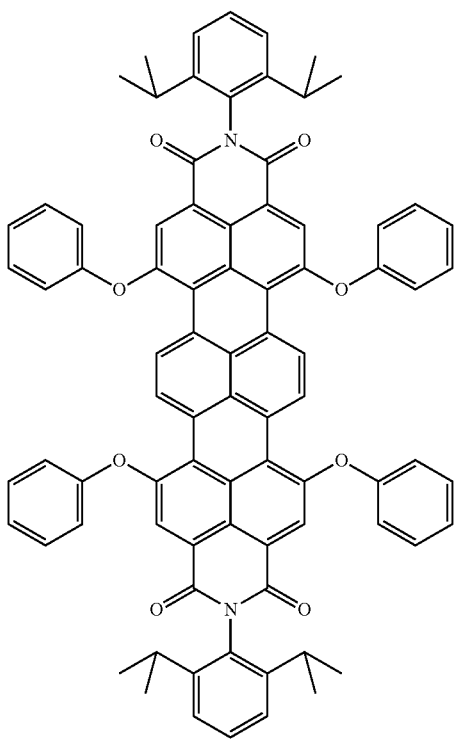

<Measurement of Luminous Quantum Yield>

The luminous quantum yields in the solution state and in the film state are were measured by the method described below, for each of the compounds shown in Table I, nineteen exemplified compounds as the imide derivatives of the present invention and six comparative compounds.

(1) Evaluation of Luminous Quantum Yield in Solution State

The imide derivative of the present invention and the comparative compound were each dissolved in 2-methyltetrahydrofuran in a concentration of $10^{-5}$ M. The absolute fluorescence quantum yield was measured using a fluorescence quantum yield spectrometer (C11347-01 manufactured by Hamamatsu Photonics K.K.), and this was used as the luminous quantum yield in the solution state.

(2) Evaluation of Luminous Quantum Yield in Film State

The imide derivatives were each ultrasonically washed with isopropyl alcohol, and dried with dry nitrogen gas. Then, while a UV ozone-washed quartz substrate (1 cm square) placed on a hot plate was heated at 150° C., a chlorobenzene solution of each compound was added thereto dropwise, and was baked after that at 150° C. for 30 minutes to prepare a single film having a thickness of 0.1 µm. The absolute luminous quantum yield was measured in a nitrogen atmosphere using the fluorescence quantum yield spectrometer (C11347-01 manufactured by Hamamatsu Photonics K.K.). This was used as the luminous quantum yield in the film state.

For each compound, a luminous quantum yield ratio of luminous quantum yield in the film state to the luminous quantum yield in the solution state ((film state)/(solution state)) was calculated and the compound was ranked according to the following evaluation criteria.

AA: (luminous quantum yield in film state/luminous quantum yield in solution state) was 0.75 or more BB: (luminous quantum yield in film state/luminous quantum yield in solution state) was 0.5 or more and less than 0.75

CC: (luminous quantum yield in film state/luminous quantum yield in solution state) was less than 0.5

The results are shown in Table I.

TABLE I

| Compound | Luminous Quantum Yield Ratio ((film state)/(solution state)) | Remarks |
| --- | --- | --- |
| C-53 | AA | Present Invention |
| C-49 | AA | Present Invention |
| C-58 | AA | Present Invention |
| C-55 | AA | Present Invention |
| C-46 | BB | Present Invention |
| C-45 | AA | Present Invention |
| C-89 | AA | Present Invention |
| C-166 | AA | Present Invention |
| C-47 | AA | Present Invention |
| C-164 | AA | Present Invention |
| C-51 | AA | Present Invention |
| C-19 | AA | Present Invention |
| C-63 | BB | Present Invention |
| C-17 | AA | Present Invention |
| C-62 | BB | Present Invention |
| C-61 | BB | Present Invention |
| C-25 | AA | Present Invention |
| C-24 | AA | Present Invention |
| C-23 | AA | Present Invention |
| Comparative Compound 1 | CC | Comparative Example |
| Comparative Compound 2 | CC | Comparative Example |
| Comparative Compound 3 | CC | Comparative Example |
| Comparative Compound 4 | CC | Comparative Example |
| Comparative Compound 5 | CC | Comparative Example |
| Comparative Compound 6 | CC | Comparative Example |

From Table I, the imide derivative of the present invention has the luminous quantum yield in the film state that is large with respect to the luminous quantum yield in the solution state (film state/solution state), which means that the luminous quantum yield was less reduced due to concentration quenching.

Example 2

<Luminous Particles>

The luminescence quantum yield in the luminous particles was measured for the exemplified compounds that are the imide derivatives of the present invention and the comparative compounds shown in Table I.

(1) Preparation of Luminous Particles

A mixed solution including polystyrene particles and each of the above compounds of the present invention was prepared by adding, to 96 μL of a polystyrene (PS) particle dispersion liquid (solid content 5.2% by mass, volume average particle diameter of polystyrene particles 0.12 μm, dispersion medium: water), 100 μL of water, 50 μL of 2% aqueous solution of nonionic surfactant (Kolliphor P407: manufactured by Sigma Aldrich), and 100 μL of 0.01 mmol/L THF solution of the compound of the present invention. Polystyrene particles were prepared by stirring this mixed solution at 25° C. for 2 minutes.

Using the obtained dispersion liquid of polystyrene particles, the particles were precipitated by a centrifugal purification method, the supernatant was removed, and then pure water was added to redisperse the particles. This operation (centrifugal purification and redispersion) was repeated 4 times to obtain a dispersion liquid containing luminous particles containing each of the imide derivatives.

(2) Evaluation of Quantum Yield

The absolute fluorescence quantum yield of the dispersion liquid containing the polystyrene particles obtained in the previous item was measured using a fluorescence quantum yield spectrometer (C11347-01 manufactured by Hamamatsu Photonics K.K.), and was evaluated based on a relative luminous quantum yield, a relative value of the measured value when the fluorescence quantum yield of the comparative compound assumed to be 1.

The above results are shown in Table II to Table VII.

TABLE II

| Compound | Relative Luminous Quantum Yield | Remarks |
| --- | --- | --- |
| C-53 | 25 | Present Invention |
| C-49 | 37 | Present Invention |
| C-58 | 17 | Present Invention |
| C-55 | 9 | Present Invention |
| C-46 | 5 | Present Invention |
| C-45 | 9 | Present Invention |
| C-89 | 14 | Present Invention |
| C-166 | 30 | Present Invention |
| C-47 | 21 | Present Invention |
| C-164 | 18 | Present Invention |
| C-51 | 21 | Present Invention |
| Comparative Compound 1 | 1 | Comparative Example |

TABLE III

| Compound | Relative Luminous Quantum Yield | Remarks |
| --- | --- | --- |
| C-19 | 8 | Present Invention |
| Comparative Compound 2 | 1 | Comparative Example |

TABLE IV

| Compound | Relative Luminous Quantum Yield | Remarks |
| --- | --- | --- |
| C-17 | 11 | Present Invention |
| Comparative Compound 3 | 1 | Comparative Example |

TABLE V

| Compound | Relative Luminous Quantum Yield | Remarks |
| --- | --- | --- |
| C-62 | 12 | Present Invention |
| C-25 | 21 | Present Invention |
| Comparative Compound 4 | 1 | Comparative Example |

TABLE VI

| Compound | Relative Luminous Quantum Yield | Remarks |
| --- | --- | --- |
| C-61 | 5 | Present Invention |
| C-23 | 15 | Present Invention |
| Comparative Compound 5 | 1 | Comparative Example |

TABLE VII

| Compound | Relative Luminous Quantum Yield | Remarks |
| --- | --- | --- |
| C-63 | 11 | Present Invention |
| C-24 | 18 | Present Invention |
| Comparative Compound 6 | 1 | Comparative Example |

From Table II to Table VII, it can be seen that the imide derivatives of the present invention exhibit higher luminous quantum yield(s) in polymer particles with respect to the comparative compounds.

INDUSTRIAL APPLICABILITY

The imide derivative of the present invention can exhibit a high luminous quantum yield not only in a dilute solution but also in a high concentration solution or in a film state due to suppressed concentration quenching. Therefore, it can be preferably used as a luminescent composition, a luminous thin film, and luminous particles. For example, it can be applied to an organic electronic device such as an organic electroluminescence element. It can also be applied to a marker in biology and medicine in bioimaging. Furthermore, it can be can be used as a color conversion filter applicable to dyes, pigments, optical filters, agricultural films, and the like.

The invention claimed is:
1. An imide derivative having a structure represented by general formula (4) below:

General formula (4)

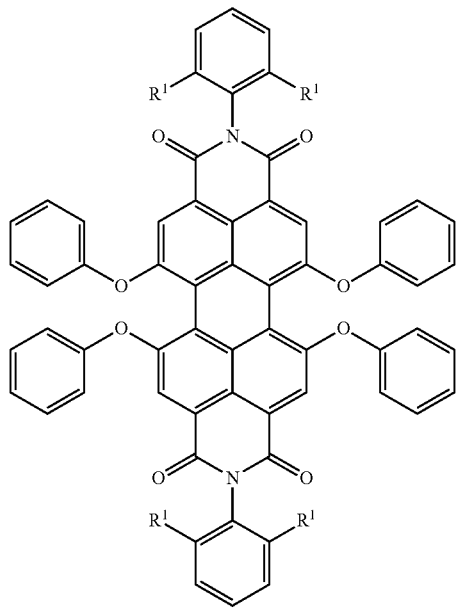

wherein, in the general formula (4), a plurality of $R^1$ each independently represent a hydrogen atom or a substituent, and at least one $R^1$ represents a group having 4 to 30 carbon atoms, wherein the group having 4 to 30 carbon atoms is an alkyl group substituted with a cycloalkyl group.

2. An imide derivative having a structure represented by general formula (5) below:

General formula (5)

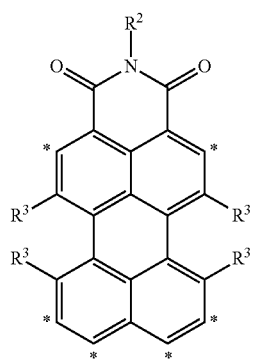

wherein, in the general formula (5), $R^2$ represents a substituted or unsubstituted alkyl group, aryl group, or heteroaryl group; a plurality of $R^3$ each independently represent a hydrogen atom or a group having a structure represented by general formula (6) below, and at least two $R^3$ independently represent a group having a structure represented by general formula (6) below; and a naphthalene ring optionally further has a substituent, and * represents a position of a substituent that the naphthalene ring optionally has, when two or more positions of * have substituents, the substituents optionally form a ring, and each substituent at the position of * is optionally further substituted with one or more second substituents that optionally form a ring, General formula (6)

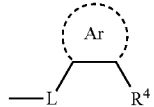

wherein, in the general formula (6), Ar represents an aryl ring or a heteroaryl ring; $R^4$ represents a substituent other than a phenyl group; two or more groups represented by general formula (6) are present, and two $R^4$ are bonded to each other; L represents a single bond, an oxygen atom, a sulfur atom, or —NR'—; and R' represents a hydrogen atom, an alkyl group, an aryl group, or a heteroaryl group.

3. The imide derivative according to claim 2, wherein the imide derivative having a structure represented by the general formula (5) has a structure represented by general formula (7-1) to general formula (7-4) below:

General formula (7-1)

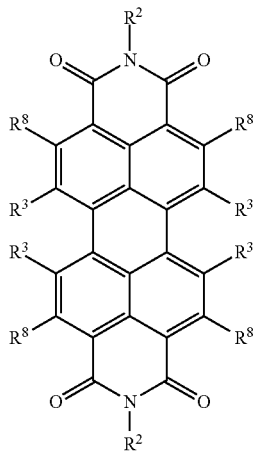

General formula (7-2)

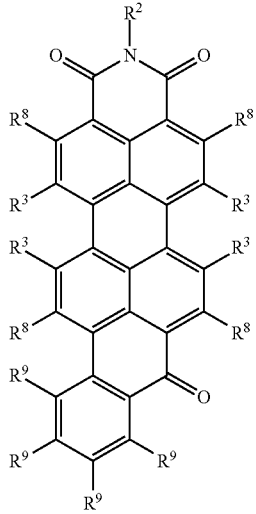

-continued

General formula (7-3)

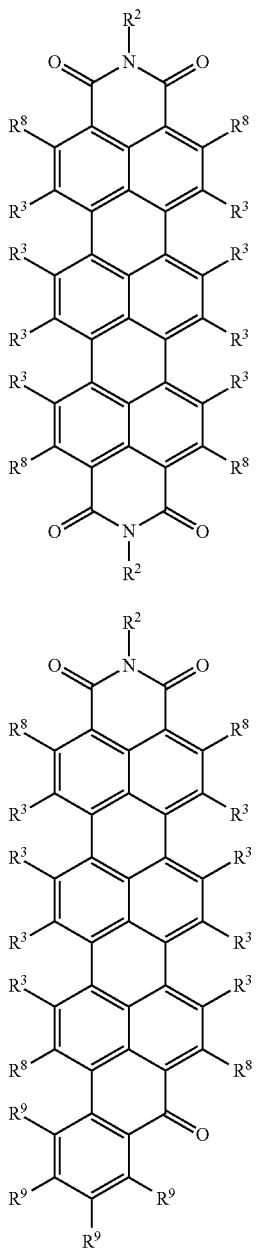

General formula (7-4)

wherein, in the general formula (7-1) to general formula (7-4), $R^2$ each independently represents a substituted or unsubstituted alkyl group, aryl group, or heteroaryl group; a plurality of $R^3$ each independently represent a hydrogen atom or a group having a structure represented by the general formula (6), and at least two $R^3$ independently represent a group having a structure represented by the general formula (6); and $R^8$ and $R^9$ each independently represent a hydrogen atom, an alkyl group, an alkenyl group, an alkynyl group, an aryl group, a heteroaryl group, an alkoxy group, or an aryloxy group.

4. The imide derivative according to claim 3, wherein the imide derivative having a structure represented by the general formula (7-1) has a structure represented by general formula (8) below:

General formula (8)

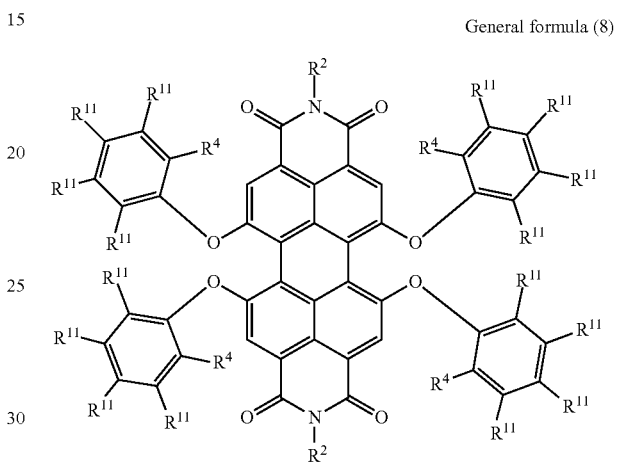

wherein, in the general formula (8), a plurality of $R^2$ each independently represent a substituted or unsubstituted alkyl group, aryl group, or heteroaryl group; $R^4$ each represent a substituent other than a phenyl group; two $R^4$ are bonded to each other; and $R^{11}$ each independently represents a hydrogen atom, an alkyl group, an aryl group, a heteroaryl group, an alkenyl group, an alkynyl group, an alkoxy group, an aryloxy group, an amino group, an acyl group, an acyloxy group, an amide group, a carboxy group, or a sulfo group.

5. The imide derivative according to claim 4, wherein, in the general formula (8), any two $R^4$ are bonded to each other across a perylene.

6. A luminescent composition comprising:
the imide derivative according to claim 1.

7. A luminous thin film comprising:
the imide derivative according to claim 1.

8. A luminous particle comprising:
the imide derivative according to claim 1.

* * * * *